(12) United States Patent
Stuart et al.

(10) Patent No.: US 12,042,402 B2
(45) Date of Patent: Jul. 23, 2024

(54) SACRO-ILIAC JOINT STABILIZING IMPLANTS AND METHODS OF IMPLANTATION

(71) Applicant: SI-Bone Inc., Santa Clara, CA (US)

(72) Inventors: Mary E. Stuart, Santa Clara, CA (US); Paul M. Sand, Redwood City, CA (US); Bret W. Schneider, San Jose, CA (US); W. Carlton Reckling, Cheyenne, WY (US); Francois Follini, Austin, TX (US); Scott A. Yerby, Montara, CA (US); Vikas V. Patel, Denver, CO (US); Jack B. Rentz, Morrison, CO (US); Richard A. Hynes, Melbourne Beach, FL (US); Babajide Ogunseinde, Longview, TX (US); David A. Provenzano, Bridgeville, PA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 18/356,880

(22) Filed: Jul. 21, 2023

(65) Prior Publication Data

US 2024/0122724 A1     Apr. 18, 2024

Related U.S. Application Data

(63) Continuation of application No. 17/812,945, filed on Jul. 15, 2022, now Pat. No. 11,752,011, which is a
(Continued)

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3013* (2013.01);
(Continued)

(58) Field of Classification Search
CPC .. A61F 2/44; A61F 2/442; A61F 2/447; A61F 2/30771; A61F 2002/3013;
(Continued)

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

ACUMED; Acutrak Headless Compressioin Screw (product information); 12 pgs; @2005; retrieved Sep. 25, 2014 from http://www.rcsed.ac.uk/fellows/Ivanrensburg/classification/surgtech/acumed/manuals/acutrak-brochure%200311.pdf.

(Continued)

*Primary Examiner* — Jessica Weiss
(74) *Attorney, Agent, or Firm* — Shay Glenn LLP

(57) ABSTRACT

Sacro-iliac joint stabilizing implants adapted for implanting across a SI joint from a dorsal approach. Methods of, and delivery tools adapted for implanting sacro-iliac joint stabilizing implants across a SI joint from a dorsal approach.

13 Claims, 69 Drawing Sheets

Related U.S. Application Data continuation of application No. PCT/US2021/062337, filed on Dec. 8, 2021.

(60) Provisional application No. 63/202,390, filed on Jun. 9, 2021, provisional application No. 63/123,404, filed on Dec. 9, 2020.

(52) U.S. Cl.
CPC ............... *A61F 2002/30151* (2013.01); *A61F 2002/30235* (2013.01); *A61F 2002/30261* (2013.01); *A61F 2002/30845* (2013.01); *A61F 2002/3092* (2013.01)

(58) Field of Classification Search
CPC .. A61F 2002/30151; A61F 2002/30235; A61F 2002/30261; A61F 2002/30845; A61F 2002/3092
USPC ................ 623/17.11–17.16; 606/99–100
See application file for complete search history.

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 * | 8/2002 | Shapiro ............ A61F 2/446 623/17.11 |
| 6,451,020 B1 | 9/2002 | Zucherman et al. |
| 6,471,707 B1 | 10/2002 | Miller et al. |
| 6,485,518 B1 | 11/2002 | Cornwall et al. |

(56) References Cited

U.S. PATENT DOCUMENTS

| | | |
|---|---|---|
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaus et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |

(56) References Cited

U.S. PATENT DOCUMENTS

| | | |
|---|---|---|
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,826,986 B2 | 11/2017 | Donner et al. |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,653,544 B2 | 5/2020 | Forsell |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |
| 10,682,150 B2 | 6/2020 | Stark |
| 10,682,437 B2 | 6/2020 | Roth |
| 10,709,570 B2 | 7/2020 | Stauffer et al. |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Sournac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,940,008 B2 | 3/2021 | Patel |
| 10,959,758 B2 | 3/2021 | Mesiwala et al. |
| 10,959,830 B2 | 3/2021 | Williams et al. |
| 10,987,142 B2 | 4/2021 | Poelstra et al. |
| 10,993,754 B2 | 5/2021 | Kuntz et al. |
| 10,993,757 B2 | 5/2021 | Schifano et al. |
| 11,006,985 B2 | 5/2021 | Caploon et al. |
| D921,898 S | 6/2021 | Schifano et al. |
| D922,568 S | 6/2021 | Schifano et al. |

(56) References Cited

U.S. PATENT DOCUMENTS

| | | |
|---|---|---|
| 11,020,129 B2 | 6/2021 | LaNeve et al. |
| 11,033,309 B2 | 6/2021 | Zadeh |
| 11,052,229 B2 | 7/2021 | Althoff et al. |
| 11,058,443 B2 | 7/2021 | Siccardi et al. |
| 11,058,550 B2 | 7/2021 | LaNeve et al. |
| 11,058,556 B2 | 7/2021 | LaNeve et al. |
| 11,071,573 B2 | 7/2021 | Schneider et al. |
| D927,295 S | 8/2021 | Lanois |
| 11,116,519 B2 | 9/2021 | Sand et al. |
| 11,116,557 B2 | 9/2021 | Zander et al. |
| 11,147,591 B2 | 10/2021 | Jackson |
| 11,147,597 B2 | 10/2021 | Jackson |
| 11,147,688 B2 | 10/2021 | Reckling et al. |
| 11,154,402 B1 | 10/2021 | LaNeve et al. |
| D935,025 S | 11/2021 | Schifano et al. |
| D935,876 S | 11/2021 | Lanois |
| 11,166,821 B2 | 11/2021 | Sazy |
| 11,172,939 B2 | 11/2021 | Donner et al. |
| 11,172,969 B2 | 11/2021 | Suddaby |
| 11,219,534 B2 | 1/2022 | Wall |
| 11,224,467 B2 | 1/2022 | Peterson et al. |
| 11,224,490 B2 | 1/2022 | MacMillan et al. |
| 11,234,830 B2 | 2/2022 | Mesiwala et al. |
| 11,259,854 B2 | 3/2022 | Thomes et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,291,485 B2 | 4/2022 | Mauldin et al. |
| 11,298,747 B2 | 4/2022 | Klein et al. |
| D951,455 S | 5/2022 | Ginn |
| D952,147 S | 5/2022 | Schifano et al. |
| 11,318,020 B2 | 5/2022 | Bohl |
| 11,337,821 B2 | 5/2022 | Mauldin et al. |
| 11,369,419 B2 | 6/2022 | Mesiwala et al. |
| 11,382,755 B2 | 7/2022 | LaNeve et al. |
| 11,382,770 B2 | 7/2022 | LaNeve et al. |
| 11,389,305 B2 | 7/2022 | LaNeve et al. |
| 11,413,073 B2 | 8/2022 | Castro |
| 11,419,652 B2 | 8/2022 | Wickham et al. |
| 11,419,653 B2 | 8/2022 | Castro |
| 11,419,654 B2 | 8/2022 | Castro |
| 11,432,829 B2 | 9/2022 | Castro |
| 11,446,069 B2 | 9/2022 | Mauldin et al. |
| 11,452,548 B2 | 9/2022 | Harshman et al. |
| 11,471,286 B2 | 10/2022 | Mauldin et al. |
| 11,478,287 B2 | 10/2022 | Mauldin et al. |
| 11,510,801 B2 | 11/2022 | Archbold |
| D972,137 S | 12/2022 | Schifano et al. |
| 11,517,361 B2 | 12/2022 | Major et al. |
| 11,553,945 B2 | 1/2023 | Castro |
| 11,553,948 B2 | 1/2023 | Haller et al. |
| 11,553,953 B1 | 1/2023 | Robbins |
| 11,571,245 B2 | 2/2023 | Stuart et al. |
| 11,580,268 B2 | 2/2023 | Suddaby |
| 11,583,326 B2 | 2/2023 | Suddaby |
| 11,607,251 B2 | 3/2023 | Albert et al. |
| 11,607,256 B1 | 3/2023 | Folsom et al. |
| 11,633,292 B2 | 4/2023 | Reiley |
| 11,660,126 B1 | 5/2023 | Abbasi et al. |
| 11,672,570 B2 | 6/2023 | Stuart et al. |
| 11,672,664 B2 | 6/2023 | Mauldin et al. |
| 11,678,997 B2 | 6/2023 | Mesiwala et al. |
| 11,684,378 B2 | 6/2023 | Reiley et al. |
| 11,752,011 B2 | 9/2023 | Stuart et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |

(56) References Cited

U.S. PATENT DOCUMENTS

| | | |
|---|---|---|
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154314 A1 | 6/2008 | McDevitt |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | Mckinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1* | 7/2009 | Abdou .............. A61B 17/1757 606/279 |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1* | 4/2011 | Jacob ................. A61B 17/7055 623/17.11 |
| 2011/0098817 A1 | 4/2011 | Eckhardt et al. |
| 2011/0106175 A1 | 5/2011 | Rezach |
| 2011/0118841 A1* | 5/2011 | Reiley ................ A61B 17/1615 623/17.11 |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184478 A1* | 7/2011 | Reiley ................ A61B 17/8685 606/86 R |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |

(56) References Cited

U.S. PATENT DOCUMENTS

| | | |
|---|---|---|
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1* | 3/2015 | Chin ............... A61B 17/7055 606/304 |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1* | 12/2015 | Donner ............... A61B 17/84 600/595 |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0184105 A1* | 6/2016 | Donner ............... A61F 2/4455 623/17.11 |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |

(56) References Cited

U.S. PATENT DOCUMENTS

| | | |
|---|---|---|
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0104063 A1 | 4/2018 | Asaad |
| 2018/0104068 A1 | 4/2018 | Sack |
| 2018/0110624 A1 | 4/2018 | Amone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0226613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0360512 A1 | 12/2018 | Mari |
| 2018/0360608 A1* | 12/2018 | Aksu .................. A61F 2/30 |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0093603 A1 | 3/2020 | Manwill et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0146721 A1 | 5/2020 | Sadiq |
| 2020/0149137 A1 | 5/2020 | Roth |
| 2020/0170679 A1 | 6/2020 | Sciubba et al. |
| 2020/0206390 A1 | 7/2020 | Roth |
| 2020/0222088 A1 | 7/2020 | Kraus |
| 2020/0222195 A1 | 7/2020 | Assell et al. |
| 2020/0246158 A1 | 8/2020 | Bergey |
| 2020/0254140 A1 | 8/2020 | Roth |
| 2020/0268449 A1 | 8/2020 | Solitro et al. |
| 2020/0268518 A1 | 8/2020 | Suh et al. |
| 2020/0276019 A1 | 9/2020 | Shetty et al. |
| 2020/0281729 A1 | 9/2020 | Schifano et al. |
| 2020/0297496 A1 | 9/2020 | Mullin |
| 2020/0305896 A1 | 10/2020 | Castro |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0323563 A1 | 10/2020 | Rezach et al. |
| 2020/0345507 A1 | 11/2020 | Reiley |
| 2020/0345508 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0085470 A1 | 3/2021 | Ty |
| 2021/0107093 A1 | 4/2021 | Tempco |
| 2021/0169660 A1 | 6/2021 | Reckling et al. |
| 2021/0196332 A1 | 7/2021 | Patel |
| 2021/0212734 A1 | 7/2021 | Mesiwala et al. |
| 2021/0212833 A1 | 7/2021 | Chin et al. |
| 2021/0228360 A1 | 7/2021 | Hunt et al. |
| 2021/0228363 A1 | 7/2021 | Suddaby |
| 2021/0236146 A1 | 8/2021 | Donner et al. |
| 2021/0244449 A1 | 8/2021 | Castro |
| 2021/0244452 A1 | 8/2021 | Castro |
| 2021/0275233 A1 | 9/2021 | Fang et al. |
| 2021/0338454 A1 | 11/2021 | Afzal |
| 2021/0346038 A1 | 11/2021 | Fiechter et al. |
| 2021/0353337 A1 | 11/2021 | Kaufmann et al. |
| 2021/0353338 A1 | 11/2021 | Meek et al. |
| 2021/0393298 A1 | 12/2021 | Castro |
| 2021/0393408 A1 | 12/2021 | Ginn |
| 2021/0393409 A1 | 12/2021 | Ginn |
| 2022/0031365 A1 | 2/2022 | Suh et al. |
| 2022/0031474 A1 | 2/2022 | Reckling et al. |
| 2022/0096098 A1 | 3/2022 | Sand et al. |
| 2022/0117640 A1 | 4/2022 | Schneider et al. |
| 2022/0273447 A1 | 9/2022 | Ginn |
| 2022/0273448 A1 | 9/2022 | Ginn et al. |
| 2022/0280303 A1 | 9/2022 | Mauldin et al. |
| 2022/0296377 A1 | 9/2022 | Ginn et al. |
| 2022/0296378 A1 | 9/2022 | Ginn |
| 2022/0304672 A1 | 9/2022 | Kalhorn et al. |
| 2022/0304813 A1 | 9/2022 | Ginn et al. |
| 2022/0304814 A1 | 9/2022 | Ginn |
| 2022/0354654 A1 | 11/2022 | Lewis et al. |
| 2022/0354665 A1 | 11/2022 | Mesiwala et al. |
| 2022/0361924 A1 | 11/2022 | Castro |
| 2022/0409381 A1 | 12/2022 | Ginn |
| 2023/0000526 A1 | 1/2023 | Follini et al. |
| 2023/0000630 A1 | 1/2023 | Ginn et al. |

(56) References Cited

U.S. PATENT DOCUMENTS

| | | |
|---|---|---|
| 2023/0000631 A1 | 1/2023 | Ginn et al. |
| 2023/0014384 A1 | 1/2023 | Cordonnier et al. |
| 2023/0025644 A1 | 1/2023 | Maxwell et al. |
| 2023/0032203 A1 | 2/2023 | Maxwell et al. |
| 2023/0047553 A1 | 2/2023 | Fauth et al. |
| 2023/0048409 A1 | 2/2023 | Mangone et al. |
| 2023/0049559 A1 | 2/2023 | Fauth et al. |
| 2023/0076180 A1 | 3/2023 | Schifano et al. |
| 2023/0088477 A1 | 3/2023 | Roussouly et al. |
| 2023/0095586 A1 | 3/2023 | Mauldin et al. |
| 2023/0145974 A1 | 5/2023 | Asfora |
| 2023/0210667 A1 | 7/2023 | Lindsey et al. |
| 2023/0263554 A1 | 8/2023 | Stuart et al. |
| 2023/0270559 A1 | 8/2023 | Mesiwala et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| CN | 102429716 A | 5/2012 |
| CN | 104968283 A | 10/2015 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3501457 A1 | 6/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009000501 A | 1/2009 |
| JP | 2009521990 A | 6/2009 |
| JP | 2009533159 A | 9/2009 |
| JP | 2010137016 A | 6/2010 |
| JP | 2012030105 A | 2/2012 |
| JP | 2014000402 A | 1/2014 |
| JP | 2015510506 A | 4/2015 |
| JP | 2017528251 A | 9/2017 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2014/145902 A1 | 9/2014 |
| WO | WO2017/147140 A1 | 8/2017 |
| WO | WO2017/147537 A1 | 8/2017 |
| WO | WO2017//201371 A1 | 11/2017 |
| WO | WO2019/152737 A1 | 8/2019 |
| WO | WO2020/168269 A1 | 8/2020 |
| WO | WO2022/125619 A1 | 6/2022 |
| WO | WO2023/102533 A1 | 6/2023 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Eisner; New SI Joint Fusion System Cleared; Orthopedics This Week; Jun. 28, 2018; retreived from the internet <https://ryortho.com/breaking/new-si-joint-fusion-system-cleared/> on Sep. 8, 2022; 5 pages.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al., Minimally invasive sacroiliac arthrodesis, outcomes of a new technique; J Spinal Disord Tech; vol. 21; No. 8; pp. 579-584; Dec. 2008.

Third Party Observation; PCT/US2021/062337; Aug. 29, 2022; 6 pages.

Reiley et al.; U.S. Appl. No. 18/317,832 entitled "Implants for bone fixation or fusion," filed May 15, 2023.

Mauldin et al.; U.S. Appl. No. 18/311,103 entitled "Systems, device, and methods for joint fusion," filed May 2, 2023.

* cited by examiner

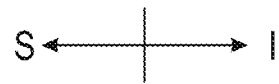
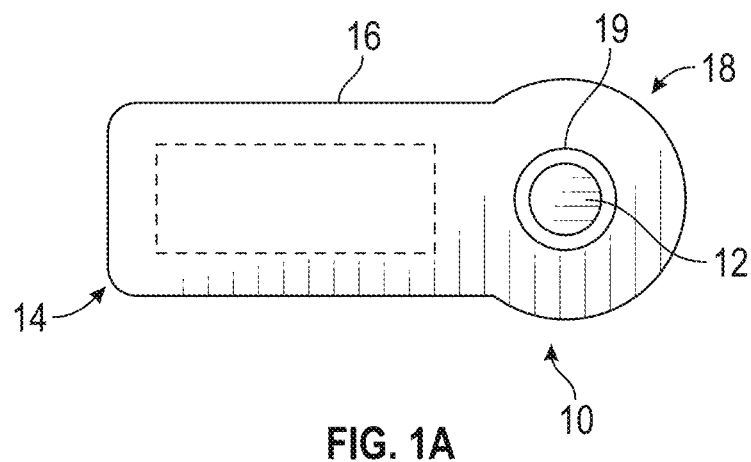
FIG. 1A
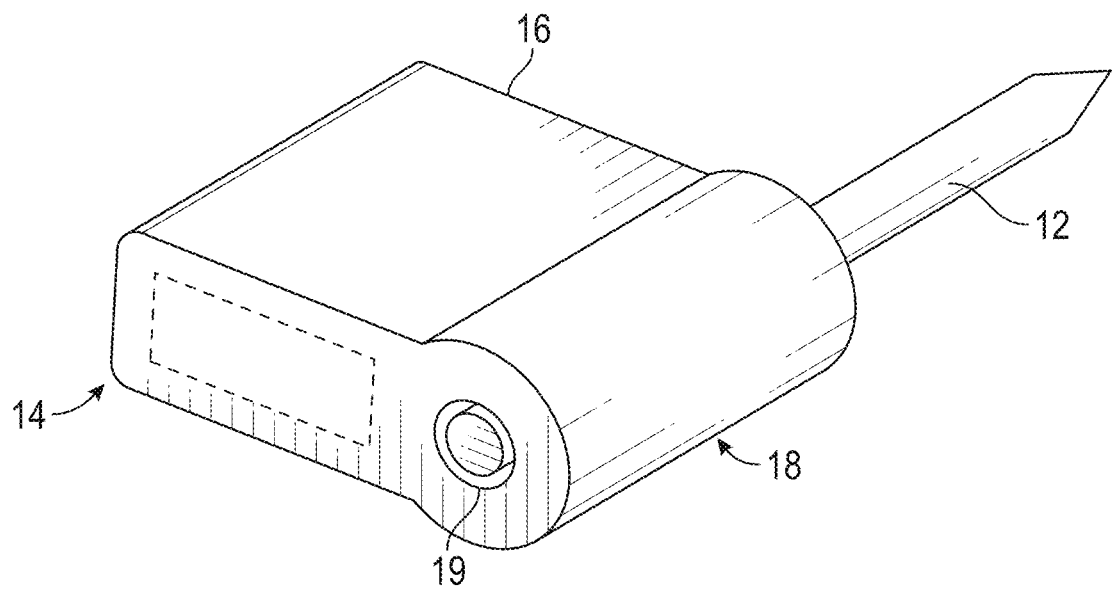
FIG. 1B

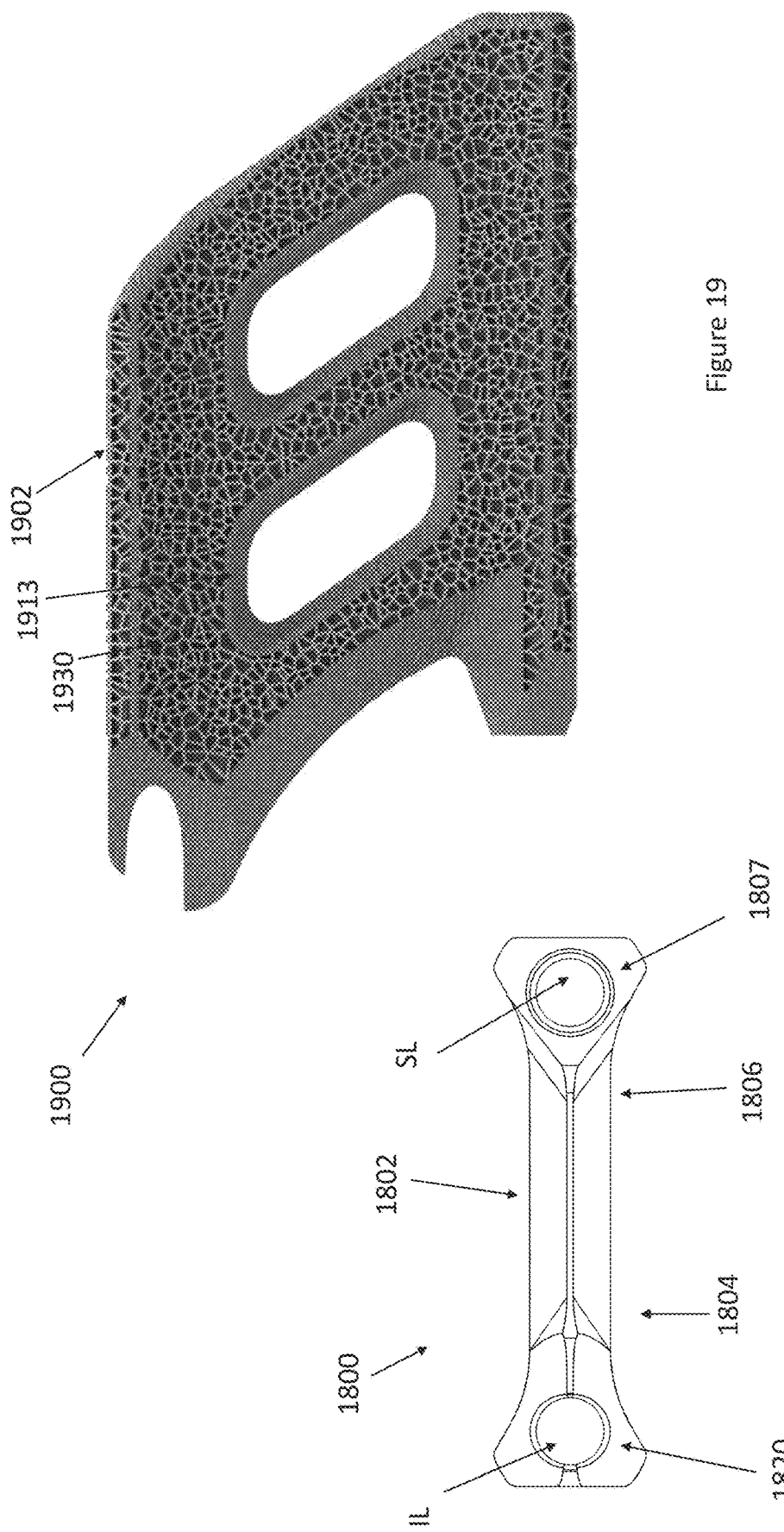

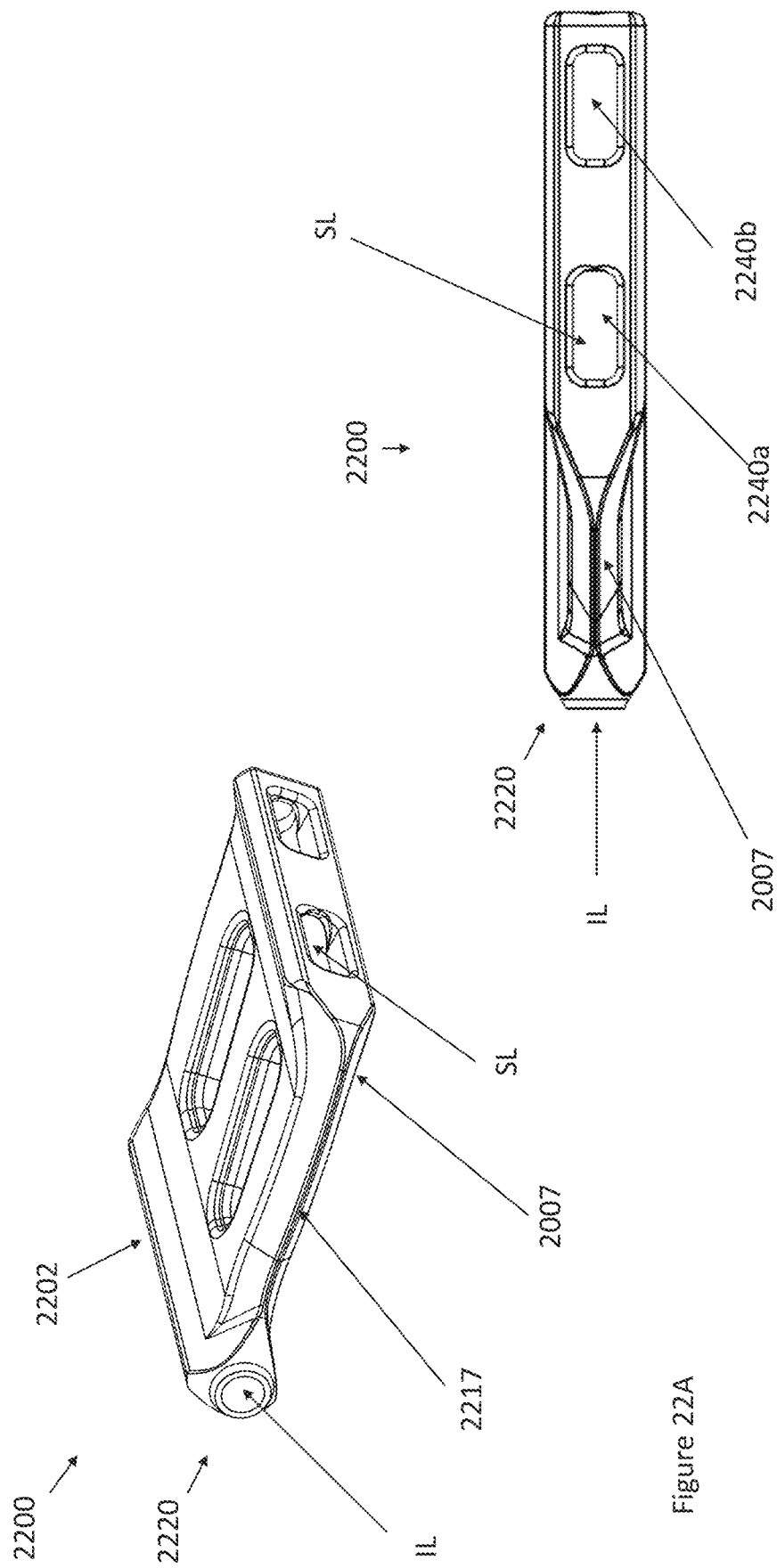

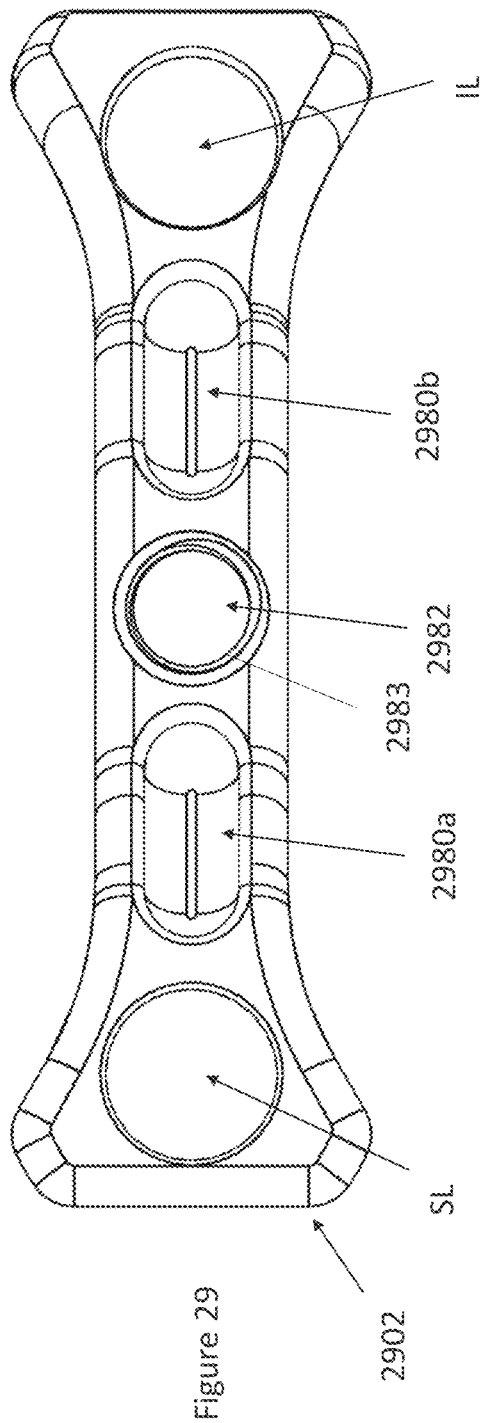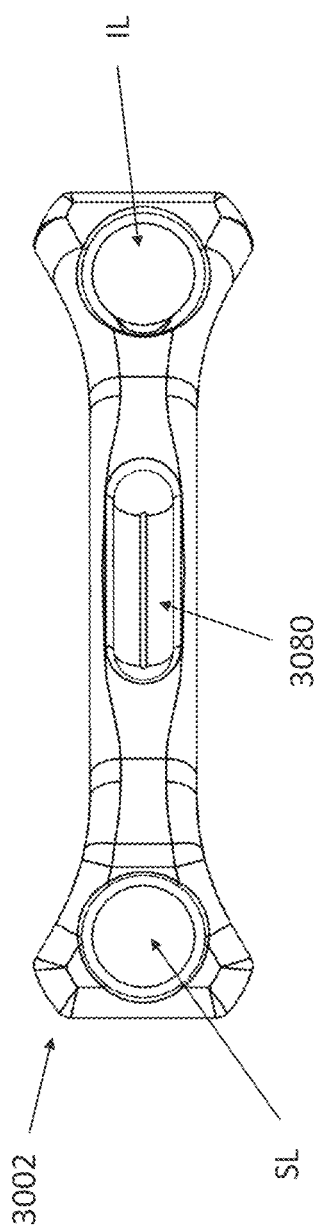

Figure 41B (lateral view)
Figure 41A

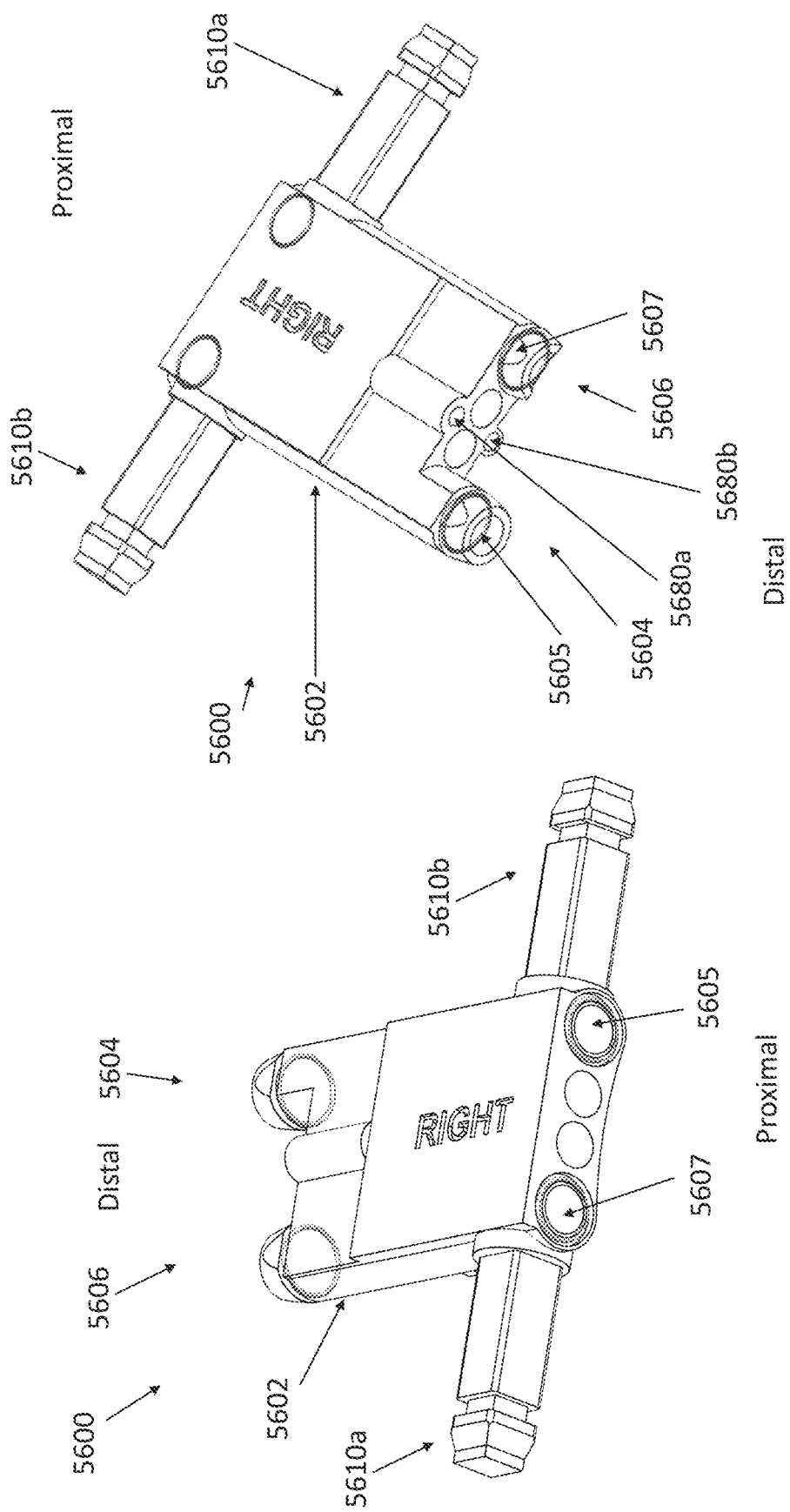

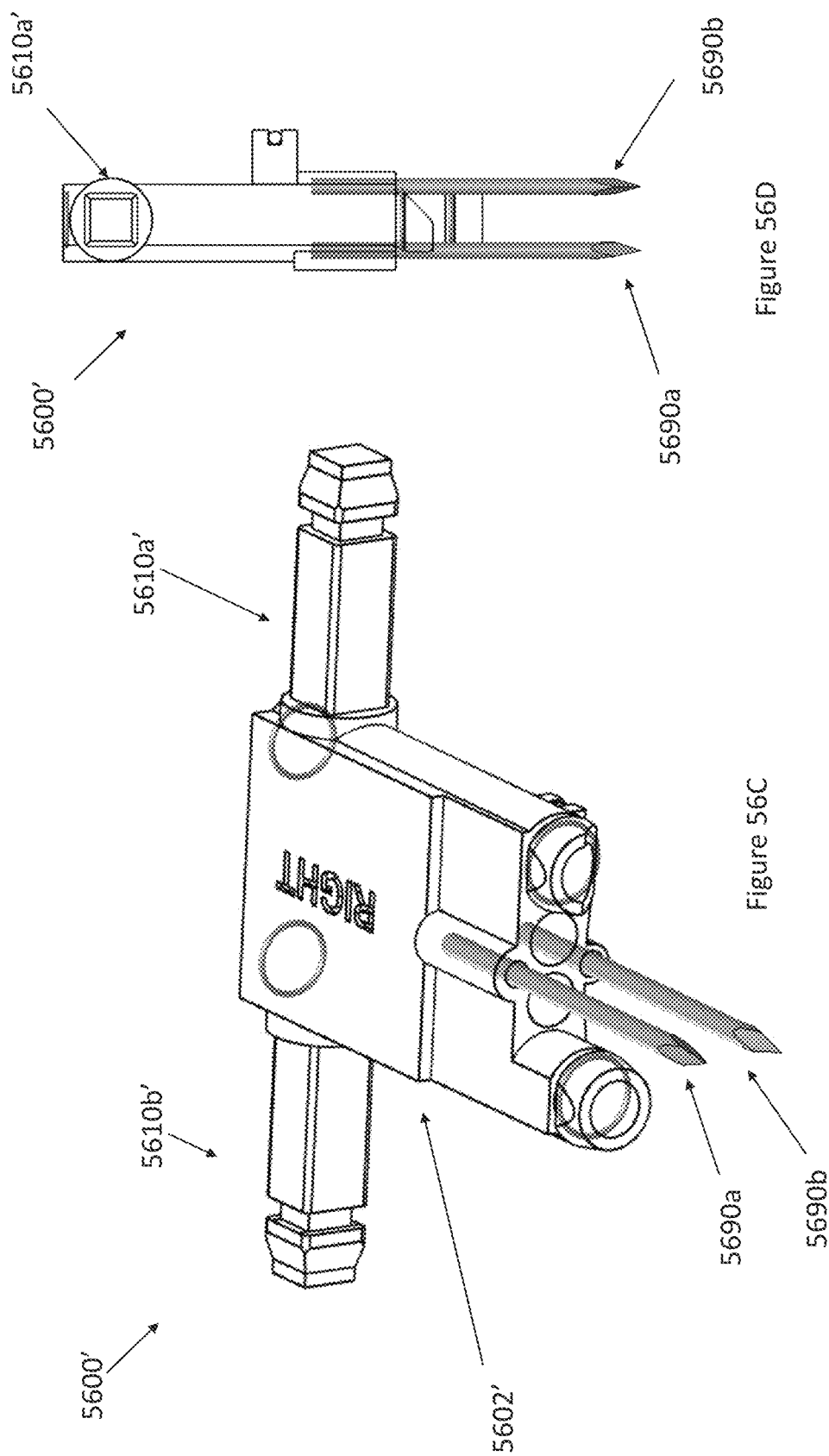

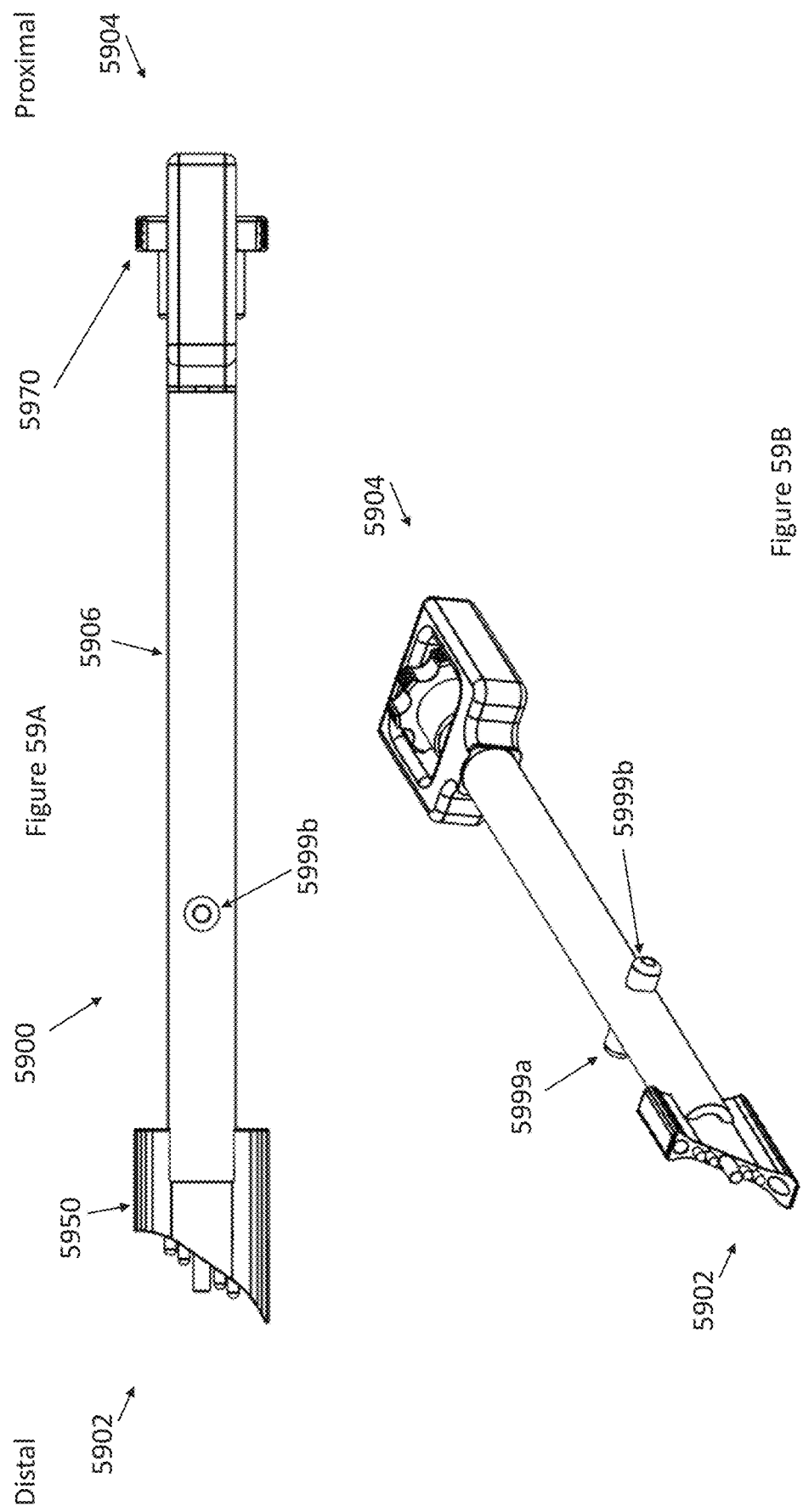

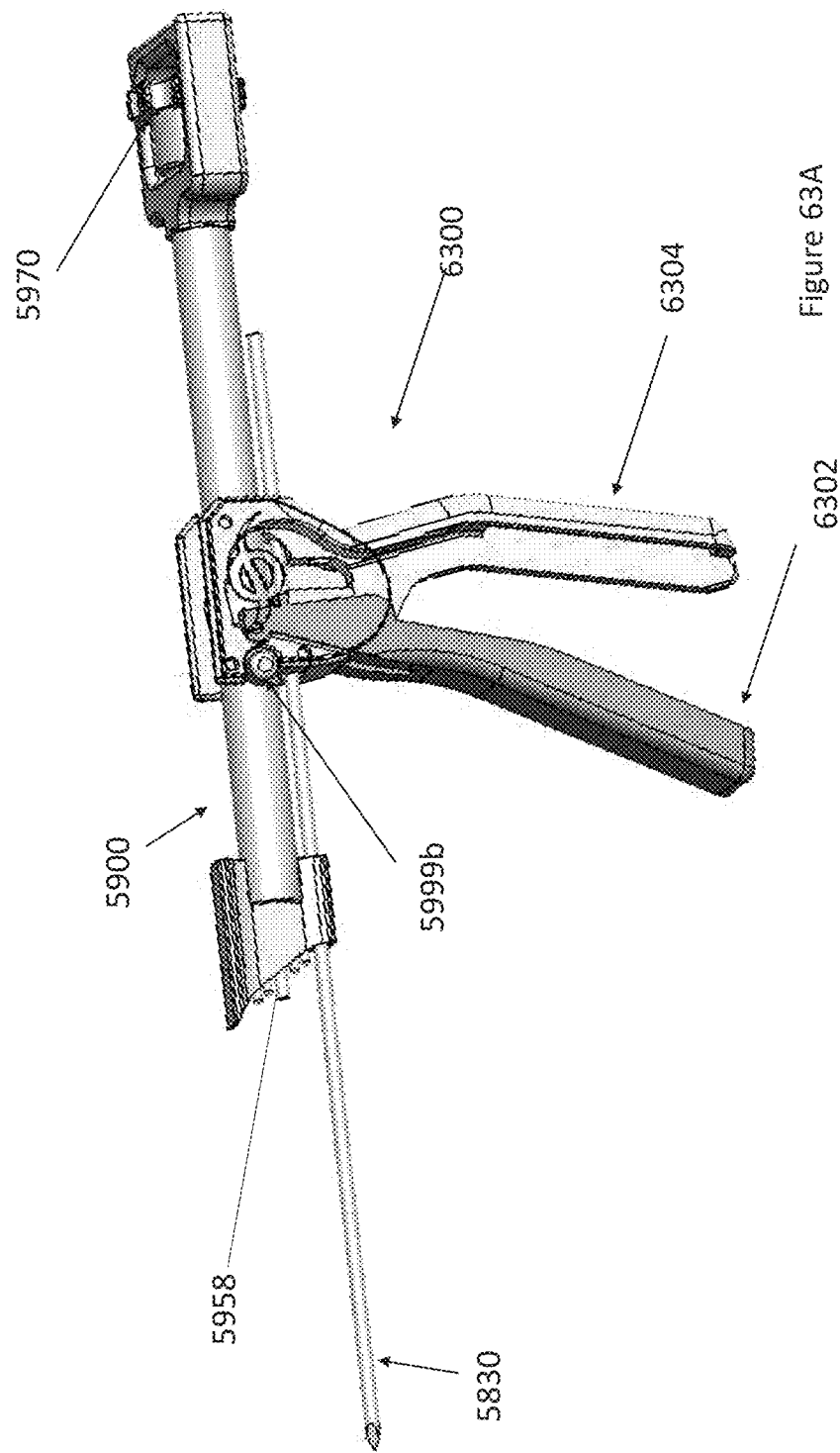

SACRO-ILIAC JOINT STABILIZING IMPLANTS AND METHODS OF IMPLANTATION

CROSS REFERENCE TO RELATED APPLICATIONS

This application is a continuation of U.S. application Ser. No. 17/812,945, filed Jul. 15, 2022, which is a continuation of International Application No. PCT/US2021/062337, filed Dec. 8, 2021, which claims the benefit of priority to U.S. Prov. No. 63/123,404, filed Dec. 9, 2020, and U.S. Prov. No. 63/202,390 filed Jun. 9, 2021, the disclosures of which are incorporated by reference herein in their entireties for all purposes.

INCORPORATION BY REFERENCE

This application incorporates by reference in its entirety for all purposes the entire disclosure of PCT publication WO2021/119126A1.

All publications and patent applications mentioned in this specification are herein incorporated by reference to the same extent as if each individual publication or patent application was specifically and individually indicated to be incorporated by reference.

BACKGROUND

Implants may be positioned across a sacro-iliac ("SI") joint to help stabilize the joint. Portions of the ilium may have greater density than portions of the sacrum into which the implant is implanted. Depending on one or more of the delivery trajectories, the target location for implantation, and the configuration of the implant, the differences in bone density may present challenges while advancing some SI joint implants across the SI joint. Implants and methods of delivery are needed that accommodate for the differences in bone density and can facilitate the successful delivery of the SI joint implant from a dorsal approach across the SI joint. Additionally, implants are needed that are configured and sized to be safely implanted into a target anatomical region.

SUMMARY OF THE DISCLOSURE

This disclosure describes implants that are sized and configured to be implanted across an SI Joint from a dorsal trajectory to stabilize the joint.

This disclosure also describes delivery tools that are adapted to deliver and position implants across an SI Joint from a dorsal trajectory.

This disclosure also describes methods of implanting implants across an SI Joint from a dorsal trajectory.

One aspect of the disclosure is a sacro-iliac joint stabilizing implant for implanting across a SI joint from a dorsal approach, the implant having an implant body. The implant body has a central joint portion for placement across the SI joint, an ilium portion on a first lateral side of the central joint portion, the ilium portion sized and configured for implanting into an ilium when the implant is implanted across a SI joint from a dorsal approach, and a sacrum portion on a second lateral side of the central joint portion, the sacrum portion sized and configured for implanting into a sacrum when the implant is implanted across the SI joint from the dorsal approach.

In this aspect, the implant body may have a wafer configuration with a width dimension greater than a height dimension.

In this aspect, the ilium portion may comprise and define an elongate ilium lumen that extends from a distal opening to a proximal opening and has an ilium lumen longitudinal axis, the ilium lumen sized and configured to receive therein an ilium positioning guide.

In this aspect, and with reference to a line that is orthogonal to an ilium lumen axis, the sacrum portion may extend further proximally than the ilium portion.

In this aspect, the implant body may include a distal portion that includes a sharpened distal end extending at least in the central joint portion, the sharpened distal end having a tapered configuration with a first surface that tapers downward and distally from a top portion of the implant body and a second surface that tapers upward and distally from a bottom portion of the implant body.

In this aspect, the implant body may have a proximal end having at least one surface feature configured to interface with a delivery tool (e.g., an impactor) to facilitate delivery of the implant body in a direction of implantation, and with reference to a line orthogonal to the direction of implantation, the sacrum portion may extend further proximally than the ilium portion.

In this aspect, a sharpened distal end of the implant body may have, in a top view, a concave curved configuration along at least a portion of the sharpened distal end. A curved configuration may be asymmetrical about a long axis of the implant body. A sharpened distal end may extend further distally in the ilium portion than in the sacrum portion.

In this aspect, a sharpened distal end of the implant body may extend laterally through the sacrum portion, the central portion, and the ilium portion.

In this aspect, a sharpened distal end may comprise a smooth curve.

In this aspect, a portion of the ilium portion may extend further distally than a sharpened distal end.

In this aspect, a portion of the sacrum portion may extend further distally than at least a portion of a sharpened distal end.

In this aspect, the implant body may comprise a distal portion, at least a portion of the distal portion comprising a curved distal end extending laterally from the ilium portion, through the central portion, and into the sacrum portion.

In this aspect, an ilium lumen may have a length that is greater than a length of a sacrum lumen.

In this aspect, an ilium lumen may have a length that is the same as a length of a sacrum lumen.

In this aspect, a sacrum lumen may have a length that is greater than a length of an ilium lumen.

In this aspect, an ilium lumen may be parallel with a sacrum lumen.

In this aspect, the ilium portion has an ilium length, and the sacrum portion has a sacrum length, and the ilium length may be greater than the sacrum length, the ilium length may be the same as the sacrum length, or the sacrum length may be greater than the ilium length.

In this aspect, a sacrum lumen may extend further proximally than an ilium lumen.

In this aspect, an ilium lumen may extend further distally than a sacrum lumen.

In this aspect, at least one distal opening of optional lumens may extend further distally than at least a portion of the central portion of the implant body. Distal openings of more than one lumen may extend further distally than the central portion.

In this aspect, the implant body may further comprise an inner frame, and an outer porous network of interconnected struts extending about at least a top portion and a bottom portion of the implant. A porous network of interconnected struts may further extend about the ilium portion and the sacrum portion. A porous network of interconnected struts may further extend about a plurality of side fenestrations in each of an ilium side of the implant body and a sacrum side of the implant body, wherein the plurality of fenestrations in the ilium side may be in communication with an ilium lumen and the plurality of fenestrations in the sacrum side may be in communication with a sacrum lumen. A porous network of interconnected struts may comprise pores in a central region of the implant body that are larger in size than pores that extend about the ilium portion and larger than pores that extend about the sacrum portion. An inner frame may have a slanted "digital eight" configuration that is slanted distally on the ilium side. An inner frame may include first and second axially extending elongate members and a plurality of axially spaced apart connecting elongate members extending from the first elongate member to the second elongate member, each two adjacent connecting elongate members, along with the first and second axially extending elongate members, defining one of a plurality of frame fenestrations.

In this aspect, the implant body may have a height dimension that is not greater than 70% of a width dimension of the implant body. The height dimension may not be greater than 60% of the width dimension of the implant body.

In this aspect, the implant body may have a length from 15 mm to 80 mm.

In this aspect, the implant body may have a width from 15 mm to 50 mm.

In this aspect, the implant body may have a height from 4 mm to 20 mm.

In this aspect, the implant body, in a top view, may have a parallelogram configuration that does not include right angles.

In this aspect, the implant body may have, in a top view, a rhomboid configuration or a rhombus configuration.

In this aspect, the implant body may have a height that is not constant across a width of the implant body. A height dimension may be greater in at least a portion of in the ilium portion than in the central region, and wherein the height dimension may be greater in at least a portion of in the sacrum portion than in the central region. At least one of a top portion or a bottom portion of the implant body may have a curvature therein. A height dimension of the implant body may be greater in at least a portion of the central portion than in the ilium portion, and wherein the height dimension may be greater in at least the portion of the central portion than in the sacrum portion.

In this aspect, the ilium portion may comprise a cutting region proximally adjacent and disposed about the distal opening. A cutting region may comprise a plurality of axially-spaced cutting edges, which may be annular or circularly shaped.

In this aspect, the sacrum region may comprise a cutting region proximally adjacent and about the distal opening. A cutting region may comprise a plurality of axially-spaced cutting edges, which may be annular or circularly shaped.

In this aspect, a proximal end of the implant body may include a plurality of recessed members. A first recessed member may be in a first lateral half of the implant body, and a second recessed member may be in a second lateral half of the implant body.

In this aspect, a proximal end of the implant body may include a cylindrical channel (optionally extending along a long axis of the implant body) defining a lumen, wherein the channel comprises an inner thread.

One aspect of the disclosure is a method of positioning a sacro-iliac ("SI") joint stabilizing implant across an SI joint from a dorsal approach.

In this aspect, the method may include advancing an elongate sacrum pin from a dorsal starting point into a sacrum of a subject such that a distal end of the sacrum pin is in the sacrum and a proximal end of the sacrum pin is disposed outside of the subject.

In this aspect, the method may include advancing an elongate ilium pin from a dorsal starting point into an ilium of the subject such that a distal end of the ilium pin is in the ilium and a proximal end of the ilium pin is disposed outside of the subject.

In this aspect, the method may include advancing a distal opening of an ilium lumen that is in an ilium portion of an SI joint stabilizing implant over the ilium pin so as to restrict movement of the implant with respect to the ilium pin in at least one direction.

In this aspect, the method may include advancing a distal opening of a sacrum lumen that is in a sacrum portion of the SI joint stabilizing implant over the sacrum pin so as to restrict movement of the implant with respect to the sacrum pin in at least one direction.

In this aspect, the method may include advancing the implant distally over and relative to the sacrum pin and the ilium pin until the implant is across the SI joint with the ilium portion in the ilium and the sacrum portion in the sacrum.

In this aspect, the method may include removing the ilium pin and the sacrum pin from the subject, and leaving the implant positioned across the SI joint.

One aspect of this disclosure is a method of securing an SI-joint implant to an impactor.

In this aspect, the method may include causing a proximal end of the SI joint implant to be brought adjacent to a distal end of the impactor In this aspect, the method may include engaging a first securing element on the impactor with a second securing element disposed in a proximal region of the implant to secure the implant to the impactor and cause the implant to move axially with the impactor. In this aspect, a first securing element may be an elongate member with an external thread, and wherein the second securing element may be an internal channel with an internal thread. In this aspect, the method may include engaging a first impactor protrusion on a first lateral side of a first securing element with a first recess in the implant, and engaging a second impactor protrusion on a second lateral side of the first securing element with a second recess in the implant. In this aspect, the method may include causing a distal face of the impactor to be placed adjacent a proximal end of the implant, wherein, in a top view, the distal face and proximal end of the implant have complimentary shapes.

One aspect of the disclosure is a pin guide adapted for placing pin guides into an ilium and a sacrum in a dorsal approach.

In this aspect, the pin guide may include a pin guide body that includes at least one of a lateral ilium side with an axially extending ilium lumen and a lateral sacrum side with an axially extending sacrum lumen. If the pin guide body has first and second lumens, the lumens may be parallel.

In this aspect, an ilium side and an ilium lumen may extend further distally than a sacrum side and a sacrum lumen.

In this aspect, the pin guide may further comprise at least one lateral handle coupler that is adapted to be attached to an elongate handle so the handle and pin guide can be moved together by moving the handle.

In this aspect, the pin guide body may further comprise first and second central pins extending distally from the pin guide body, the first and second central pins disposed laterally inward relative to the ilium lumen and the sacrum lumen. Central pins may be permanently attached to a main portion of the pin guide body. Optional first and second central pins may be laterally aligned with each other. First and second central pins may extend between 10 mm and 20 mm from the pin guide body, optionally 15 mm.

One aspect of this disclosure is a pin guide adapted for placing pin guides into an ilium and a sacrum in a dorsal approach. The pin guide may include a pin guide body and a distal pin guide coupled to the guide body and extending distally from the pin guide body, wherein the distal pin guide may be movable relative to the pin guide body when the pin guide is in a first state and less movable relative to the pin guide body when the pin guide is in a second state.

One aspect of the disclosure is an impactor for advancing a bone implant. The impactor includes a proximal region, a distal region, and an elongate central region extending between the proximal region and the distal region.

In this aspect, the distal region may have a wafer configuration.

In this aspect, the distal region may include an implant securing element adapted to be releasable engaged with the bone implant.

In this aspect, the distal region may include a first protruding member on a first lateral side of the implant securing element and a second protruding member on a second lateral side of the implant securing element.

In this aspect, the distal region may include an ilium lumen in an ilium side of the distal region.

In this aspect, the distal region may include a sacrum lumen in a sacrum side of the distal region.

In this aspect, the distal region may include a distal face that is not orthogonal to a long axis of the central region. A distal face may extend further distally on the ilium side than on the sacrum side.

In this aspect, a first protruding member may extend further distally than a second protruding member.

In this aspect, an ilium lumen may extend further distally than a sacrum lumen.

BRIEF DESCRIPTION OF THE DRAWINGS

FIGS. 1A and 1B illustrate an exemplary SI joint implant engaged with a positioning guide.

FIGS. 18A, 18B and 18C illustrate an exemplary SI joint implant.

FIG. 19 illustrates an exemplary SI joint implant.

FIGS. 22A, 22B and 22C illustrate an exemplary SI joint implant.

FIGS. 29, 30 and 31 illustrate exemplary proximal ends of exemplary SI joint implants.

FIGS. 40, 41A and 41B illustrate radiographic imaging of an exemplary process that includes injecting contrast media through a needle that is placed in the SI joint.

FIGS. 56A, 56B, 56C and 56D illustrate exemplary pin guides.

FIGS. 59A, 59B, 59C, 59D, 59E and 59F illustrate an exemplary impactor.

FIGS. 63A, 63B and 63C illustrate an exemplary tool adapted for use with an impactor to remove pins from the patient.

DETAILED DESCRIPTION

The disclosure herein is related to SI joint stabilizing implants ("implants") and methods of implanting SI joint stabilizing implants across an SI joint from a dorsal approach. Methods herein include implanting an implant from a dorsal approach across the SI joint with a first portion of the implant positioned in the ilium, a second portion of the implant positioned in the sacrum, and a third portion (e.g., a central portion) placed across the SI joint. The implants herein may be sized and configured to be implanted utilizing any of the suitable methods of implantation and delivery tools herein, unless indicated herein to the contrary. Similarly, method of implantation and delivery tools herein may be used to deliver any or all of the suitably configured implants across an SI joint, unless indicated herein to the contrary.

A region or portion of the ilium into which a first portion of the implant is positioned from a dorsal approach may have greater density than a region or portion of the sacrum into which a second portion or region of the implant is positioned. When positioning a SI joint implant across a SI joint from a dorsal approach, the implant may thus tend to deflect away from denser cortical iliac bone and migrate towards and into the less dense sacrum, which can prevent proper positioning of the implant across the SI joint. Implantation methods, delivery tools and implants are described herein that can maintain proper implant trajectory when advancing the SI joint implant across the SI joint from a dorsal approach described herein. The methods and approaches herein can account for the differences in bone density between the ilium and sacrum and prevent the implant from migrating away from denser iliac bone during implantation. Additionally, implants herein are sized and configured to be safely implanted into a target anatomical region when implanted from the dorsal approaches herein.

Figure 32A:
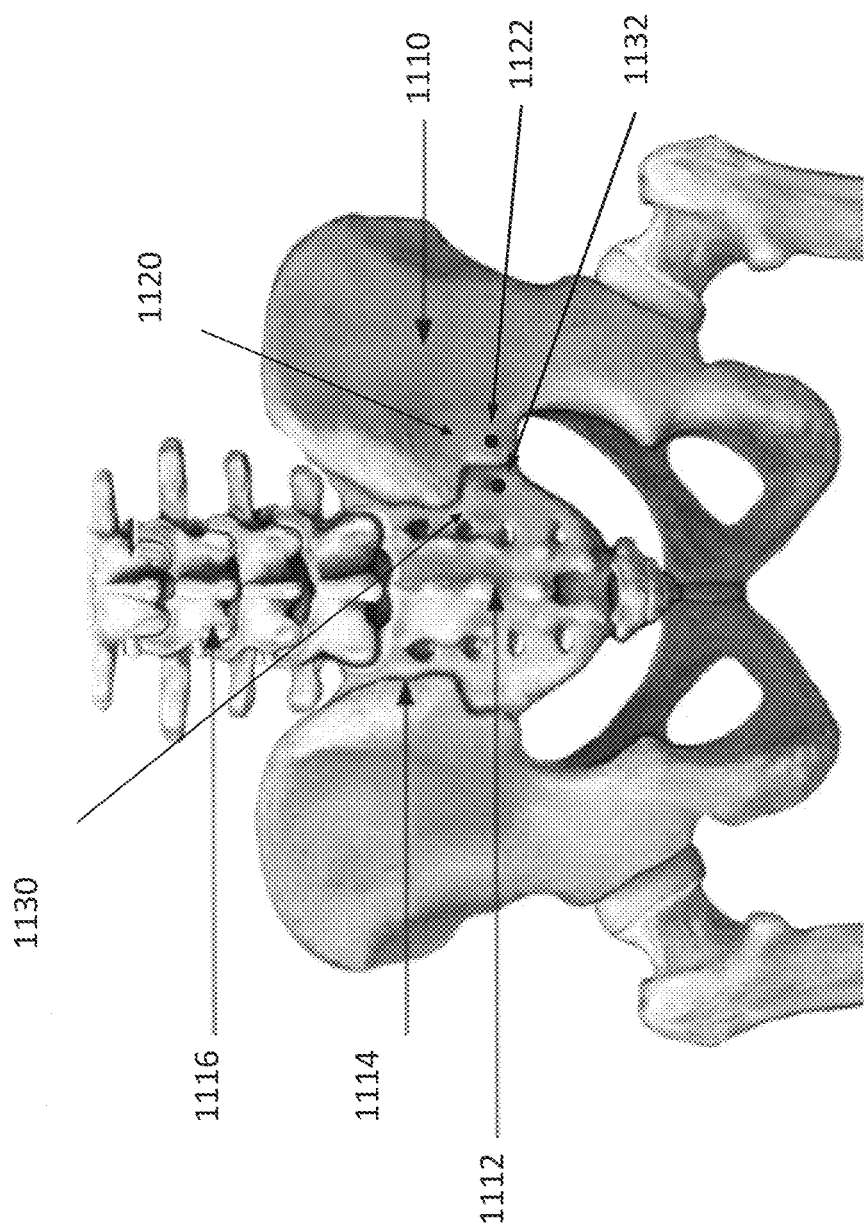
FIG. 32A illustrates a posterior view and exemplary locations for positioning guides.
Figure 32B:
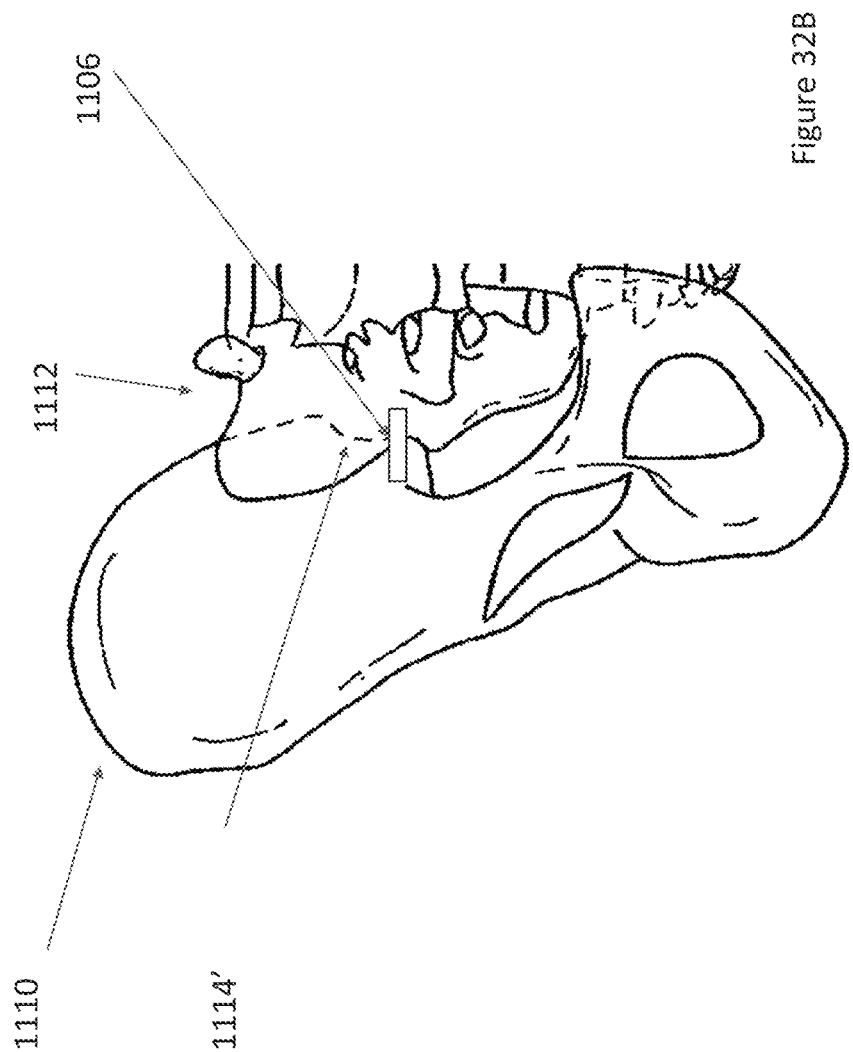
FIG. 32B illustrates an exemplary implantation location for a SI joint implant across a SI joint.

Methods of implanting the implants herein may include advancing one or more positioning guides, any of which may be referred to herein as a "guide," into an ilium from a dorsal approach, and in some embodiments between lateral and medial cortical walls of the ilium, which is described and shown herein. FIG. 32A illustrates a posterior view and a general dorsal approach for implanting the SI joint implants herein across an SI joint. FIG. 32B illustrates an exemplary implant 1106 that has been implanted across an SI joint 1114' with a first region or portion of the implant disposed in the ilium 1110, a second region or portion of the implant disposed in the sacrum 1112, and a central region or portion extending across the SI joint 1114'. FIGS. 32A and 32B, which are described in more detail below, illustrate ilium 1110, sacrum 1112, the SI joints 1114 and 1114', and lumbar vertebrae 1116. FIG. 32A also illustrates an optional anatomical region 1120 that is a starting point for advancing an ilium positioning guide into the ilium, and an optional exemplary anatomical region 1130 for a starting point for advancing a sacrum positioning guide into the ilium. FIG. 32A further illustrates an exemplary and optional ilium starting point 1122 for an ilium positioning guide, as well as an exemplary and optional sacrum starting point 1132 for a sacrum positioning guide. Any of the ilium positioning guides herein may have a starting point in ilium region 1120, such as ilium starting point 1122. Any of the sacrum positioning guides herein may have a starting point in sacrum region 1130, such as sacrum starting point 1132. A radiographic view image may be obtained and utilized to help guide the positioning guide into the ilium between lateral and medial cortical walls of the ilium, which are illustrated generally in FIGS. 32A and 32B. Methods herein may optionally include interfacing an ilium positioning guide herein with an ilium portion or region of the SI joint implant, such as an interface member of the implant, to guide the implant across the SI joint while maintaining a proper trajectory and achieving a desired implantation location. By positioning an ilium positioning guide in the relatively dense region of the ilium, and by interfacing and engaging the positioning guide with the ilium portion of the implant, the guide can help ensure a portion of or the entire implant will stay on course with a desired trajectory during advancement during implantation in the dorsal approach, rather than migrating away from the relatively dense cortical ilium bone and towards the sacrum. The optional positioning guides herein thus interface directly with the implant, and are sized and configured to act as a guide for the implant to ensure that an ilium portion or region of the implant is properly positioned in the ilium and that a joint region (which may be referred herein as a central region or portion) of the implant is properly implanted across the SI joint.

The positioning guides are sized and configured to, when engaged with the implant, generally restrict movement of the implant with respect to the positioning guide in at least one direction. The implant may be free to move relative to the positioning guide in other ways or directions. For example, once interfaced, the implant may still be able to rotate relative to the guide, such as in FIGS. 1A and 1B, but the guide can still maintain the desired trajectory (relative axial movement) of the implant when the implant is advanced in the dorsal trajectory with respect to the engaged guide.

The methods herein include advancing the implant across the SI joint, while the optional guide(s) helps guide an ilium portion of the implant into the ilium. The methods may also include removing the positioning guide from the ilium after the implant has been positioned across the SI joint.

The methods herein may include positioning more than one positioning guide, optionally more than one ilium guide in the ilium, and optionally one or more guides into sacral bone. Any of the one or more guides herein may be sized and configured to function as a positioning guide to help guide a portion of the implant into ilium bone or sacral bone.

In some alternative methods and implants described herein, the method of implantation may not require a position guide. For example, an implant may be advanced across an SI joint from a dorsal approach without using a positioning guide. For example, these methods may include radiographically visualizing a teardrop view of the ilium and advancing the implant while visualizing the teardrop view to ensure a portion of the implant stays sufficiently on course into the teardrop region of the ilium. Any of the methods herein may thus optionally exclude an ilium positioning guide, and may rely on a radiographic image, such as a teardrop view, to help maintain a desired implant trajectory into a teardrop region of the ilium. Implants implanted according to these methods may be implanted with or without a broach (described in more detail below), and if implanted without the use of a broach, the implants may have distal end regions that are configured to penetrate into bone, optionally having sharpened distal ends.

Some of the implants herein, such as any of those shown in FIGS. 1A-31, are generally sized and configured to be able to interface with an elongate ilium positioning guide, and may be sized and configured to interface with one or more additional positioning guides, which may be ilium or sacrum guides.

Exemplary implants are described below. Even if the textual description of an exemplary implant does not expressly include it, it is understood that features shown with respect to different exemplary implants may be incorporated into other exemplary implants. For example, the implants shown in FIGS. 1A, 1B, 2A and 2B each have an interface member with an annular inner surface that defines a lumen, even if the text does not expressly include a description thereof. Additionally, similar components may be similarly labeled in different embodiments. For example, it is understood that references to elements 10, 20, 30, 40, etc., in some of the figures may illustrate systems, even if the text related to any particular embodiment is silent with reference to a reference number shown in the figure.

FIG. 1A is an end dorsal view (showing the proximal portion) and FIG. 1B is a perspective view of exemplary system 10 that includes SI joint stabilizing implant 14 and elongate ilium guide 12. Implant 14 includes an ilium guide interface member 18 interfacing, which may be also referred to herein as engaging, with ilium guide 12. Implant 14 includes main body or implant body 16, a central portion or region of which is disposed across the SI joint when the implant is implanted. The interface member 18 includes a surface 19 that has a configuration, in this example annular, that is sized and configured to interface with the corresponding configuration of ilium guide 12 to allow implant 14 to be axially advanced relative to guide 12. In these figures, the guide may or may not already be positioned in an ilium, such as at the exemplary general location shown in FIG. 32A. The interface between the guide and the interface member of the implant restricts the movement of the implant interface guide member with respect to the ilium guide in one or more directions. In this example, implant 14 may still be rotated relative to guide 12, but the interface restricts, for example, side-to-side (lateral) movement of 14 implant relative to guide 12. In this embodiment, the guide has a cylindrical configuration, with an annular outer profile in cross section along almost all of its length (except for the distal tip region, which may be configured to penetrate and/or anchor (temporarily) into bone). Any of the guides herein may have a cylindrical configuration along all or substantially all of its length. Any of the guides herein may also include a sharpened or pointed distal end (e.g., as shown in FIGS. 1B, 2B, 3B), which may be configured to help penetrate and/or anchor into bone (temporarily), such as iliac bone and/or sacral bone.

Figure 10:
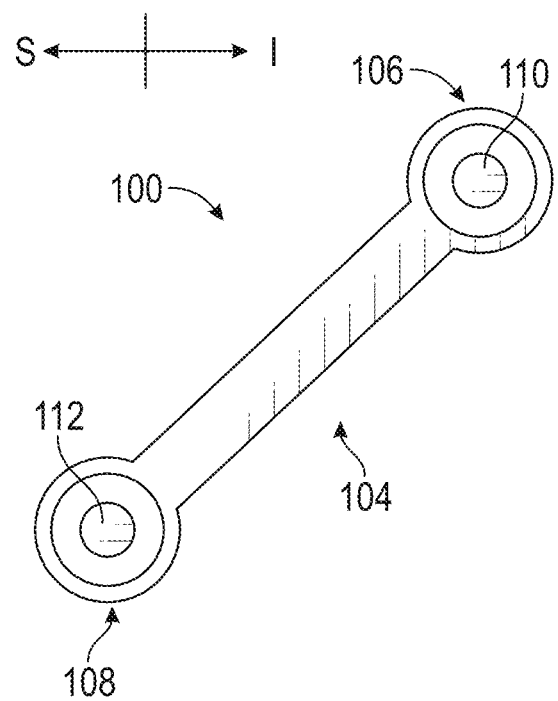
FIG. 10 illustrates an exemplary SI joint implant engaged with a plurality of positioning guides.
Figure 11:
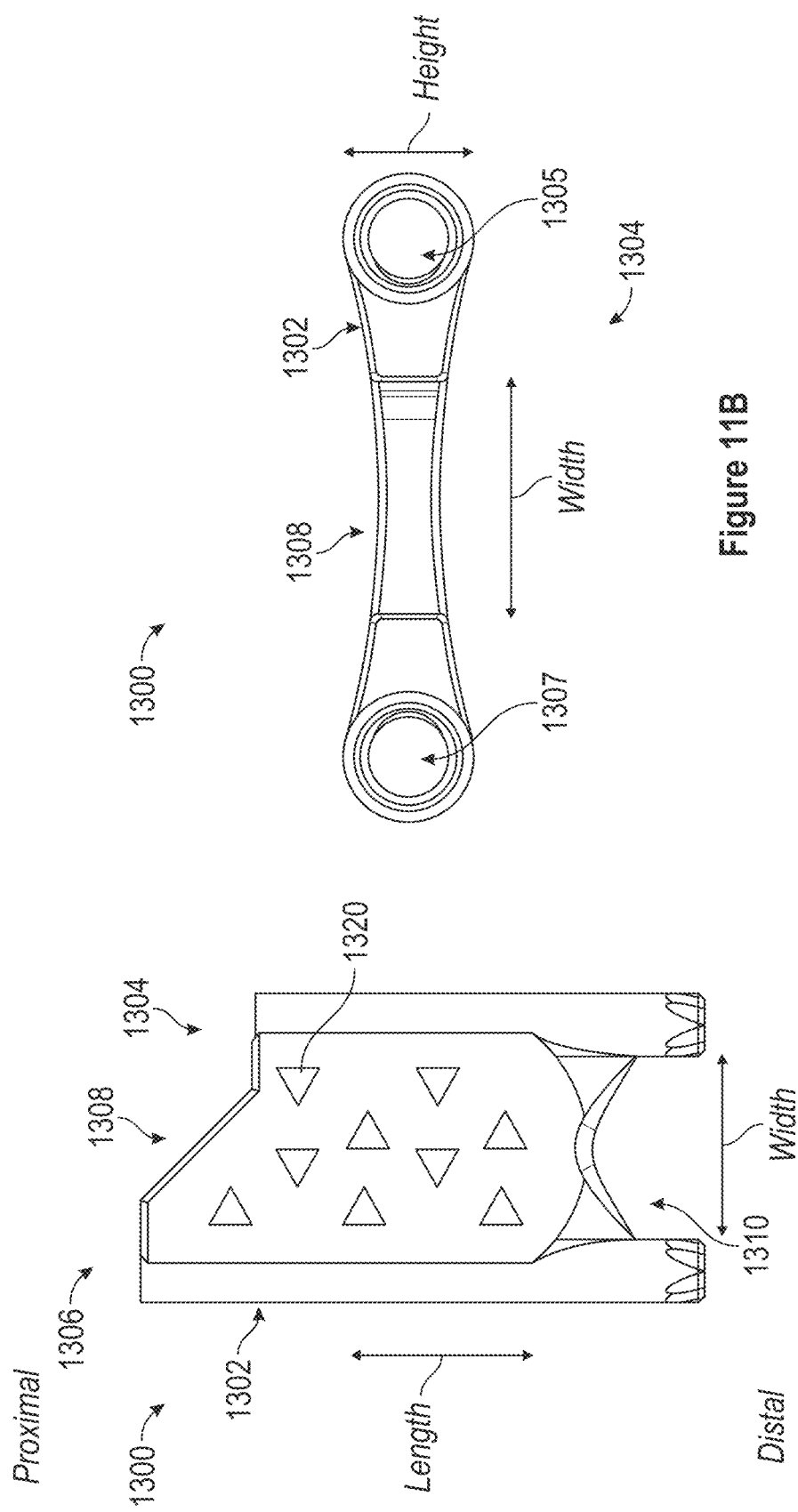
FIGS. 11A and 11B illustrate an exemplary SI joint implant.

In figures herein, including FIGS. 1A and 10, "S" refers to a sacrum and "I" refers to an ilium.

Figure 2A:
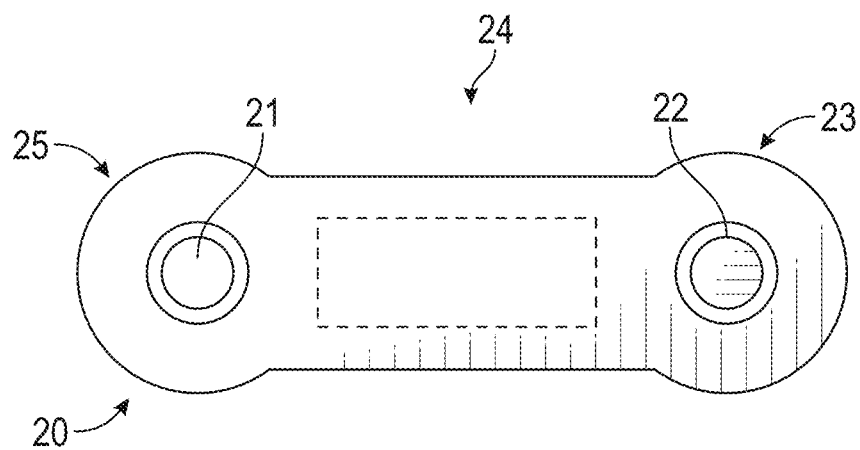
FIGS. 2A and 2B illustrate an exemplary SI joint implant engaged with first and second positioning guides.
Figure 2B:
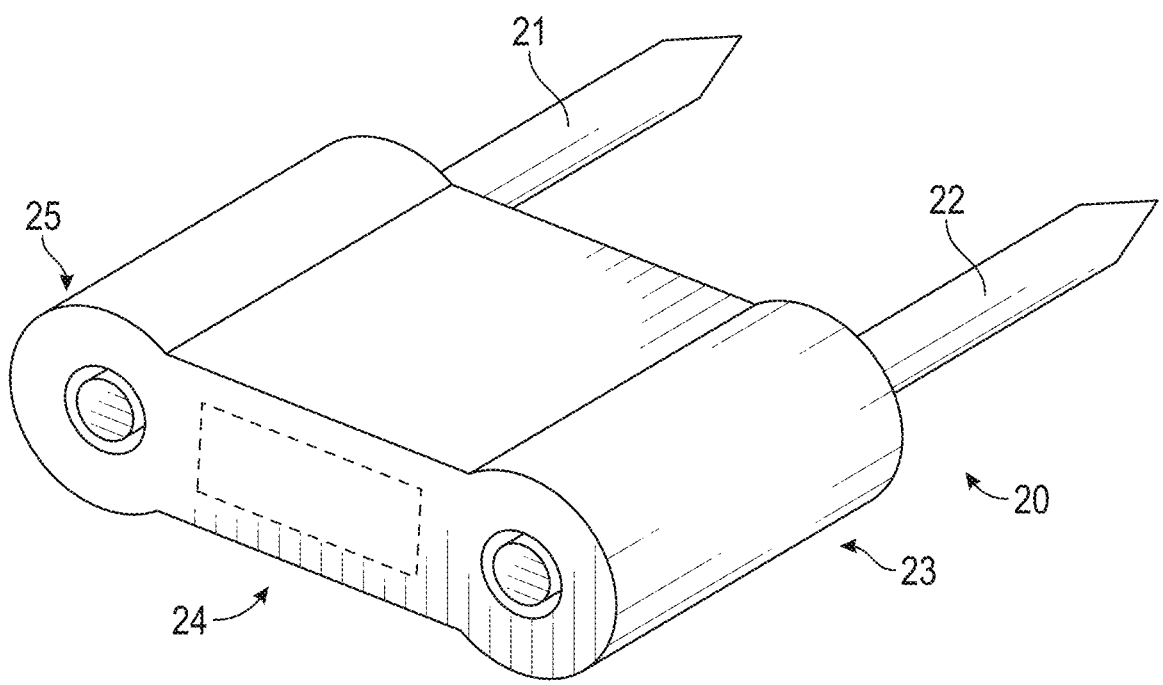

FIGS. 2A (end view) and 2B (perspective) illustrate exemplary system 20, which includes implant 24, ilium or iliac guide 22, and an optional elongate sacrum or sacral guide 21. In the figures shown, ilium guide 22 and the sacrum guide 21 may or may not yet be positioned within the ilium and sacrum, respectively. In some methods, the one or more guides may be inserted into bone, and then the implant may be advanced over the guides. In some embodiments, the implant is interfaced with the one or more guides, and subsequently the one or more guides can be inserted into bone. Interfacing the implant to a plurality of guides (in examples with more than one guide) before guide insertion may help prevent the guides from being inserted into bone and spaced apart at positions that prevent the implant from then be interfaced with the guides and successfully advanced along the guides and across the SI joint. Interfacing the implant with the guides first may help the guides being properly spaced apart to accommodate the implant during implantation. In merely exemplary embodiments herein, a method may include inserting an ilium guide into iliac bone, interfacing the guide with the implant, interfacing the implant with a sacrum guide, and inserting the sacrum guide into a sacrum. The implant may subsequently be advanced across the SI joint.

Any of the dashed lines in FIGS. 1A, 2A, 3A and 4A in an implant body indicates an optional axially extending bore or opening within a body portion of the implant, which may extend through distal and proximal implant body surfaces.

Figure 3A:
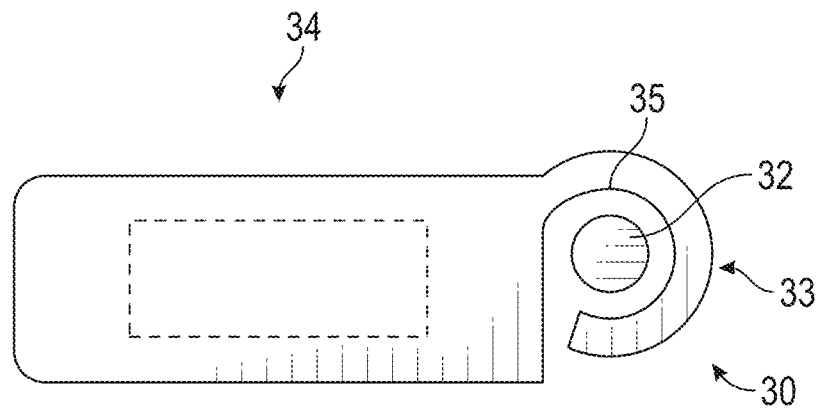
FIGS. 3A and 3B illustrate an exemplary SI joint implant engaged with a positioning guide.
Figure 3B:
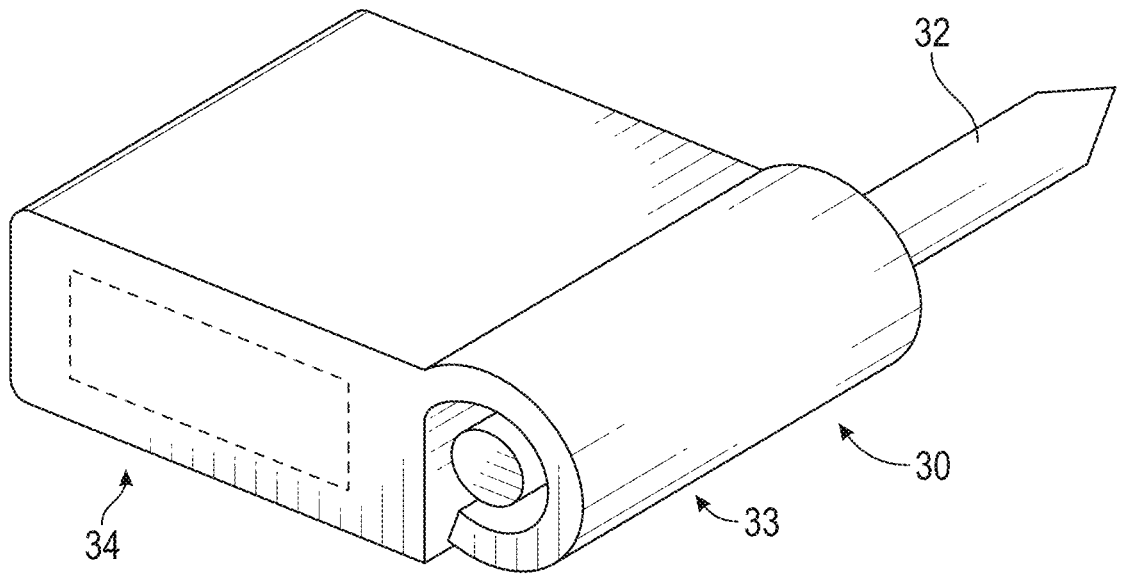

FIGS. 3A (end view) and 3B (perspective view) illustrate an exemplary system 30 that includes implant 34, which is configured to interface with ilium guide 32. Implant 34 includes guide interface member 33 that has a surface 35 sized and configured to interface with guide 32, which may be an ilium guide. Member 33 is in this embodiment curvilinear and has an almost completely annular configuration, but extends less than 360 degrees.

Figure 4A:
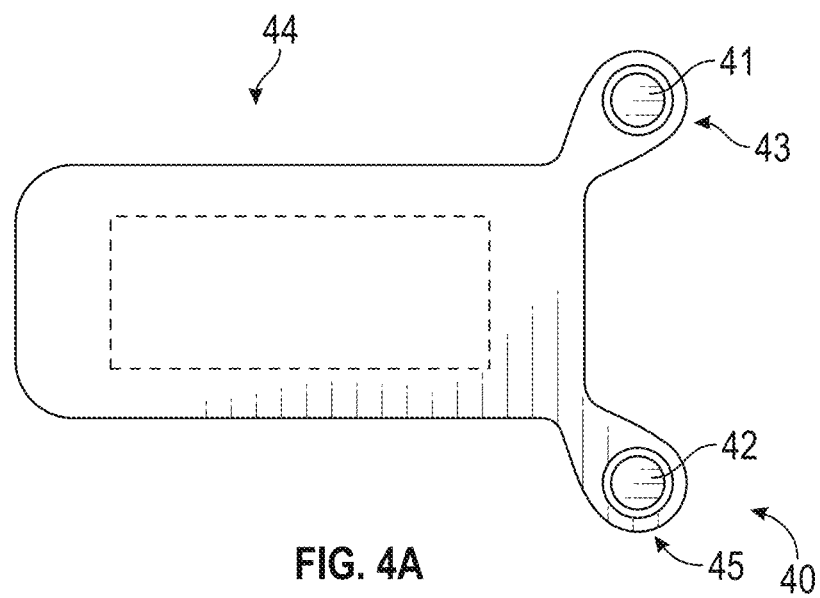
FIGS. 4A and 4B illustrate an exemplary SI joint implant engaged with first and second positioning guides.
Figure 4B:
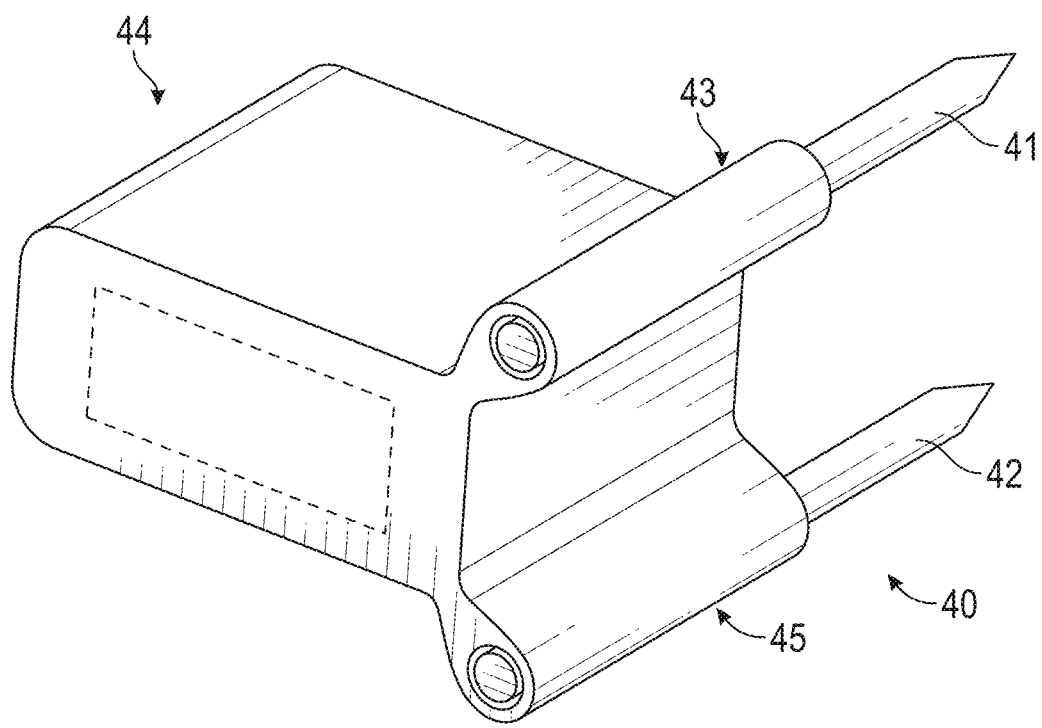

FIGS. 4A (end view) and 4B (perspective view) illustrate exemplary system 40 that includes implant 44 with first and second ilium guide interface members 43 and 45, each of which has a surface configured to interface with ilium guide 41 and ilium guide 42, respectively. Members 43 and 45 in this embodiment extend upward and downward from the main body region further than the guide interface members in FIGS. 1A, 1B, 2A and 2B, for example.

Figure 5A:
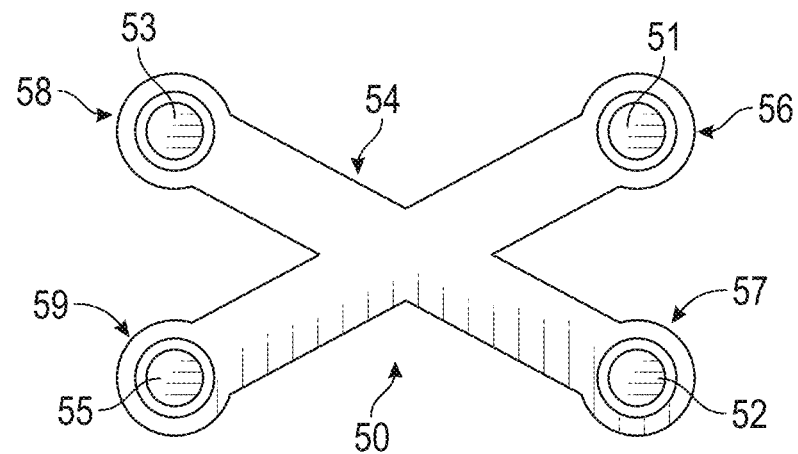
FIGS. 5A and 5B illustrate an exemplary SI joint implant engaged with a plurality of positioning guides.
Figure 5B:
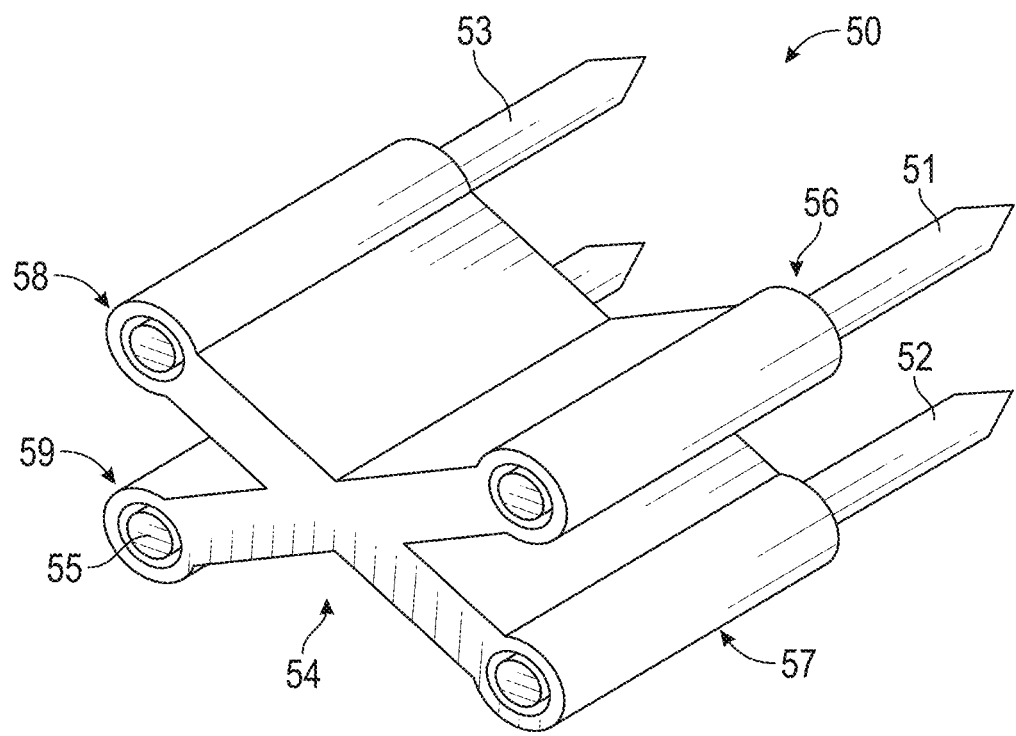

FIGS. 5A (end view) and 5B (perspective view) illustrate an exemplary system 50 that includes exemplary implant 54, and exemplary ilium guides 51 and 52 and sacral guides 53 and 55. Implant 54 includes four guide members 56, 57, 58 and 59, each configured to interface with and be axially moveable relative to a separate guide. The implant body has a general "X" or crossing configuration in an end view, but could have other configurations, such as square, rectangular, oval, etc., and may still have four (or more) guide interface members.

Figure 6A:
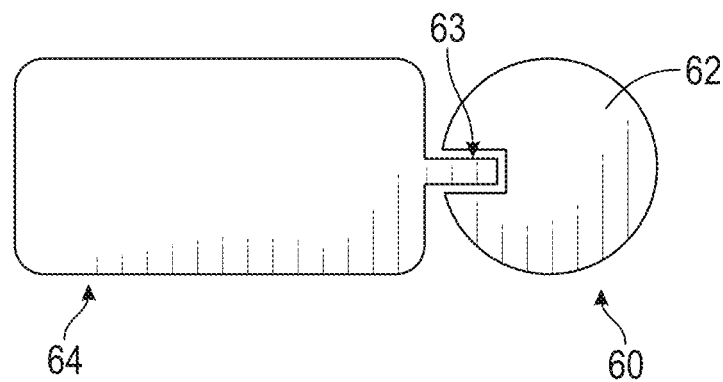
FIGS. 6A and 6B illustrate an exemplary SI joint implant engaged with a positioning guide.
Figure 6B:
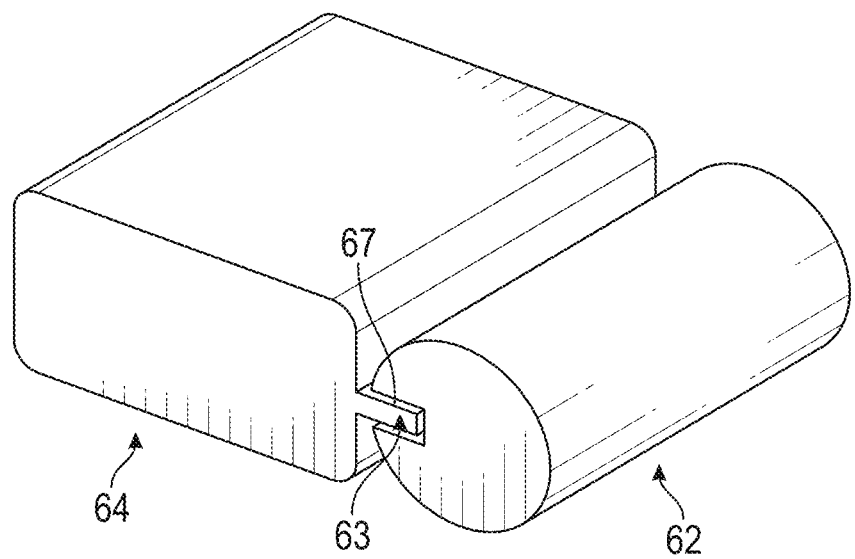

FIGS. 6A (end view) and 6B (perspective view) illustrate an exemplary system 60 that includes implant 64 configured to interface with guide 62. In this embodiment guide 62 includes a recessed region that is configured to stably interface with interface member 63 that in this example is a lateral protrusion or extension from a main body region of the implant. This is an example of the implant having a guide interface member that extends within a portion of the guide, compared with guide interface members that extend around a portion of the guide, such as is shown in FIGS. 1A-5B. The interface in this embodiment limits up and down movement of the implant relative to the guide, as well as right lateral movement relative to the guide, but allows guide 62 to act as a guide for implant 64 during implantation.

Figure 7:
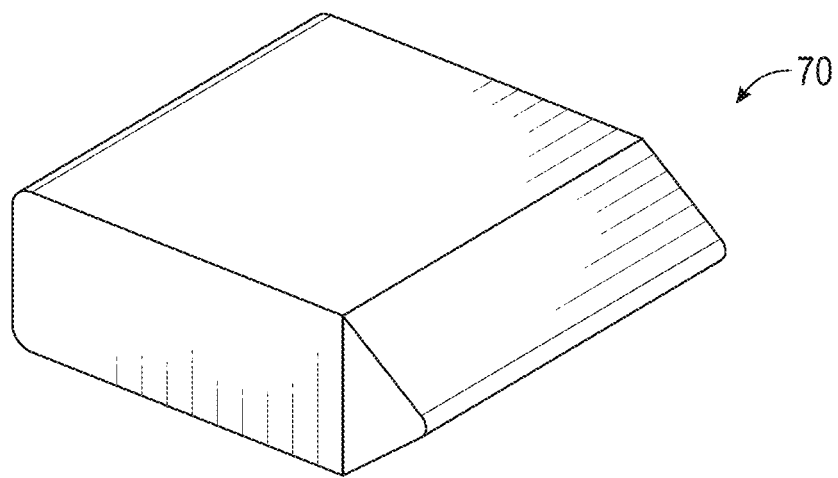
FIG. 7 illustrates an exemplary SI joint implant.

FIG. 7 illustrates an exemplary implant 70 or broach 70 with a sharpened distal end, in this example extending laterally across the entire or substantially the entire width of the implant body, as shown. If used as a broach, the broach 70 may be configured with any of the guide members herein, and in methods of use can be guided over one or more guides (before the implant is implanted) to create a space across the SI joint for the implant. The broach can be removed, and an implant can then be advanced over the guides, which is described in more detail below.

If used as an implant, the implant 70 may comprise any of the guide members herein (e.g., one or more lumens), and in methods of use can be guided over one or more guides to position the implant across an SI joint. The sharpened region of the implant may create a space for the implant by penetrating or cutting into bone.

Figure 8:
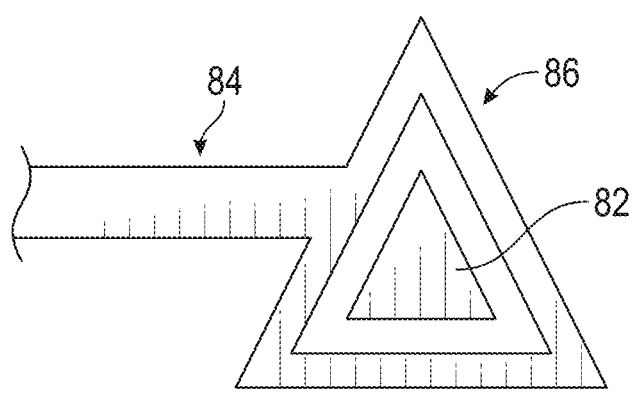
FIG. 8 illustrates a portion of an exemplary SI joint implant engaged with a positioning guide.

FIG. 8 (end view) illustrates an exemplary implant 84 that includes guide interface member 86, which is configured to interface with guide 82. In this exemplary embodiment, guide 82 has a triangular configuration (which may have other rectilinear configurations), and member 86 includes an inner surface triangular configuration (which may have other rectilinear configurations), as shown. Implant 84 may also have any number of members 86, each of which can be configured to interface with a different guide.

Any of the implants herein may also have a guide interface member with a first configuration and a second guide interface member with a second configuration different than the first. For example, any of the implants herein may have one or more interface members that are the same or similar to member 23, the same or similar to member 33, the same or similar to member 63, and/or the same or similar to members 86.

Figure 9:
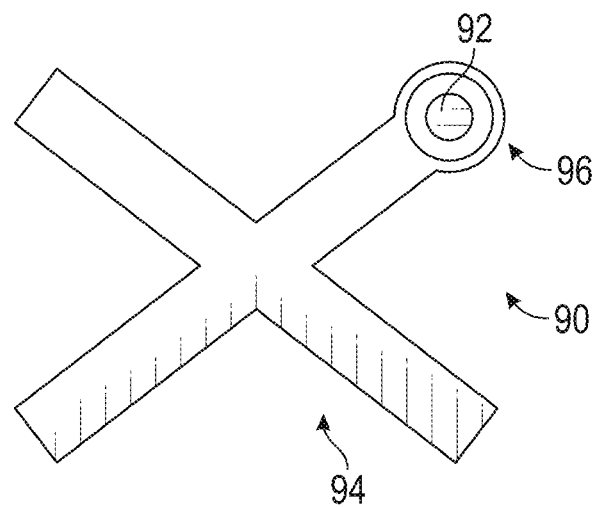
FIG. 9 illustrates a portion of an exemplary SI joint implant engaged with a positioning guide.

FIG. 9 (end view) illustrates an exemplary system 90 that includes implant 94. Implant 94 has a plurality of arms, and not all of the arms include a guide interface member at the respective arm end region. In this embodiment, only one of the arms has a guide interface member (in this embodiment member 96), but in other embodiments the implant may have any number of members less than the number of arms extending from a main body portion (e.g., two, three, four, etc.).

FIG. 10 (end view) illustrates an exemplary system 100 that includes an implant 104 that includes ilium guide interface member 106 and sacrum guide interface member 108, each of which is configured to interface with guides 110 and 112, respectively. The position shown illustrates the implant as it may be implanted across an SI joint, illustrating that any of the implants herein may be implanted with one guide member (e.g., 106) in one type of bone superior to another guide member in a different type of bone (e.g., ilium versus sacrum). For example, guide 110 may be positioned in iliac bone, and guide 112 may be positioned in a sacrum, either inferior to guide 110 as shown, or in other embodiments superior to guide 110, which is not shown, but which would be above guide 110 in FIG. 10.

Any of the implants herein may have one or more surfaces that are configured and adapted to facilitate at least one of bony ingrowth and ongrowth. For example, without limitation, any of the implants herein may include one or more of fenestrations, apertures, porous surfaces, irregular surfaces, etc., such as any that may be described in U.S. Pat. No. 9,044,321, U.S. Published Application 2013/0296953, U.S. Pat. Nos. 9,662,157, 10,166,033, U.S. Published Application 2016/0287171, the disclosures of which are incorporated by reference herein for all purposes.

As is set forth herein, SI joint implants herein may include one or more interface members, which may be configured as axially extending lumens or bores, and which may also be referred to as channels herein. The interface members are generally sized and configured to accommodate relative movement of one or more guides (such as an ilium guide), which are positioned in an ilium or a sacrum. In this way, implants may be moved axially relative to and guided by the positioning guides to the intended implantation location across the SI joint without migrating (or at least minimizing migration) away from the denser iliac bone.

In some embodiments, the implant may include interface members that are in opposing lateral side regions of the implant, an example of which is shown in FIGS. 2A and 2B. In this arrangement, the implant is advanced over the guides to position the implant across the SI joint. The guides may be removed after the SI joint implant is delivered to its desired position, leaving the implant implanted across the SI joint.

FIGS. 11A and 11B illustrate in top and back end views, respectively, exemplary implant 1300. Implant 1300 may include any of the suitable features of other implants herein, such as interfacing members configured to interface with a positioning guide. FIGS. 11A and 11B illustrate implant 1300, which is sized and configured for implantation across a SI joint from a dorsal approach. Implant 1300 includes implant body 1302 that includes an ilium region or portion 1304 that is sized and configured for implanting into an ilium when the implant is implanted across a SI joint from the dorsal approach. Implant body 1302 also includes a sacrum region or portion 1306 that is sized and configured for implanting into a sacrum when the implant is implanted across the SI joint from the dorsal approach.

Height, Width and Length directions of the implant are also labeled to provide the relative dimensions of the implant body that are described herein. When the description herein refers to a general dimension (e.g., height, length) of the implant body, it refers to the greatest dimension of the implant body. For example, with reference to FIG. 11B, if the disclosure refers to a Height of implant body 1302, it refers to the greatest height dimension of the implant body, which in this embodiment is in lateral regions of the implant body. The disclosure herein may also, however, refer to dimension in a particular region of the implant (e.g., central region Height). The relative Distal and Proximal directions are also labeled in FIG. 11A.

Figure 33:
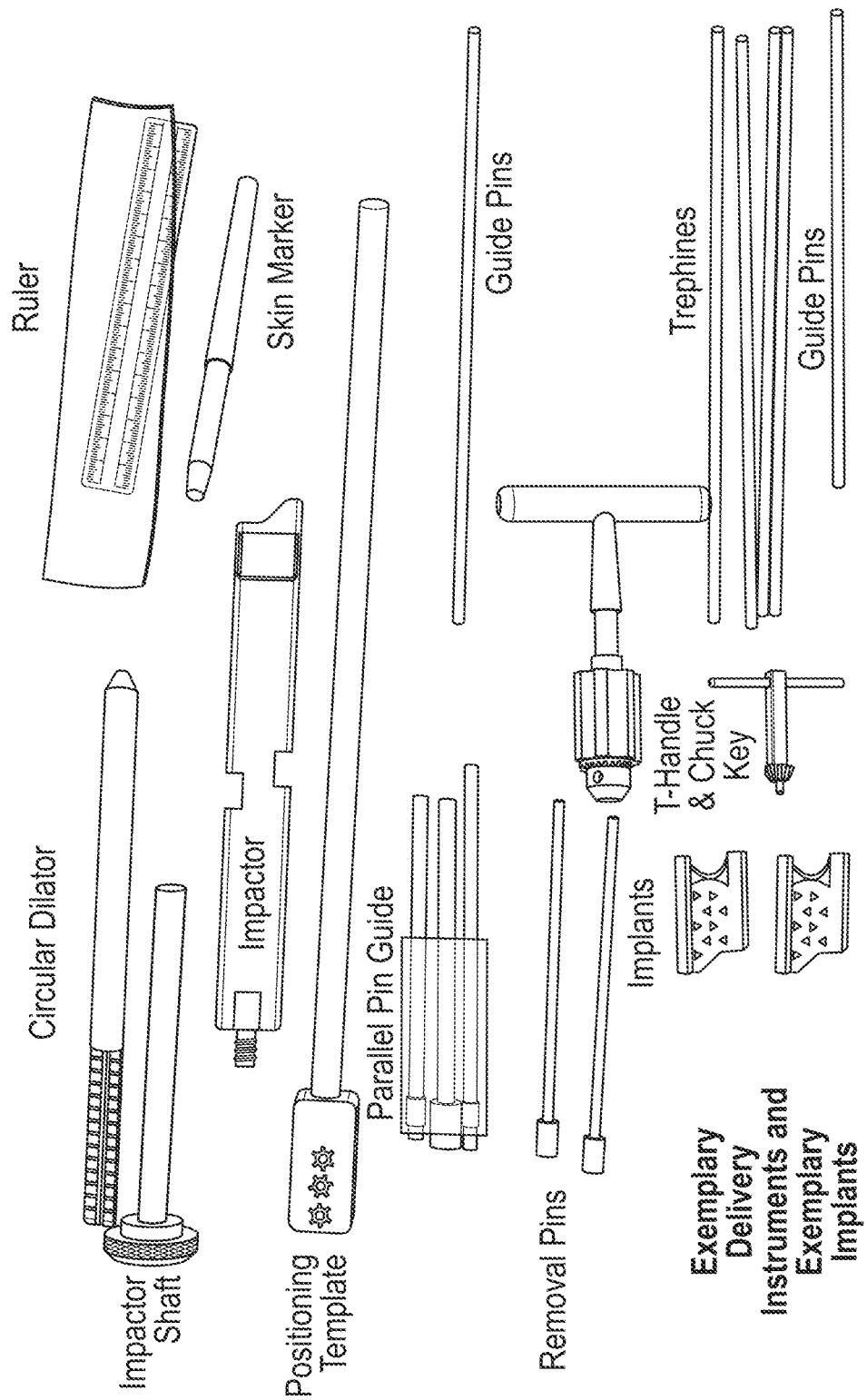
FIG. 33 illustrates exemplary tools adapted for positioning one or more pins and for delivering implants from a dorsal approach.
Figure 36:
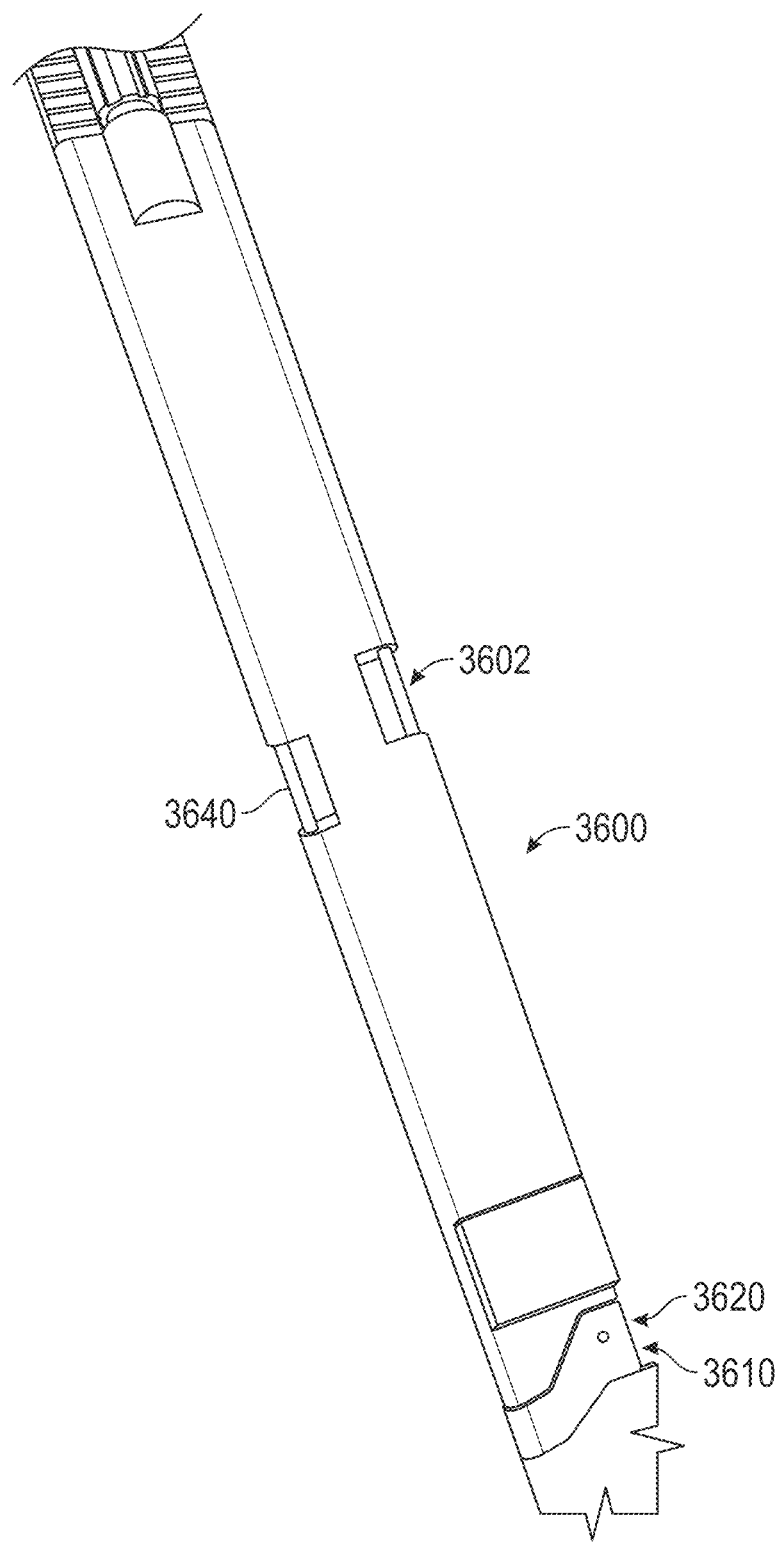
FIG. 36 illustrates an exemplary impactor that is secured to an exemplary implant.
Figure 38:
FIG. 38 illustrates an illustrative SI joint, ilium and sacrum.
Figure 39B:
FIGS. 39A, 39B, 39C and 39D illustrate exemplary 2D spaces characteristic of exemplary target envelopes.
Figure 39A:

As shown, ilium region 1304 includes and defines elongate ilium lumen 1305 therein that extends from a distal opening to a proximal opening, and is sized and configured to receive therein an ilium positioning guide. In this example, sacrum region 1306 extends further proximally than the ilium region 1304 with reference to the Length direction, as shown in FIG. 11A. FIG. 38 illustrates an illustrative SI joint 1800, ilium 1802, and sacrum 1804. Implants herein may be advanced from a dorsal approach and into position across the SI joint, with the ilium region or portion of the implant in the ilium and the sacrum region or portion in the sacrum. The overall implant dimensions and configuration of exemplary implant 1300 (which may also be referred to herein as the implant outer profile) may provide one or more advantages when implanting the implant across the SI joint from the dorsal approaches described herein. As can be seen in FIGS. 38, 39A and 39B, the sacrum may extend further proximally than the ilium, relative to the delivery trajectory. With implants that have an ilium region that extends as far proximally as a sacrum region, the ilium region of the implants may extend too far posteriorly when implanted, such that they are extending out of the ilium. Ilium region 1304 does not extend as far proximally as sacrum region 1306, such that when implanted there is less risk that the ilium region 1304 will extend outside of the ilium. The proximal end of the implant body in this example includes optional stepped region or portion 1308 between a sacral side and an ilium side of the implant body 1302, and in this example optionally includes three flat surfaces (shown in the top view of FIG. 11A), the central of which is tapered and extends further distally in the ilium portion of implant body. The tapered surface in this example extends between proximal sacrum and ilium surfaces that are orthogonal to a long axis of the implant (as shown), and are described in more detail with respect to an impactor, an example of which is shown in FIGS. 33 and 36. In alternative implants, the proximal end may be a combination of one or more flat or curved surfaces, additional examples of which are described below.

Alternatively, implant 1300 may have a distal end in which ilium region 1304 extends further distally than sacrum region 1306, some examples of which are described below. For example, the configuration of implant body 1302 may approximate a general parallelogram shape that does not comprise four right angles, such as a rhomboid or rhombus configuration (in a top view of the implant). Implants for which sacrum regions do not extend as far distally as the ilium region may provide an advantage of preventing the sacrum region 1306 from being advanced too far distally in the patient, which may mitigate a risk of damaging tissue distal to the desired implantation location. Some implants herein thus may have ilium and sacrum regions that do not extend as far proximally or as far distally as one another, which may provide the exemplary advantages set forth herein.

Implant body 1302 is an example of an implant body that has a height dimension that is less than a width dimension, as shown. Implant body 1302 also includes a sacrum region 1306 that includes an optional elongate sacrum lumen 1307 therein that extends from a distal opening to a proximal opening and is sized and configured to receive therein a sacrum positioning guide (such as any of the sacrum guides herein). In this example, sacrum lumen 1307 has a length that is greater than a length of ilium lumen 1305, but in alternatives in which the sacrum region does not extend as far distally as is shown in FIG. 11A, the lumens may have lengths that are the same or substantially the same. In this example, sacrum lumen 1307 is parallel to the ilium lumen 1305. The term parallel in this disclosure can include a very minor deviation from being strictly parallel, such as lumens or sides with corresponding axes that intersect at an angle that is five degrees or less, for example. Ilium lumen 1305 is also parallel to a longitudinal ("long") axis of the implant body, with the long axis in this example extending in the length direction.

Figure 39D:
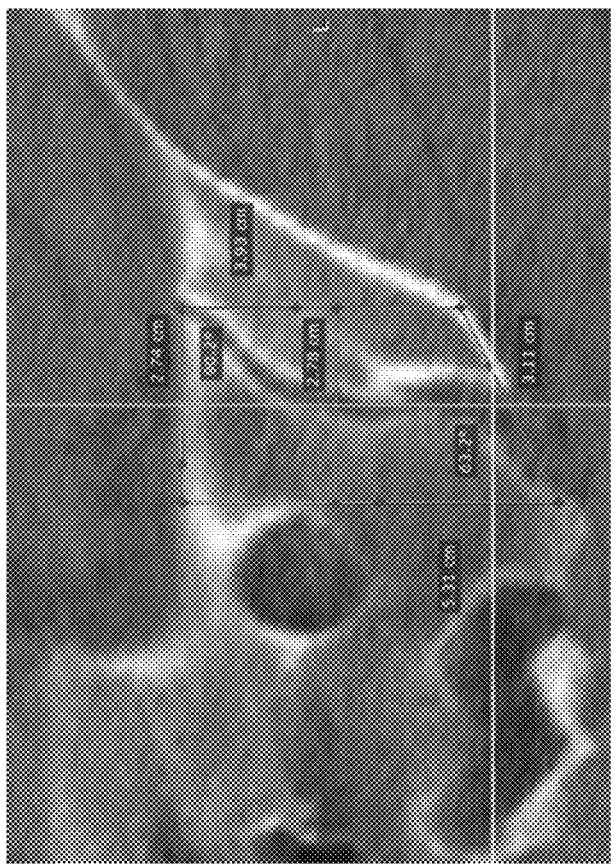
Figure 39C:
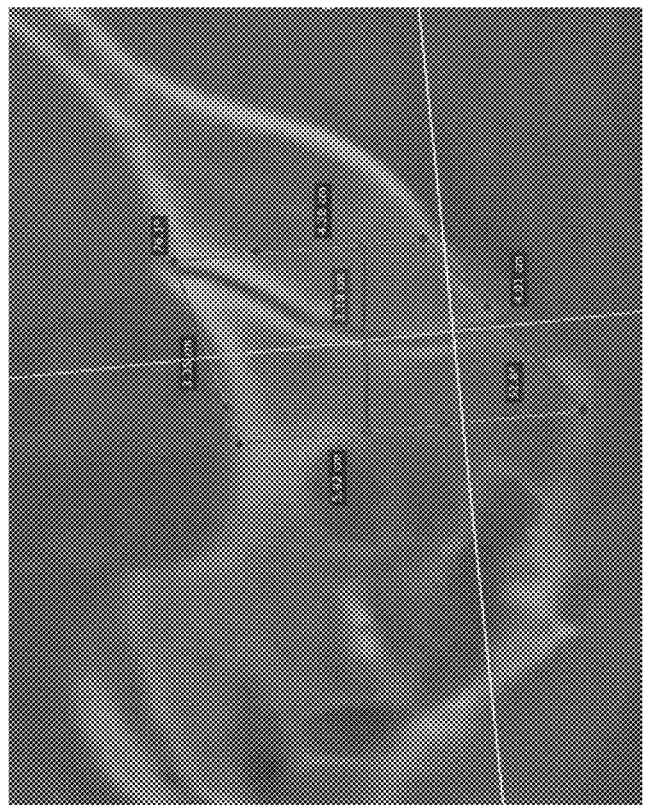

As is set forth herein, the outer profile of the implant body is important to ensure the implant is positioned at a target implant location and generally within a patient's target anatomical envelope. A target envelope refers generally to an anatomical volume that is the target location for the implant, which may vary from patient to patient due to anatomical variability. For example, some implant configurations mitigate a risk of extending too far proximally out of the ilium, as described above. Additionally, some implant outer profiles may mitigate a risk of extending too far distally, such as too far distally in the sacrum and potentially damaging sensitive tissue. As such, the implant body generally has dimensions and profiles sized and configured to avoid these potential problems. The target envelope may optionally be characterized by two dimensional (2D) spaces and/or a three dimensional (3D) space. FIGS. 39A, 39B, 39C and 39D illustrate exemplary views that illustrate exemplary 2D spaces with exemplary dimensions that partially characterize exemplary target envelopes. As shown, there can be some patient-to-patient variability in sacral bone shape, iliac bone shape, and SI joint shape. While some implant shapes herein may be able to treat a wide range of patients, it may optionally be beneficial to customize an SI joint implant for a particular patient, such as by customization of one or more dimensions (e.g. angles), and/or the outer profile of the implant. A customization process can include characterizing the target envelope, such as obtaining one or more 2D views (e.g., FIGS. 39A-3D) and/or constructing a 3D image of the target envelope, and designing or selecting an implant (optionally from a kit of implants with at least some different dimensions and/or outer profiles, for example) based on the target envelope characterization. For example, a patient from which the image in FIG. 39D is obtained may optionally be treated with an implant herein where ilium regions and sacrum regions extend to the same distal extent (e.g., FIGS. 11A, 24, 25, 26 or 28A and 28B), whereas a patient from which the image in FIG. 39B is obtained may optionally be treated with an implant with a configuration that more closely approximates the general rhomboid 2D space annotated in FIG. 39D, such as (without limitation) any of the implants in FIG. 14, 15A, 16, 18A, or 23A).

Figure 14:
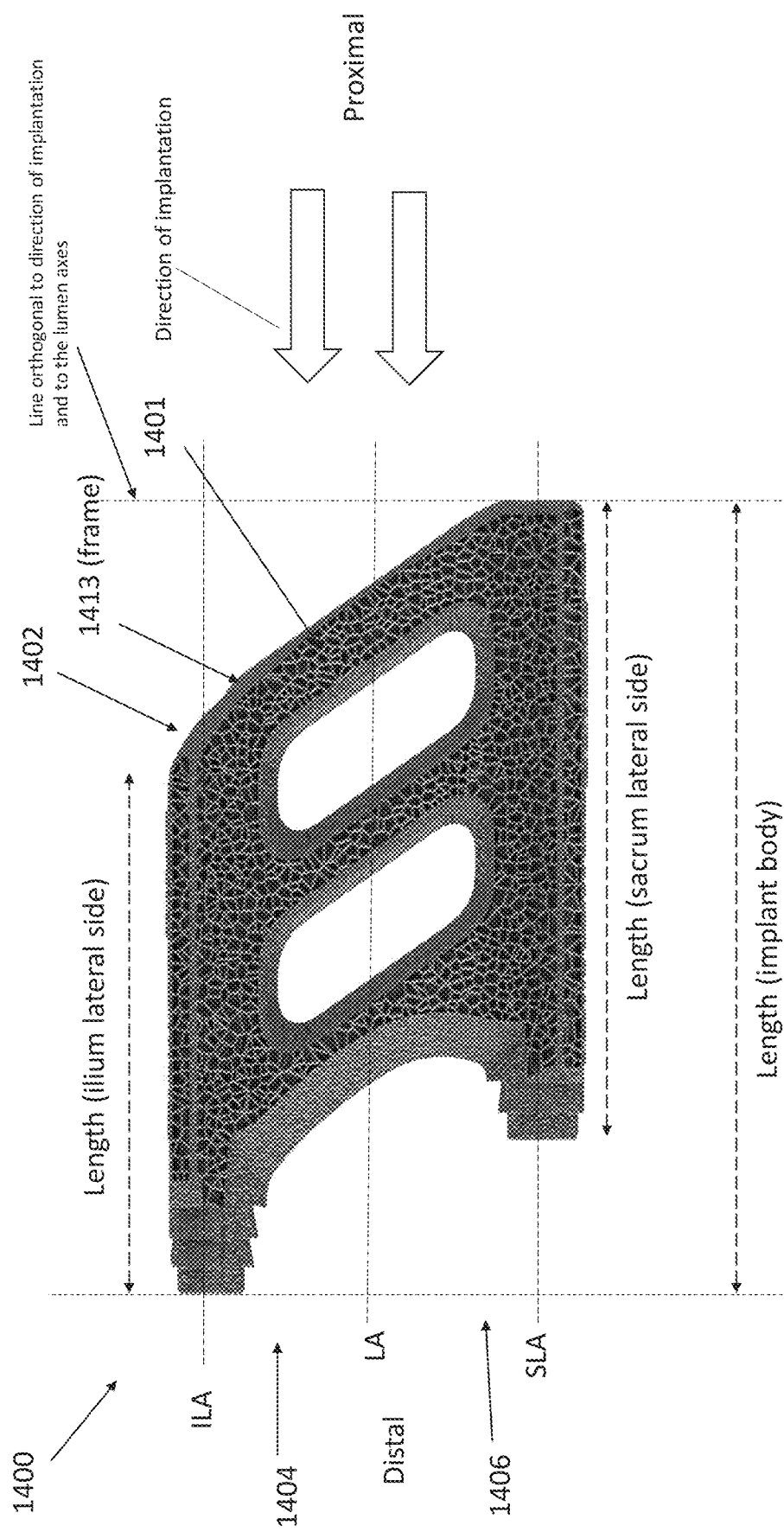
FIG. 14 illustrates an exemplary SI joint implant.
Figure 16:
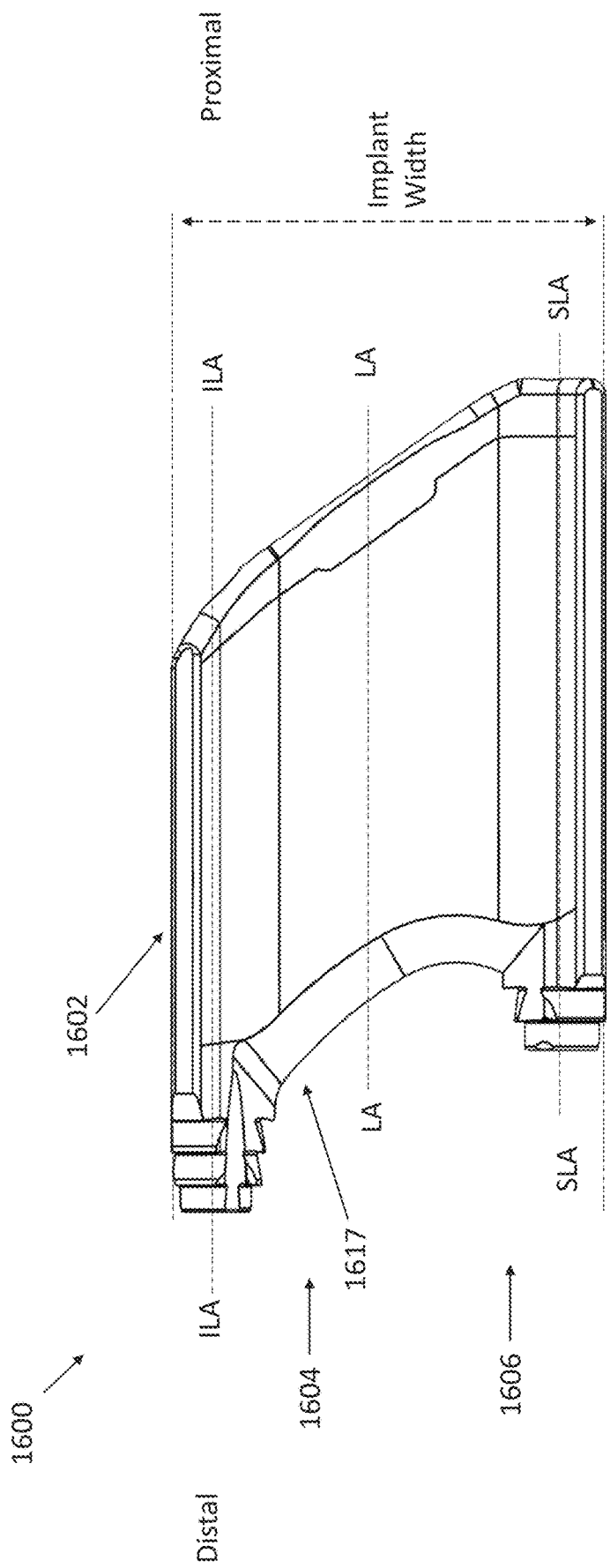
FIG. 16 illustrates an exemplary SI joint implant.

The implant bodies herein may have a length from 15 mm to 80 mm (an example length of which is shown in FIG. 14, as "Length (implant body)"). For example, in FIG. 11A, the greatest proximal extent of implant body 1302 is in sacrum region 1306, and the greatest distal extent of implant body 1302 is in both sacrum region 1306 and ilium region 1304. In any of the embodiments herein, the ilium lateral side of the implant body may have a length from 35 mm to 70 mm, an exemplary dimension of which is shown in FIG. 14 as "Length (ilium lateral side)." In any of the embodiments herein, the sacrum lateral side may have a length from 25 mm to 60 mm. In any of the embodiments herein, the implant body may have a width from 15 mm to 50 mm, as example of which is shown in FIG. 16 ("Implant Width"). In any of the embodiments herein, the implant body may have a height from 4 mm to 15 mm in at least a portion of the implant (such as one or both of an ilium region or a sacrum region), and the height may also vary across the width of the implant body, an example of which is shown in FIG. 11B.

Figure 28:
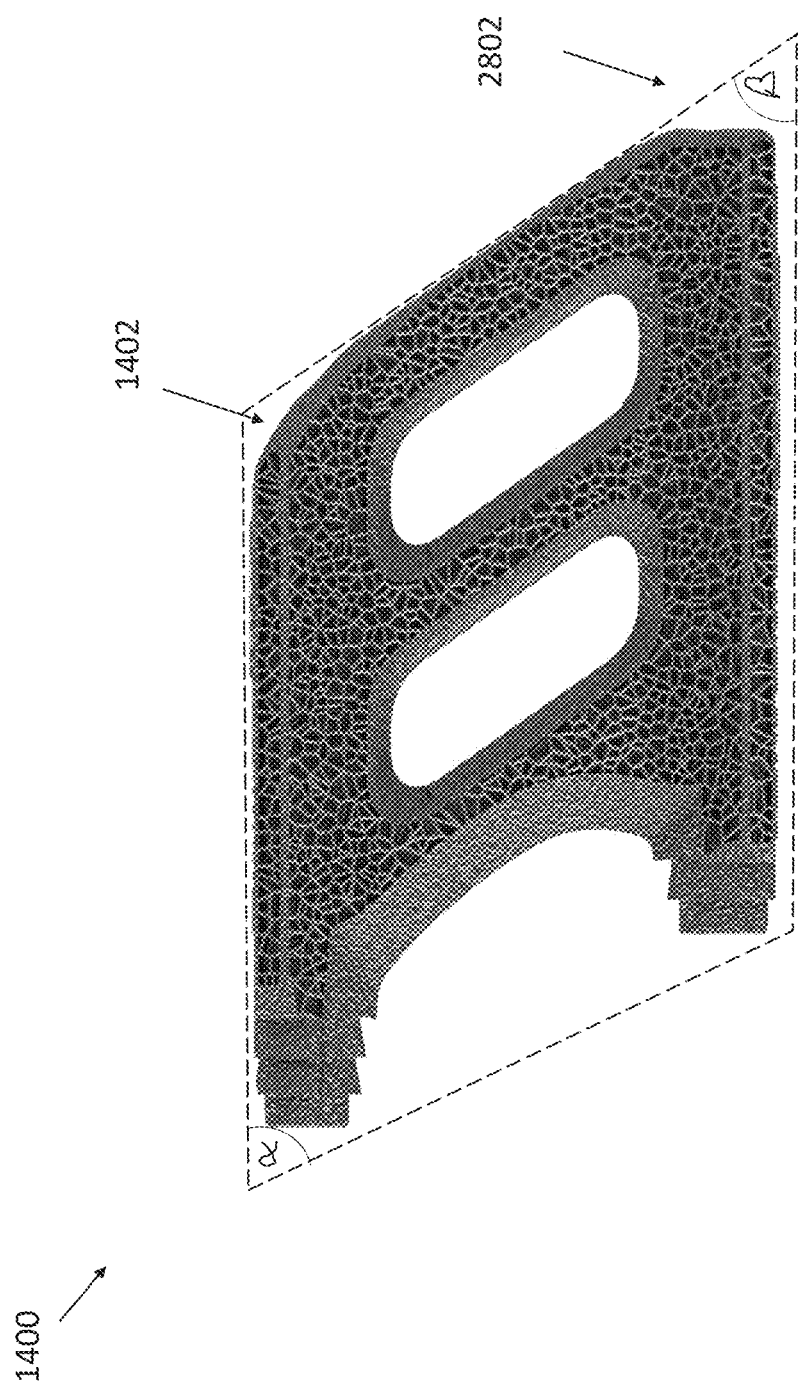
FIG. 28 illustrates an exemplary SI joint implant and an approximated quadrilateral shape or configuration of the implant in a top view of the implant body.

FIG. 28 illustrates an approximated shape of the implant body in a top view, including angles beta (the angle between the proximal end and the sacrum side of the approximated shape) and alpha (the angle between the ilium side and the distal or front end of the approximated shape). FIGS. 39A-39D also include exemplary angles alpha and beta for exemplary envelopes for particular patients. In some embodiments, the implant and/or the approximated shape (an example of which is shown in FIG. 28) may have an angle beta from 30 degrees to 85 degrees, including any subrange therein. In some more particular embodiments, the angle beta may be from 35 degrees to 80 degrees. In some embodiments, the angle alpha may be from 30 degrees to 90 degrees. The angle alpha may be slightly greater than 90 degrees (e.g., 90.2 degrees) and still be considered to be within the range from 30 degrees to 90 degrees, including any subrange therein. In some particular embodiments, angle alpha may be from 40 degrees to 90 degrees. It is understood that implants herein may have one or more right angles, such as having a rectangular shape in the top view (e.g., square). For example, some implants may be modified such that angles alpha and beta are 90 degrees. Any of the implants herein (including in any claims) may have any of the exemplary angles alpha and beta described herein.

The implant configuration may also be characterized by a top and/or bottom surface area of the implant, such as is shown in the top view of FIG. 11A. The surface area may refer generally to an area of an outer profile of the configuration of the implant (in a top view), even if there are a plurality of openings 1320 extending through the implant body (examples of which are shown in FIG. 13A). In any of the embodiments herein, a surface area of a top portion and/or a bottom portion of the implant body may be from 400 to 3,000 mm².

As mentioned above, in some non-limiting embodiments the implant body have a quadrilateral configuration, such as a parallelogram configuration without right angles (e.g., rhomboid or rhombus), with the ilium portion extending further distally than the sacrum portion, and the sacrum portion extending further proximally than the ilium portion, many examples of which are shown and described herein.

Figure 24:
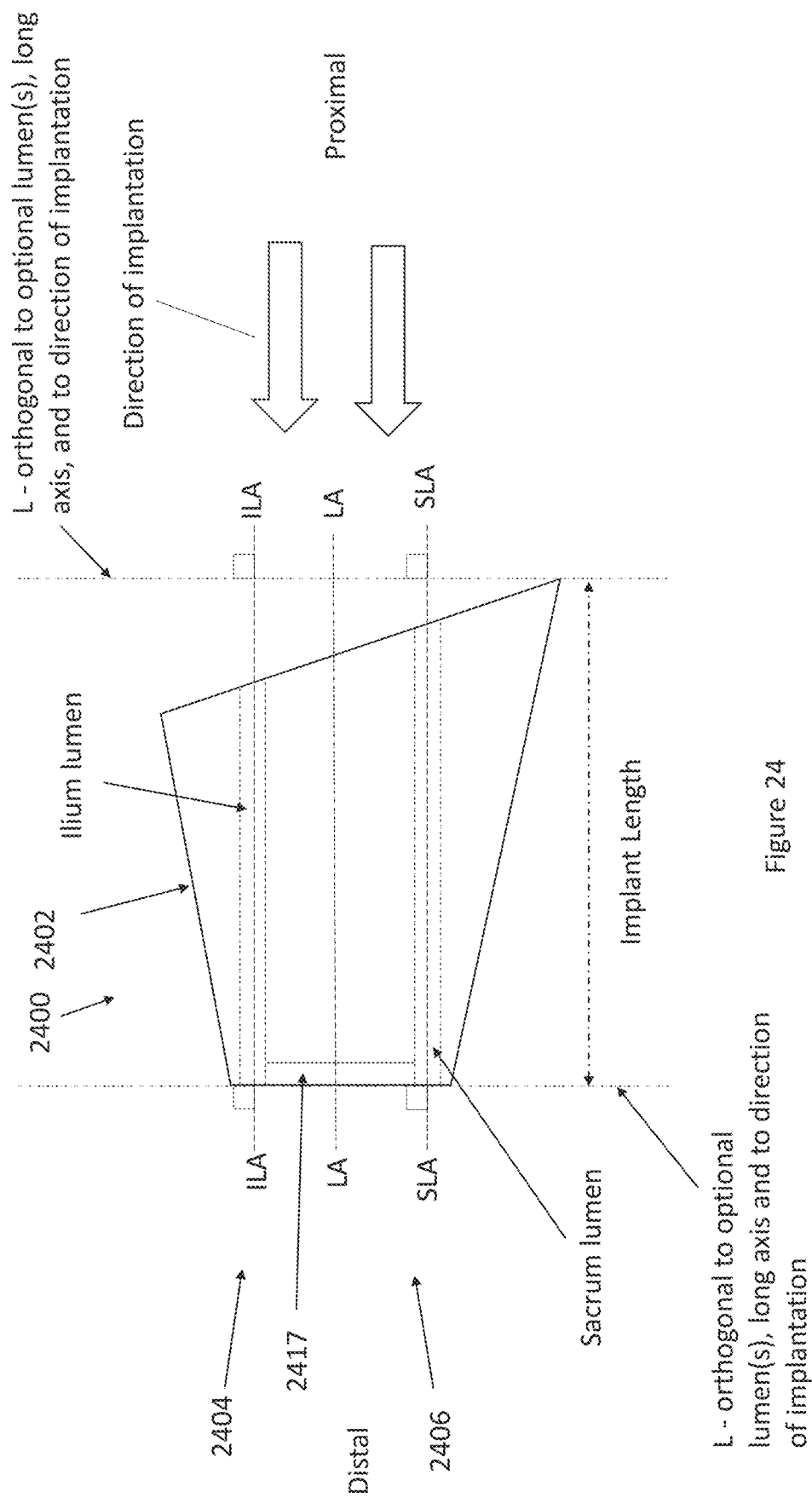
FIG. 24 illustrates an exemplary SI joint implant.
Figure 25:
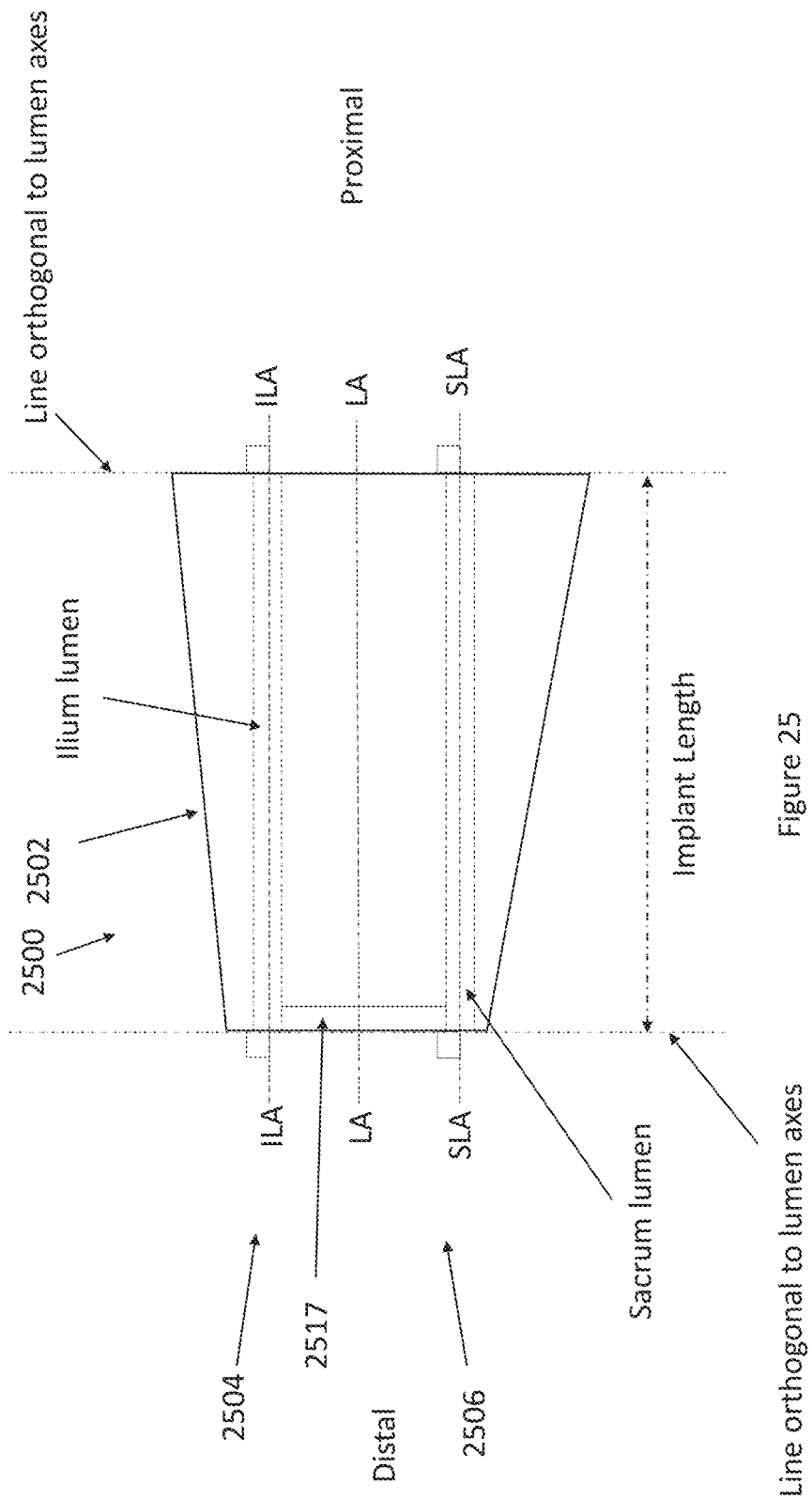
FIG. 25 illustrates an exemplary SI joint implant.
Figure 26:
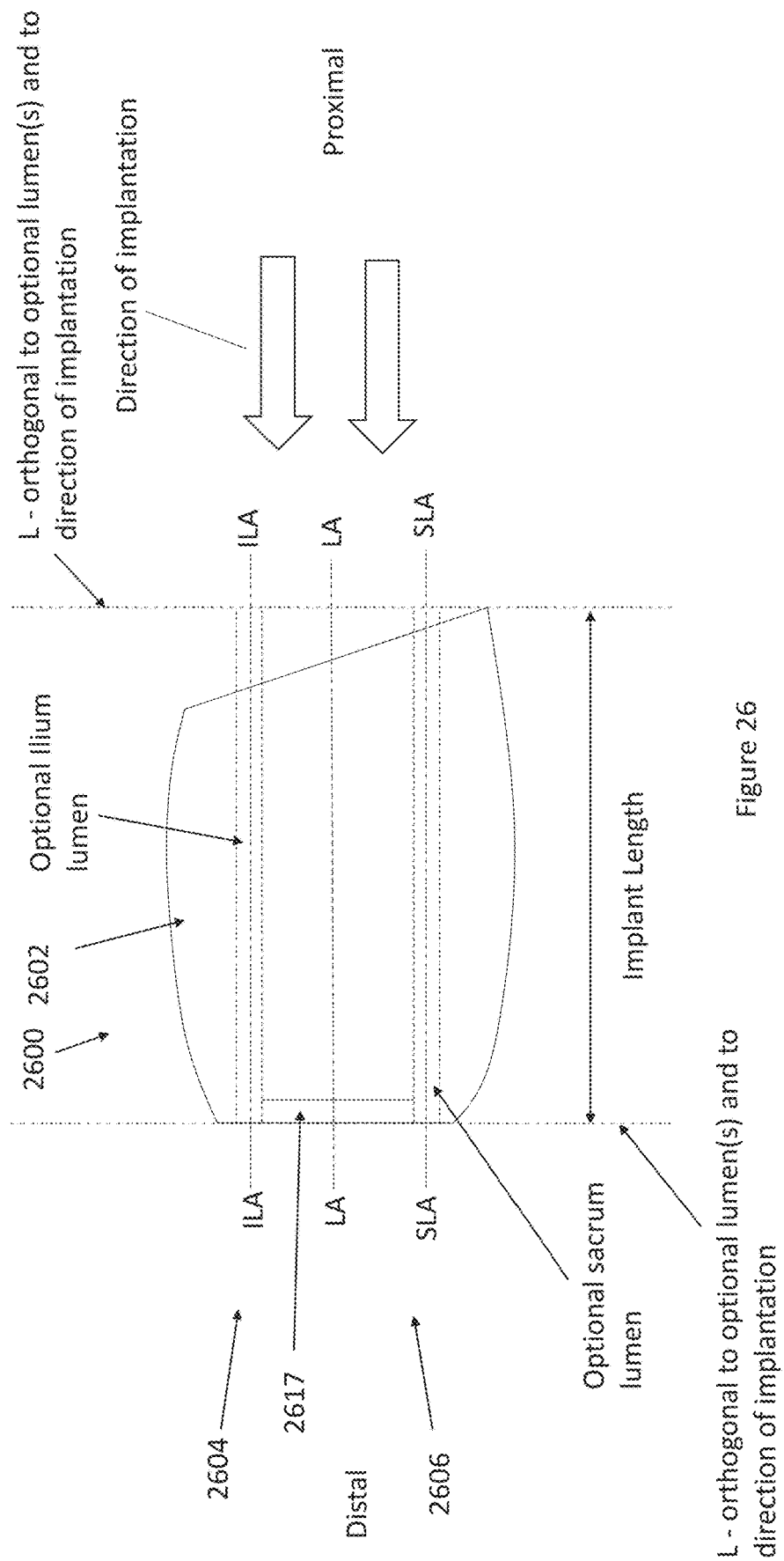
FIG. 26 illustrates an exemplary SI joint implant.
Figure 27:
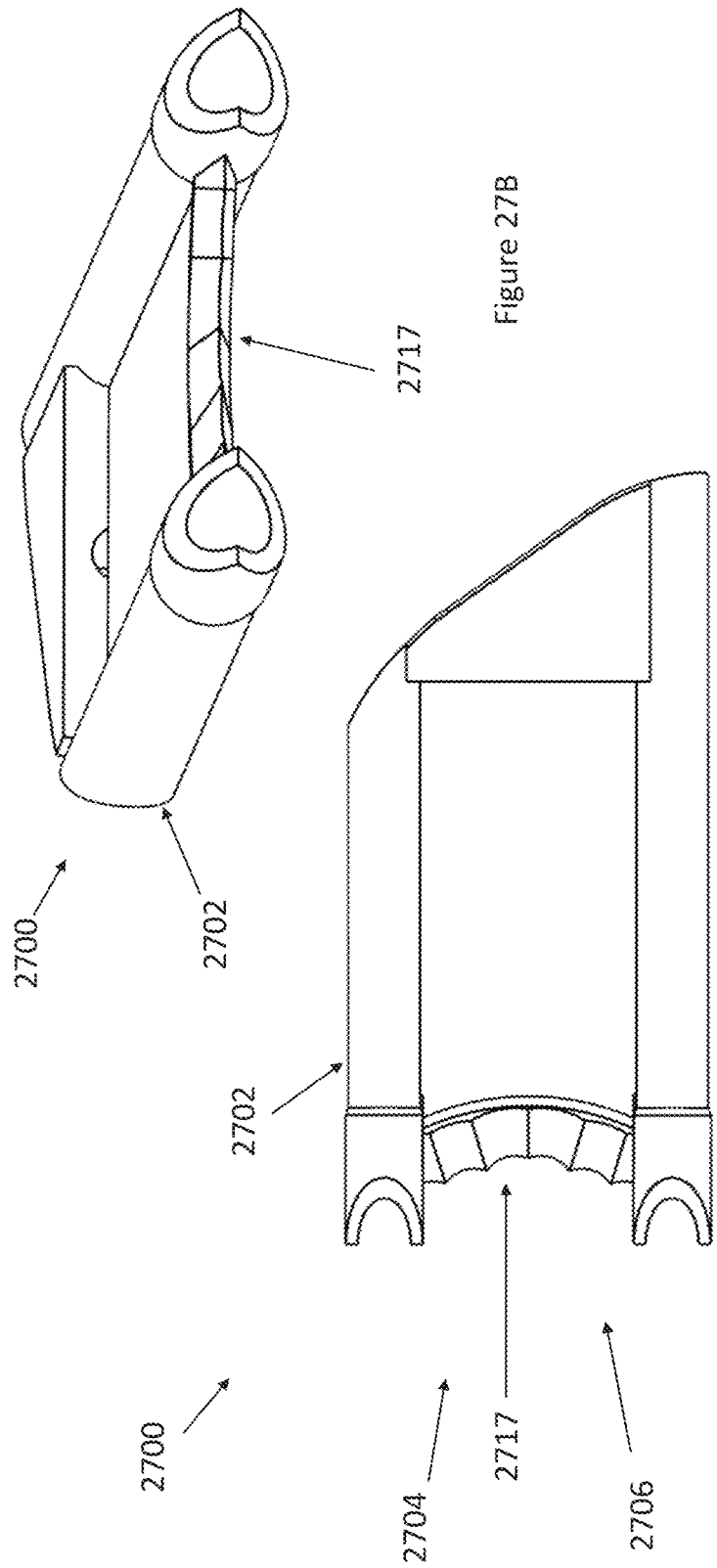
FIGS. 27A and 27B illustrate an exemplary SI joint implant.

In some embodiments, the implant body may have a quadrilateral shape (in a top view) with one or more right angles, such as a rectangle or square. For example, an implant body herein may have a rectangular shape with a sharpened distal region, an example of which is shown with implant 70 shown in FIG. 7. FIGS. 24-26 illustrate exemplary implant bodies with a quadrilateral shape or configuration, without any right angles.

As shown in FIG. 11B, implant body 1302 optionally has a height that is not constant across a width of the implant. In this example, the height is greater in at least a portion of the ilium and sacrum portions than in the central portion. The top and bottom portions or surfaces of the implant bodies herein may have a gradual curvature therein in an end view, as shown in the example in FIG. 11B.

As used herein, an implant body that has a wafer configuration or profile refers to an implant body with a width dimension that is greater than a height dimension. Implant body 1302 is an example of an implant body that has a wafer or wafer-like configuration. The height dimension of any implant body herein may be not more than 70% of a width dimension of the implant body, not more than 65%, not more than 60%, not more than 55%, not more than 50%, not more than 45%, not more than 40%, not more than 35%, not more than 30%, not more than 25%, not more than 20%, not more than 15%, or not more than 10% of the implant body width. Implants herein are implanted across an SI joint from a dorsal approach, and if the implant body height is too great, the implant body may undesirably extend outside of the joint when implanted.

Wafer implants herein, may however, have relatively larger heights than those described in the ranges herein (absolute and/or relative) and may be able to safely stabilize and/or fuse an SI joint. For example, the implant bodies herein may be able to safely stabilize the SI Joint even if the height dimension is, for example, not more than 80% of the width dimension.

Implant body 1302 is also an example of a SI joint implant body wherein the ilium lateral side of the implant body has a length that is different than a length of the sacrum lateral side of the implant body. In this example, the ilium lateral side is shorter than the length of the sacrum lateral side, as shown. The lengths of the lateral sides in this context refers to the lengths of the lateral sides of the implant body, example of which are shown in FIG. 14 as "Length (ilium lateral side," and "Length (sacrum lateral side")."

Implant body 1302 also includes a distal end region 1310 (which in this example is not the furthest distal extent of the entire implant body) that is sized and configured for one or more of penetrating through bony tissue as the implant is advanced or reducing the likelihood that the implant deviates from the intended trajectory. For example, distal end region 1310 is an example of a sharpened distal end at least a portion of which extends laterally inward or centrally relative to lateral sides of the implant, the sharpened distal end configured to help penetrate or cut through bony tissue as the implant is advanced. Additionally, end region 1310 has an optional concave curved configuration that can reduce the likelihood that the implant deviates from its intended trajectory when being distally advanced during implantation. A concave curved configuration (an example of which is shown in the top view of FIG. 11A) may be thought of as helping self-center the implant across the SI joint as the implant is being advanced. The degree of curvature may vary along the curve, as is shown in the example of FIG. 11A. The curve may be symmetrical about a long axis of the implant (even if the degree of curvature varies), of the curve may be asymmetrical about a long axis of the implant (such as if the ilium and sacrum regions have distal ends that do not extend distally to the same point, examples of which are described below). The sharpened distal end in this example has a tapered configuration, as shown, with a first surface tapering downward and distally from a top portion or surface of the implant body, and a second surface tapering upward and distally from a bottom portion or surface of the implant body, as shown. A sharpened region as that phrase is used herein does not require a configuration with a knife's edge, but rather may be a region with surfaces that taper towards one another or other configurations that facilitate cut or penetrating through bony tissue.

In this example, the sacrum and ilium lateral sides of the implant body extend further distally than distal region 1310 (distal region 1310 includes a central region of implant body), but in other embodiments the sacrum lateral side may not extend further distally than distal region 1310. The curvature of region 1310, in a top view, may optionally be symmetrical about a long axis of the implant body (such as is shown in the example in FIG. 11A), which may help maintaining the implant trajectory. Distal end region 1310 also extends laterally across a central region of the implant, wherein the central region is laterally inward relative to lateral sides of the implant body. A long axis of the implant body may extend through sharpened distal end region 1310.

Implant distal region 1310 is an example of a front region of the implant that has at least one surface sized and configured to at least help maintain the implant trajectory when implanted across the SI joint from a dorsal approach. In this example the region has an inwardly curved configuration. In this context, the term front, or forward, refers to the portion of the implant body that will typically engage tissue when the implant is advanced along a direction of implantation. The "front" of the implant body thus may extend laterally across the entire distal end of the implant body, and thus some front portions of the implant body (e.g., a central front portion) may be disposed proximally relative to other front regions of the implant. Distal region 1310 is an example of a front portion of implant body, at least a portion of which is proximal relative to distal ends of the ilium lateral side and the sacrum lateral side, as shown in FIG. 11A.

Alternatively, any of the implant bodies may have sacrum and ilium portions that have distal ends with surfaces that are configured to compress the SI joint as the implant is advanced, such as by having larger diameter regions, or one or more fins.

The central portion of implant bodies herein refers to a portion or region of the implant body that, in a top view of the implant, is laterally central or inward relative to lateral sides of the implant body, at least a portion of which is adapted or intended to be disposed in the SI joint when implanted. A long axis of the implant body may pass through central portions of implants herein. A central portion generally includes a lateral midpoint of the implant body, as measured laterally across one or both of distal and proximal ends of the implant body. Implant bodies herein do not necessarily have exact or definitive demarcations or delineations between an ilium portion and a central portion, or between a sacrum portion and central portion, but rather a central portion may include the portion or region of the implant that will be or is intended to be positioned across an SI joint when the implant body is implanted. In this regard, the use of the phrases ilium portion and sacrum portion herein refers generally to a lateral position of the portion relative to the central portion. For some or any of the implant bodies herein, it is understood that there may be some degree of lateral overlap between a central portion and at least one of the ilium portion and the sacrum portion. The phrase central portion or central region herein can thus refer to a lateral position relative to ilium and sacrum lateral sides of the implant body.

Figure 12:
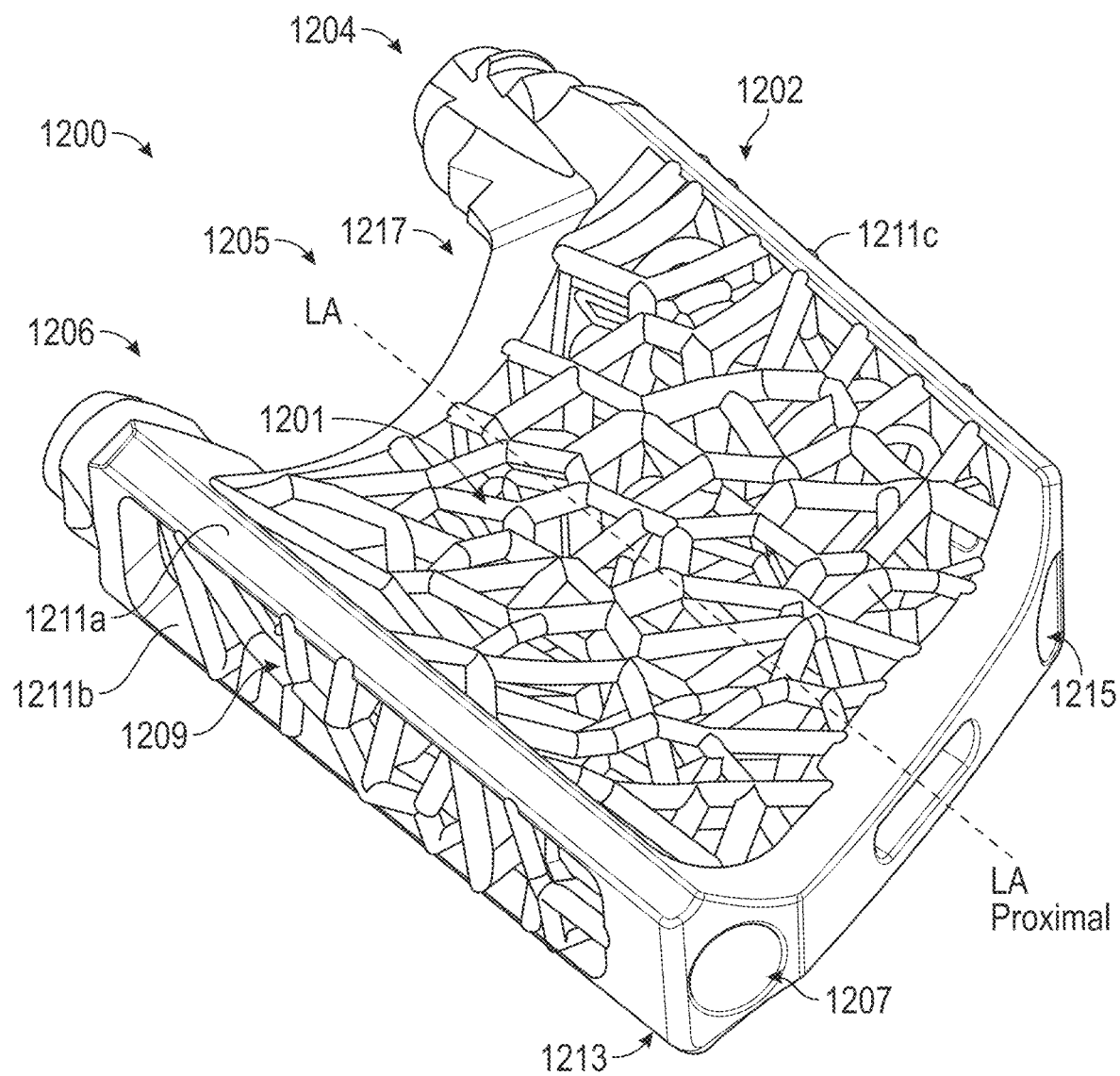
FIG. 12 illustrates an exemplary SI joint implant.

FIG. 12 illustrates a proximal and top perspective view of implant 1200, which is sized and configured for implantation across an SI joint from the dorsal approaches described herein. Implant 1200 includes implant body 1202 that includes ilium portion 1204 that is sized and configured for implanting into an ilium when the implant is implanted across a SI joint from the dorsal approach. Implant body 1202 also includes sacrum portion 1206 that is sized and configured for implanting into a sacrum when the implant is implanted across the SI joint from the dorsal approach. Any relevant description of FIGS. 11A and 11B may be incorporated by reference into the description of FIG. 12, such as the relative proximal and distal directions. Ilium portion 1204 includes and defines an elongate ilium lumen therein (not labeled) that extends from a distal opening to a proximal opening, which is sized and configured to receive therein an ilium positioning guide. Sacrum portion 1206 includes and defines an elongate sacrum lumen 1207 therein that extends from a distal opening to a proximal opening, and is sized and configured to receive therein a sacrum positioning guide. In this example, sacrum portion 1206 extends further proximally than ilium portion 1204 with reference to the length direction, as shown in FIG. 12. Ilium portion 1204 extends further distally than sacrum portion 1206, as shown, exemplary advantages of which are described herein, such as preventing the sacrum region 1206 from being advanced too far distally in the patient, which may mitigate a risk of damaging tissue distal to the desired implantation location across the SI joint. Implant body 1202 is also an example of an implant body with a parallelogram configuration that does not have four right angles, and is generally rhomboid.

While an end view is not shown, implant body 1202 is an example of an implant body that has a wafer configuration, with a height dimension that is less than a width dimension, as can be appreciated from the perspective views that are shown. In this example, sacrum lumen 1207 has a length that is greater than a length of the ilium lumen, but may be at least substantially the same (optionally being exactly the same same) as a length of the ilium lumen. The guide lumens in implant body 1202 are examples of lumens that have axes that are parallel with each other, which again includes slight deviations from perfectly parallel (e.g., lumen axes intersecting with an angle of five degrees or less therebetween). Ilium lumen is also parallel to a long axis LA of the implant body, with the long axis LA in this example extending in the length direction.

Implant body 1202 is an example of an implant body comprising one or more porous networks of interconnected struts. Implant body 1202 includes top porous network of interconnected struts 1201, a bottom porous network of interconnected struts (not labeled, but defines part of the bottom portion of the implant body), and lateral side porous network of interconnected struts 1209 (only the sacrum side of which is shown and labeled). Top porous network of interconnected struts 1201 forms at least a portion of a top portion of the implant body, and lateral side porous network of interconnected struts 1209 form at least part of the lateral sides of the implant body. In the embodiment, implant body 1202 includes frame 1213, portions of which are connected or coupled by one or more discrete porous network of interconnected struts. For example, frame 1213 includes a plurality of axially extending frame members 1211*a*, 1211*b*, 1211*c*, and 1211*d* (1211*d* is not shown or labeled, but is one of the lower or bottom members), which may also be referred to as struts, and which may be a part of the framework providing much of the structural support of the implant body. Frame 1213 may also comprise a proximal frame portion 1215, which in this example extends laterally but obliquely (but not strictly laterally) across the width of implant body 1202, and generally obliquely to the axially extending members 1211*a*-1211*d*. In this example, proximal frame portion 1215 forms a proximal side of the quadrilateral shape of the implant, which in this example is a parallelogram, and in particular a rhomboid. Implant body frame 1213 also comprises distal frame portion 1217, which in this example includes a sharpened distal end, which is described in more detail herein Similar to proximal frame portion 1215, sharpened distal end 1217 extends generally laterally but not strictly orthogonally across implant body 1202 relative to long axis LA. Frame 1213 in this embodiment comprises distal frame portion 1217, proximal frame portion 1215, and a plurality of axially extending and linear frame members 1211*a*-1211*d* coupling the proximal 1215 and distal 1217 frame members.

A plurality of discrete porous networks of interconnected struts extend between and couple the frame members, as shown, forming most of the top, bottom, and lateral sides of the implant body. The top and bottom porous networks of interconnected struts each form most of the top and bottom portions, respectively, that, in an end view of the implant, define at least partially curved configurations for the top and bottom portions of the implant. In this example, each of the lateral side porous networks of interconnected struts 1209 partially define the ilium and sacrum lumens, as shown, and in particular, define a lateral section of each of the lumens, even though the lateral sides of the lumen have openings therein in between the struts.

Body 1202 is also an example of an implant body that has a quadrilateral configuration, and in this example has a parallelogram configuration that does not include four right angles. For example, body 1202 is an example of an implant body that has a rhomboid configuration, and may alternatively have a rhombus configuration, but in alternative embodiments it may have other quadrilateral configurations (including rectangular, square, etc.).

Implant bodies herein may have, in a top view of the implant body, a general quadrilateral configuration. In this context, the term quadrilateral does not require completely linear sides. Any side of implant bodies herein may have some minor degree of curvature while still approximating a quadrilateral configuration, such as the implant body in FIG. 26.

Additional details of porous networks of interconnected struts may be found in published PCT application WO2021/108590A1, the disclosure of which is incorporated by reference herein for all purposes. For example, any and all disclosure of porous networks of interconnected struts described in WO2021/108590A1 may be incorporated into the disclosure herein, including any examples that comprise one or more porous networks of interconnected struts. For example, a porous network of interconnected struts may also be referred to as a porous lattice, or mesh. Additionally, any of the individual struts herein may also be referred to as a beam. Additionally, the porous networks of interconnected struts may have and form a smooth outer surface, such as shown in the example in FIG. 12 (as opposed to struts or beams with free ends that extend outward). Additionally, in some embodiments the porous network may have an irregular configuration of struts, or it may have a regular pattern of struts, or a combination thereof. It is therefore understood that the term lattice or network as used herein does not require a regular or repeating pattern of struts. Additionally, struts of the porous network of interconnected struts may be interconnected at connections or nodal locations, which is described in more detail in, for example, WO2021/108590A1. Connections or nodal locations herein may be the connection of two, three, four, or more individual struts or beams of the porous network of interconnected struts.

Implant bodies herein that include a porous network of interconnected struts may have added stability once implanted as the bone grows around the many struts.

Figure 13:
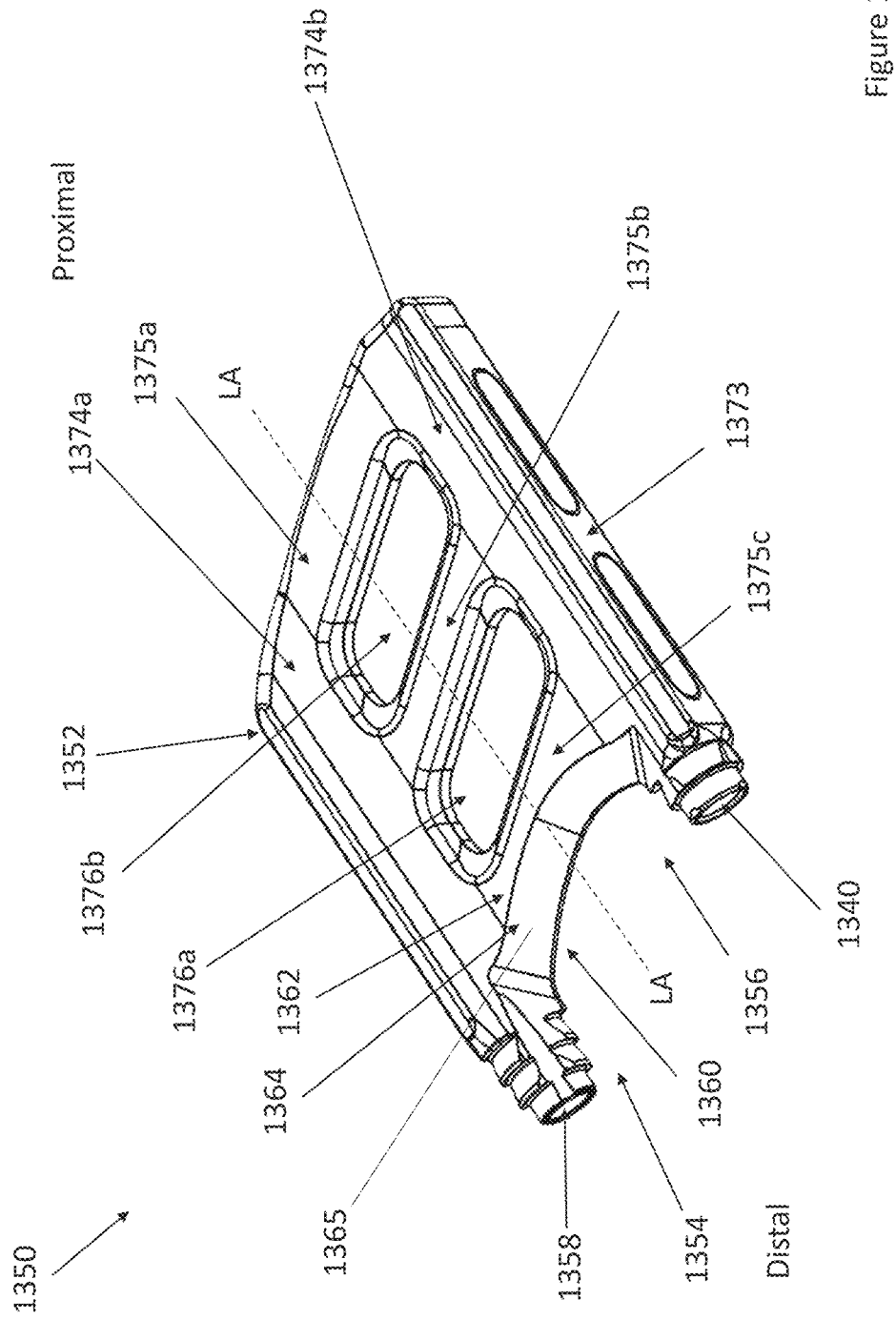
FIG. 13 illustrates an exemplary SI joint implant.

FIG. 13 is a distal and top perspective view illustrating exemplary implant 1350, which, like others herein, is sized and configured for implantation across an SI joint from the dorsal approaches herein. Implant 1350 includes implant body 1352 that includes ilium portion 1354 that is sized and configured for implanting into an ilium when the implant is implanted across an SI joint from the dorsal approach. Implant body 1352 also includes a sacrum portion 1356 that is sized and configured for implanting into a sacrum when the implant is implanted across the SI joint from the dorsal approach. Any relevant description of FIGS. 11A-12B may be incorporated by reference to the description of FIG. 13. Ilium portion 1354 includes and defines an elongate ilium guide lumen 1358 that extends from a distal opening to a proximal opening, and is sized and configured to receive therein and move relative to an ilium positioning guide (not shown). Sacrum portion 1356 includes and defines an elongate sacrum lumen 1340 therein that extends from a distal opening to a proximal opening, and is sized and configured to receive therein a sacrum positioning guide. In this example, sacrum portion 1356 extends further proximally than ilium portion 1354 with reference to a length direction. Ilium portion 1354 extends further distally than sacrum portion 1356, as shown, exemplary advantages of which are described herein. Implant body 1352 is also an example of an implant body with, in a top view, a parallelogram configuration that does not include four right angles, and in this example has a rhomboid configuration (but may alternatively have a rhombus configuration). Implant body 1352 is also an example of an implant body that has a wafer configuration. In this example, sacrum lumen 1340 has a length that is slightly greater than a length of the ilium lumen 1358, but in alternatives it may be at least substantially the same or exactly the same as a length of the ilium lumen 1358. The guide lumens in implant body 1352 are examples of lumens that have long axes that are parallel, which includes slight deviations from perfectly parallel (described herein). Ilium lumen 1358 and sacrum lumen 1340 are also parallel to a longitudinal (or long) axis LA of the implant body, with the long axis in this example extending in the length direction. In this example, long axis LA extends through a lateral midpoint of the implant body (e.g., dividing the implant body laterally into halves). As shown in the examples herein, a long axis of the implant body may or may not be a line of symmetry of the implant body in a top view of the implant body. In FIGS. 11A-28, the long axis of the respective implant body is not a line of symmetry of the implant body in a top view. Implant body 1352 also includes a distal portion, at least a portion of which comprises sharpened distal end 1360, which is described in detail elsewhere herein. Sharpened or cutting distal end 1360 has a tapered configuration 1364, which tapers downward from a top portion 1362 of the implant body and that tapers upward from a bottom portion of the implant body. In this embodiment, tapering surface 1365 tapers downward and distally from top portion 1362, and a tapering surface (not shown but on the bottom side of implant body 1352) tapers upward and distally from the bottom portion of the implant body. The sharpened distal end 1360 has some height dimension that is less than the height between the top and bottom portions of the implant body from which the tapered surfaces extend. The tapering surfaces help the distal end 1360 penetrate into bone during implantation. Distal end 1360, as shown, also has a concave curve configuration in a top view, and is recessed proximally relative to the distal ends of ilium portion 1354 and sacrum portion 1356, as shown.

Implant body 1352 also comprises frame 1373. Implant body 1352 may be monolithic (and may be 3D printed, for example), frame 1373 includes first and second axially extending elongate regions 1374a and 1374b, which are in ilium portion 1354 and sacrum portion 1356, respectively. Axially extending elongate regions 1374a and 1374b are connected or coupled together by generally oblique connecting members 1375a, 1375b and 1375c, which extend across the long axis, and extend from elongate region 1374b non-orthogonally relative to the elongate region 1374b, and in this example extend from elongate region 1374*b* partially distally such that they have a slanted configuration and are further distally in the ilium portion than in the sacrum portion. The distal most connector 1375*c* includes, in this example, top surface 1362 from which the tapered surface 1365 extends distally and downward. The distal connector 1375*c* also includes a corresponding bottom surface of the implant and a bottom tapered surface that extends distally and upward. Frame 1373 is an example of a frame that has a shape that, in a top view, resembles a digital eight configuration that is slanted further distally on the ilium side.

The implant will be subject to stresses when implanted across the SI joint with a portion of the implant in the sacrum and a portion of the implant in the ilium. Connectors 1375 of the frame are adapted to resist both bending and shear forces.

Frame 1373, in this embodiment, further defines a plurality of fenestrations (or openings) 1376*a* and 1376*b*, which as shown extend through the top and bottom portions or surfaces of the implant body. The fenestrations in any of the implant bodies herein can facilitate the ingrowth or ongrowth of tissue, while in some examples (such as FIGS. 15A-15C) the fenestrations may be used to facilitate delivery of one or more agents into the patient. In alternative embodiments, any of the frames herein may include more than two fenestrations, such as from three to two hundred fenestrations. Implant body 1302 in FIG. 11A is, for example, an example of an implant body including nine fenestrations 1320 extending through top and bottom portions or surfaces of the implant. Elongate members 1374*a* and 1374*b* and connecting members 1375*a*, 1375*b* and 1375*c*, in this embodiment, define fenestrations 1376*a* and 1376*b* that extend through the top and bottom portions of implant body.

FIG. 14 is a top view illustrating exemplary implant 1400, which, like others herein, is sized and configured for implantation across an SI joint from a dorsal approach. Implant 1400 includes implant body 1402, which is similar to implant 1350 in some ways. Implant body 1402 includes ilium portion 1404 that is sized and configured for implanting into an ilium when the implant is implanted across a SI joint from the dorsal approach. Implant body 1402 also includes sacrum portion 1406 that is sized and configured for implanting into a sacrum when the implant is implanted across the SI joint from the dorsal approach. Any relevant description of FIGS. 11A-13 may be incorporated by reference to the description of FIG. 14. Ilium portion 1404 includes and defines an elongate ilium lumen therein (not labeled) that extends from a distal opening to a proximal opening, and is sized and configured to receive therein an ilium positioning guide. Sacrum portion 1406 includes and defines an elongate sacrum lumen therein (not labeled) that extends from a distal opening to a proximal opening, and is sized and configured to receive therein a sacrum positioning guide. In this example, sacrum portion 1406 extends further proximally than ilium portion 1404, as shown. Ilium portion 1404 extends further distally than sacrum portion 1406, as shown. Implant body 1402 is also an example of an implant body with, in a top view, a parallelogram configuration without right angles, and in particular has a rhomboid configuration (which may alternatively have a rhombus configuration if all sides have the same length).

Implant body 1402 is an example of an implant body that has a wafer configuration. In this example, the sacrum lumen has a length that is slightly greater than a length of the ilium lumen, although in alterative embodiments they may be substantially the same. The guide lumens in implant body 1402 are examples of lumens that have axes (ilium lumen axis "ILA" and sacrum lumen axis "SLA") that are parallel with each other, which again includes slight deviations from perfectly parallel. ILA and SLA are also each parallel to a long axis LA of the implant body, as shown, which passes through a lateral midpoint of implant body.

Implant body 1402 also comprises frame 1413, which is similar in some ways to frame 1373 in FIG. 13, and which may have the same general configuration as frame 1373 in FIG. 13. Implant body 1402 also includes porous network of interconnected struts 1401, which may be additively manufactured with frame 1373, for example, to form implant body 1402. The disclosure that is incorporated by reference herein related to porous network of interconnected struts, such as the disclosure in WO2021/108590A1, may be incorporated into network 1401 of implant 1402. Network 1401 may extend over and about a portion of frame 1413, as shown, including over and about the lateral sides of the frame, as shown. As shown, network of interconnected struts 1401 may be at least partially continuous (or uninterrupted) laterally across portions of implant body, over a first lateral side, laterally across the bottom of implant body, and over the other lateral side. In some embodiments the network of struts may extend over and about a portion of frame 1413. In some ways, implant body 1402 in FIG. 14 includes aspects of frame 1373 from FIG. 13 and network of struts 1201 from FIG. 12.

All of the disclosure from FIG. 13 related to frame 1373 is incorporated by reference in its entirety into the disclosure of FIG. 14 with respect to frame 1401.

Implant body 1402 is also an example of an implant body with a general quadrilateral configuration. In this example, the quadrilateral configuration does not include right angles, and is an example of an implant body with a rhomboid configuration. In alternative embodiments, implant body 1402 may have a rhombus configuration, or it may have any other quadrilateral configuration (including rectangular, square, etc.). The proximal end of implant body 1402 is an example of a back or proximal side of an implant body that is considered a side, even though it does not have complete linearity.

Figure 15A:
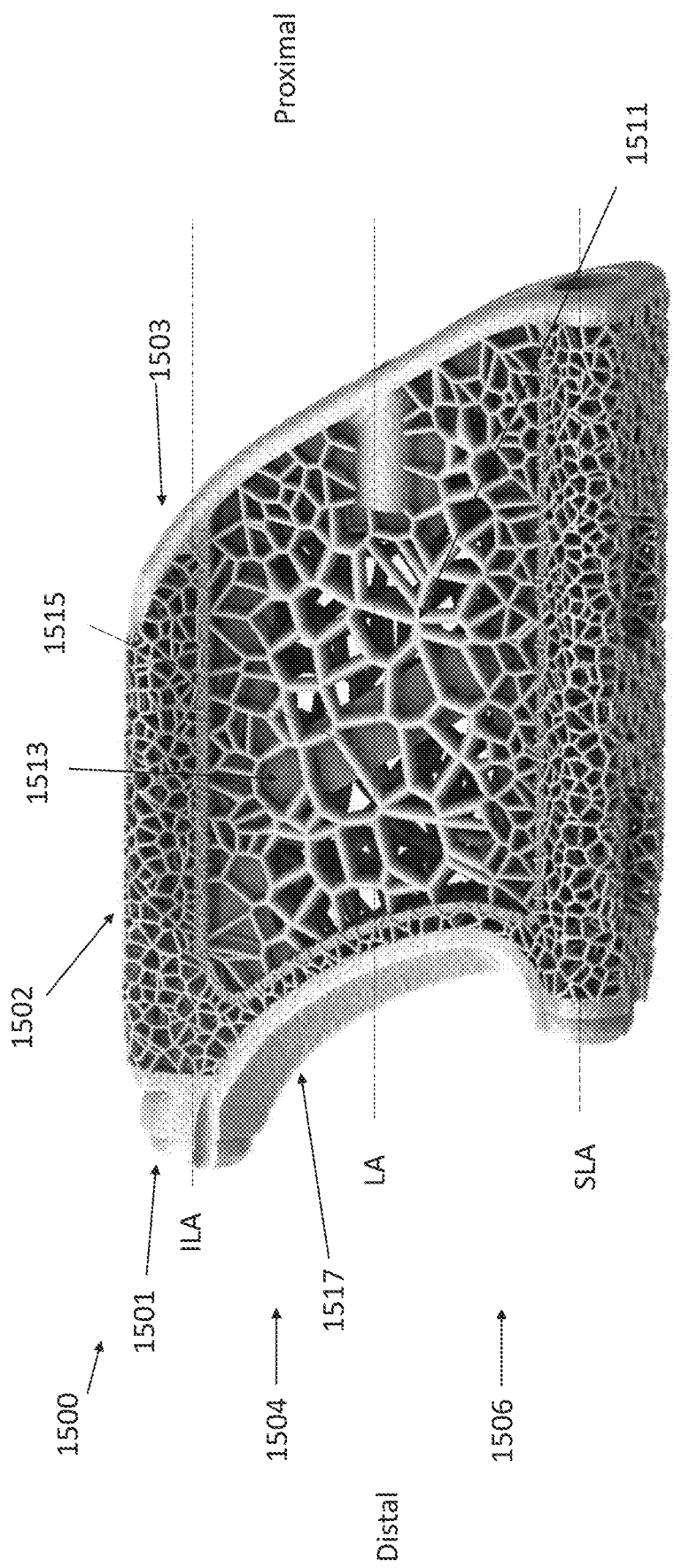
FIGS. 15A, 15B and 15C illustrate an exemplary SI joint implant.
Figure 15B:
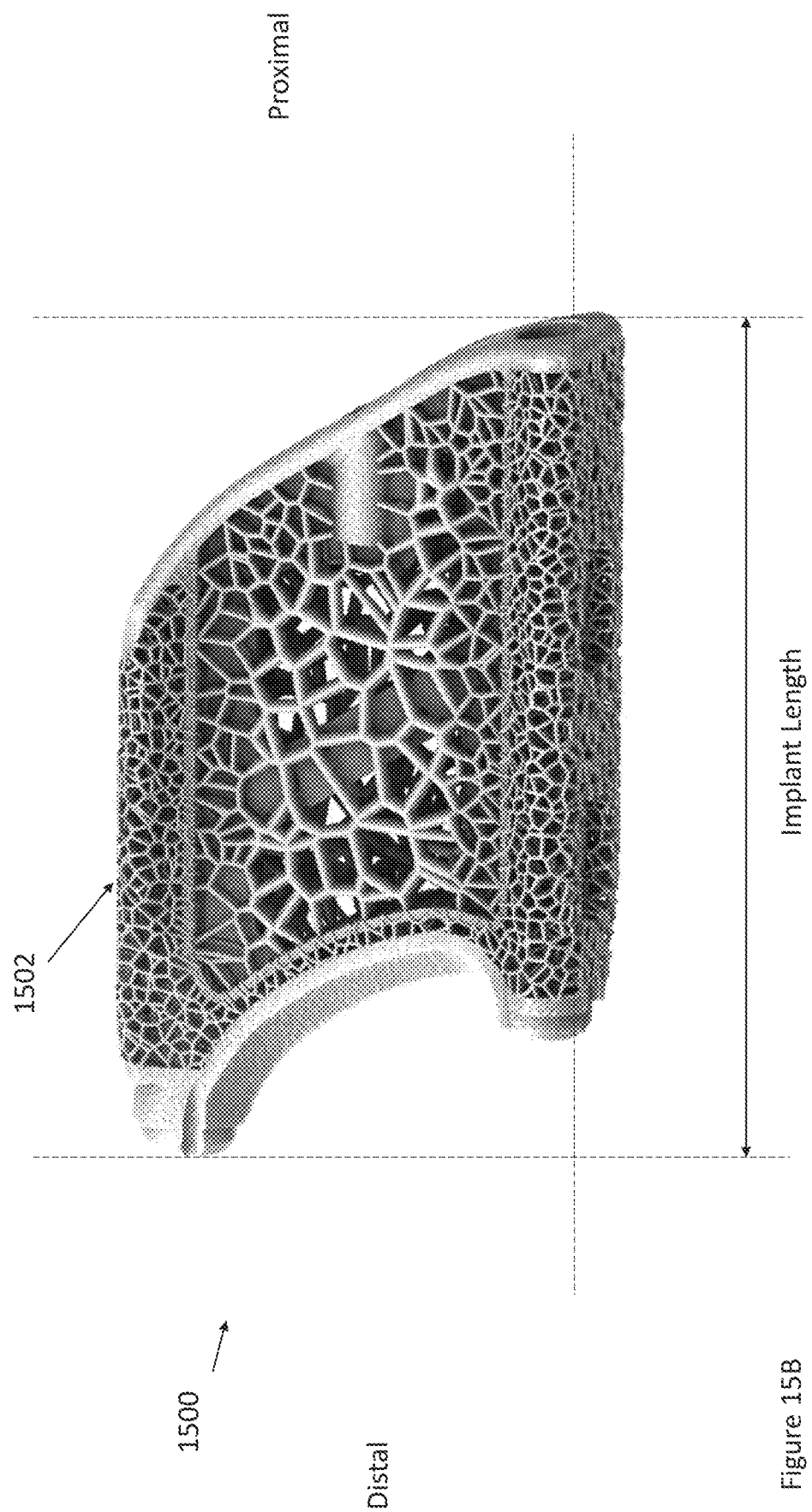
Figure 15C:
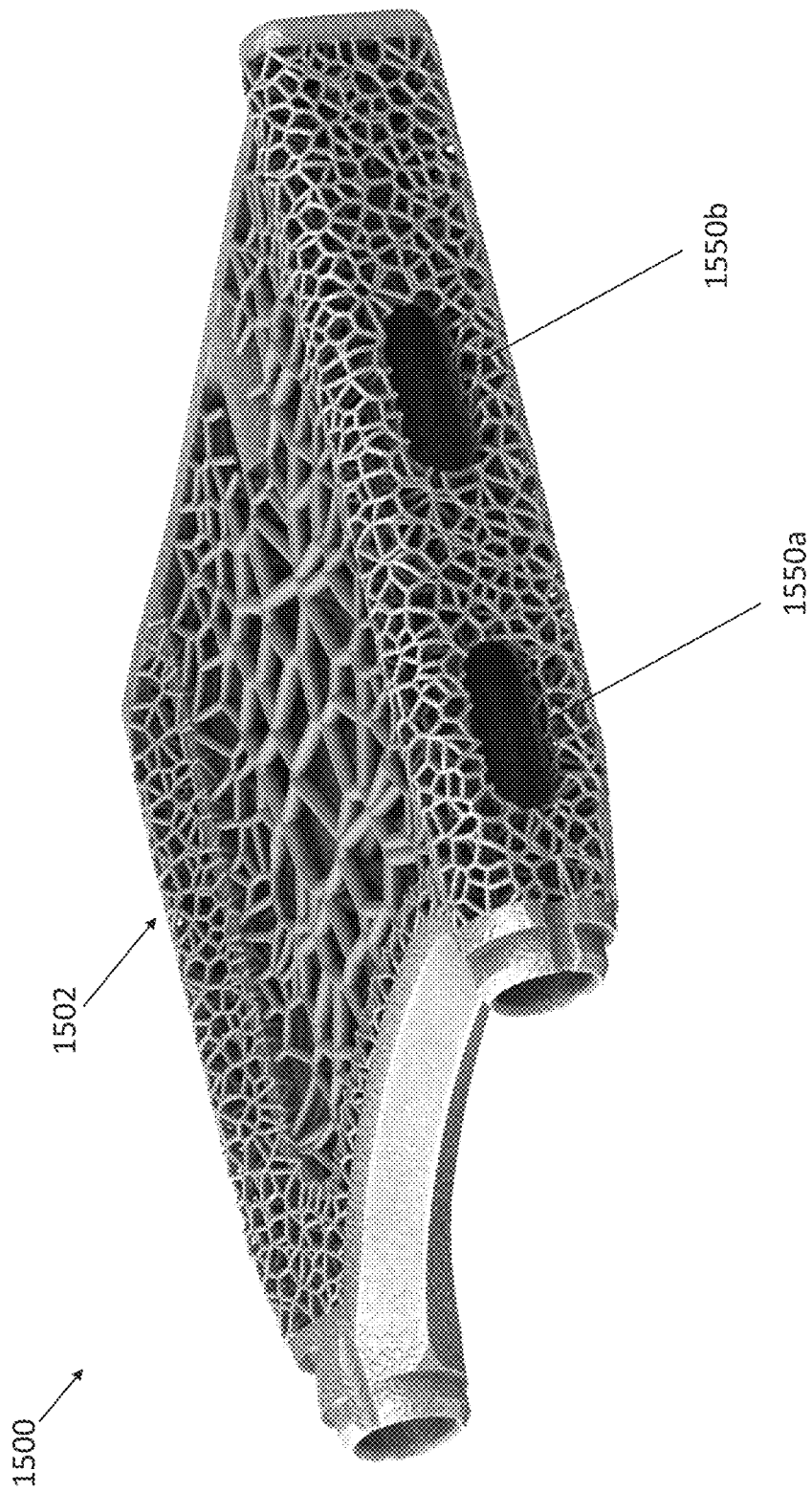

FIGS. 15A-15C illustrate implant 1500, which is sized and configured for implantation across a SI joint from a dorsal approach, which is described herein. Implant 1500 includes implant body 1502 that includes ilium portion 1504 that is sized and configured for implanting into an ilium when the implant is implanted across a SI joint from the dorsal approach. Implant body 1502 also includes a sacrum portion 1506 that is sized and configured for implanting into a sacrum when the implant is implanted across the SI joint from the dorsal approach. Any relevant description of FIGS. 11A-14 may be incorporated by reference to the description of FIGS. 15A-15C. Ilium portion 1504 includes and defines an elongate ilium lumen therein (not labeled) that extends from a distal opening 1501 to a proximal opening 1503, and is sized and configured to receive therein an ilium positioning guide. Sacrum portion 1506 similarly includes and defines an elongate sacrum lumen therein that extends from a distal opening to a proximal opening, and is sized and configured to receive therein a sacrum positioning guide. Exemplary lumens are described herein, and may each have a long axis. In this example, and as shown, sacrum portion 1506 extends further proximally than the ilium portion 1504. Ilium portion 1504 extends further distally than sacrum portion 1506, as shown, exemplary advantages of which are described herein. Implant body 1502 is also an example of an implant body with a parallelogram configuration without right angles, and in this example has a rhomboid configuration, exemplary benefits are described herein.

Implant body 1502 is an example of an implant body with a wafer configuration with a height dimension that is less than a width dimension. As shown, and in this example, the sacrum lateral side and sacrum lumen have lengths that are greater than corresponding lengths of the ilium lumen and ilium lateral side. The guide lumen axes in implant body 1502 are examples of lumens that have axes (ilium lumen axis ILA; sacrum lumen axis SLA) that are parallel to each other (as shown), which includes slight deviations from perfectly parallel. Ilium lumen axis ILA and sacrum lumen axis SLA are each also parallel to long axis LA of the implant body, as shown, which includes slight deviations from perfectly parallel.

Implant body 1502 further includes inner frame 1513, which may include the same general or similar configuration as the frame in the embodiment in FIGS. 12 and 13. In this regard, the entire disclosure of the frame from the embodiments in FIGS. 12 and 13 is incorporated by reference herein to the disclosure of frame 1513. For example, frame 1513 includes a plurality of axially extending frame members (not labeled) but may be the same or similar to those in FIG. 13) and oblique or slanted connecting members (one of which is labeled, 1515) coupling and extending between the axially extending frame members. Connecting member(s) 1515 also extend obliquely across long axis LA, as shown. Implant body 1502 also comprises distal sharpened end 1517, which has a concave shape as shown, and which is described in more detail herein, and which extends generally laterally across implant body 1502, as shown.

Implant body 1502 is an example of an implant body comprising one or more porous network of interconnected struts, as shown. Implant body 1502 includes a porous network of interconnected struts 1511 that in this embodiment extends over and about a top implant body portion, a bottom implant portion, and lateral sides of the implant body. In this embodiment, porous network of interconnected struts 1511 define larger cells or pores in the central region than in the ilium and sacrum portions of the implant, as shown.

Implant body 1502 is an example of an implant body with a quadrilateral configuration. In this example, the quadrilateral configuration does not include right angles, and is an example of an implant body with a rhomboid configuration. In alternative embodiment, implant body 1502 may have a rhombus configuration, but in alternative embodiments it may have any other quadrilateral configuration (including rectangular). The proximal end of implant body in FIG. 15 is an example of a proximal portion of an implant body that is considered to approximate a side of a quadrilateral even though it does not have complete linearity, as is shown.

FIG. 15B illustrates implant 1500, and illustrates the exemplary length of the implant, measured axially from the distal end to the proximal end of the implant.

FIG. 15C illustrates a perspective view of implant 1500, and also illustrates lateral side fenestrations 1550a and 1550b in the sacrum side of the implant, and which are in communication with the sacrum lumen as shown. Fenestrations 1550a and 1550b may be used to help facilitate delivery of an agent into the patient via delivery of the agent through the proximal opening of the sacrum lumen. Alternatively or additionally, fenestrations 1550a and 1550b may help tissue growth therethrough, which can help stabilize the implant. The ilium lateral side can similarly have fenestrations 1550a and 1550b therethrough. The lateral sides of the implant can optionally have one or more fenestrations 1550 therethrough, such as, without limitation, from one to ten, or more.

FIG. 16 is a top view illustrating exemplary implant 1600, which, like others herein, is sized and configured for implantation across an SI joint from a dorsal approach. Implant 1600 may incorporate any suitable feature of any other implant body herein, such as those shown and described with respect to FIGS. 11A-15. Implant 1600 includes implant body 1602 that includes ilium portion 1604 that is sized and configured for implanting into an ilium when the implant is implanted across an SI joint from the dorsal approach. Implant body 1602 also includes sacrum portion 1606 that is sized and configured for implanting into a sacrum when the implant is implanted across the SI joint from the dorsal approach. Ilium portion 1604 includes and defines an elongate ilium guide lumen (not labeled) that extends from a distal opening to a proximal opening, and is sized and configured to receive therein an ilium positioning guide. Sacrum portion 1606 includes and defines an elongate sacrum lumen therein that extends from a distal opening to a proximal opening, and is sized and configured to receive therein a sacrum positioning guide. In this example, sacrum portion 1606 extends further proximally than ilium portion 1604, as shown, exemplary advantages of which are described herein. Ilium portion 1604 extends further distally than sacrum portion 1606, as shown, exemplary advantages of which are described herein. Implant body 1602 is also an example of an implant body with, in a top view, a parallelogram configuration without right angles, as shown, which may be rhomboid or rhombus shaped. Implant body 1602 is also an example of an implant body with a wafer configuration that has a height dimension that is less than a width dimension. In this example, the sacrum lumen and sacrum side have lengths that are greater than length of the ilium lumen and ilium lateral side, respectively (as shown). The guide lumens are examples of lumens that have long axes that are parallel with each other (as shown), which includes slight deviations from perfectly parallel. Elongate ilium lumen axis ILA and sacrum lumen axis SLA are also parallel to a longitudinal (or long) axis LA of the implant body, as shown. As shown in the examples herein, a long axis of the implant body LA may or may not be a line of symmetry of the implant body (in a top view), which in this case it is not. Implant body 1602 also includes a distal portion, at least a portion of which comprises sharpened distal end 1617, exemplary details of which are described herein, and which may be incorporated into this embodiment. For example, sharpened or cutting distal end 1617 has a tapered configuration that tapers downward from a top portion of the implant body and that tapers upward from a bottom portion of the implant body.

In this example, implant body 1602 includes a frame, which as shown does not comprise fenestrations through top and bottom portions of the implant body (e.g., such as fenestrations 1376a and 1376b). Any of the implants herein may not include fenestrations through top and bottom portions of the implant body, as is the case with implant body 1602.

Implant body 1602 is an example of an implant body with a wafer configuration with a height dimension that is less than a width dimension. As shown, and in this example, the sacrum side and sacrum lumen have lengths that are greater than corresponding lengths of the ilium lumen and ilium side, respectively. The guide lumen axes in implant body 1602 are examples of lumens that have axes (ilium lumen axis ILA; sacrum lumen axis SLA) that are parallel to each other (as shown), which includes slight deviations from perfectly parallel. Ilium lumen axis ILA and sacrum lumen axis SLA are each also parallel to long axis LA of the implant body, as shown, which includes slight deviations from perfectly parallel.

Implant body 1602 is an example of an implant body with a general quadrilateral configuration. In this example, the quadrilateral configuration does not include right angles, and is an example of an implant body with a rhomboid configuration, additional examples of which are shown herein. In alternative embodiment, implant body 1502 may have a rhombus configuration, but in alternative embodiments it may have any other quadrilateral configuration (including rectangular).

Implant 1600 may incorporate any other suitable feature of any of implant body herein.

Figure 17C:
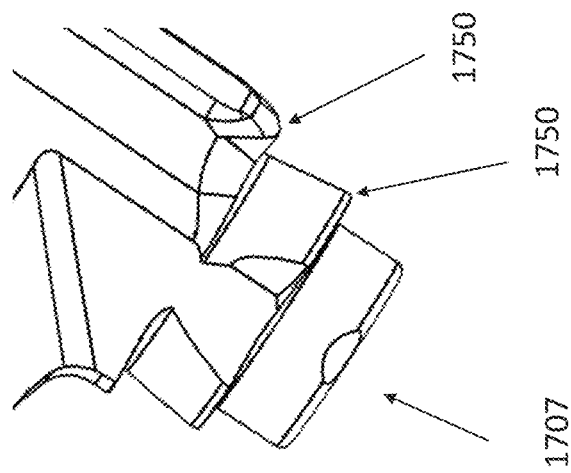
FIGS. 17A, 17B and 17C illustrate exemplary cutting edges disposed about optional lumens.
Figure 17B:
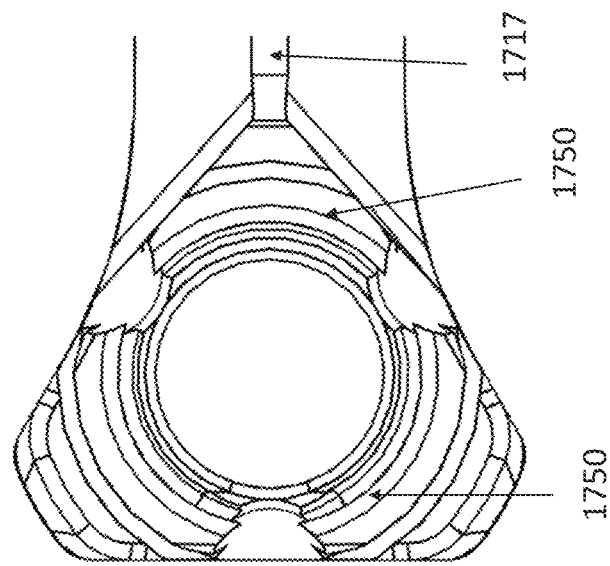
Figure 17A:
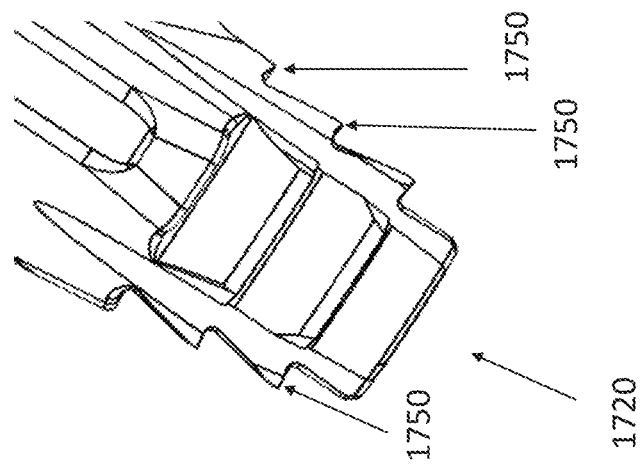

FIGS. 17A and 17B illustrate an exemplary distal end 1720 of an ilium portion of an implant body, features of which may be incorporated into any of the distal ends of the ilium portions herein. FIG. 17B is a front end view, also showing the ilium lumen. FIG. 17C illustrates an exemplary distal end 1707 of a sacrum portion of an implant body, features of which may be incorporated into any of the distal ends of the sacrum portions herein. The distal end 1720 and 1707 both include a plurality of cutting edges 1750, which in each case progressively have larger dimensions moving proximally, as shown. The configuration of the cutting edges 1750 on each end acts like a broach to help both ends penetrate into bone as the implant is advanced distally. Cutting edges 1750 have annular configurations, as shown, which may be colinear with the lumen axes, which is also shown. Exemplary sharpened distal end 1717 is shown in FIG. 17B, exemplary details of which are described herein. In this example, the ilium distal end 1720 has three axially spaced annular cutting edges, while the sacrum region distal end 1707 has two axially spaced annular cutting edges. Each end may have more or fewer cutting edges. Cutting edges like those shown in FIGS. 17A-17C are shown in the implant bodies in FIGS. 12, 13, 14, 15A-15C and 16, and thus the description of these other figures implicitly includes the description of FIGS. 17A-17C.

Any of the ilium portions herein may have cutting edges, such as those shown in FIGS. 17A and 17B. Any of the sacrum portions herein may have cutting edges, such as those shown in FIG. 17C.

Figure 18B:
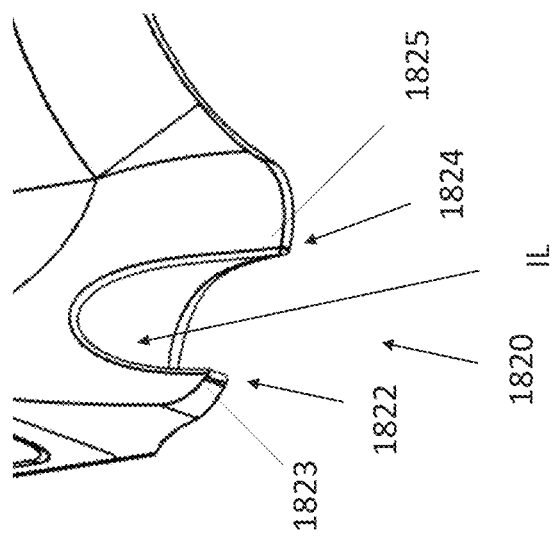
Figure 18A:
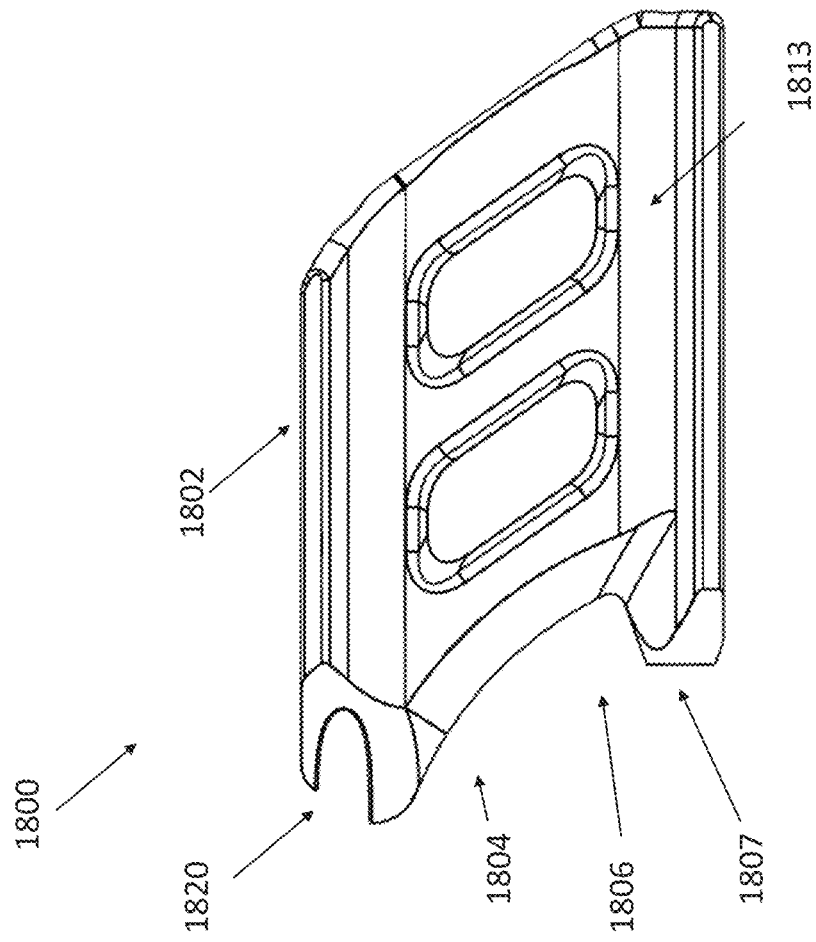

FIGS. 18A-18C illustrate implant 1800, which include implant body 1802 that may be the same as implant body 1352 from FIG. 13 in all ways, except those described herewith. Implant body 1802 includes ilium portion 1804 that includes distal end 1820 with a configuration that helps penetrate or cut through tissue as the implant is being advanced distally. FIG. 18B illustrates a close-up perspective view of distal end 1820 of ilium region 1804. Ilium region 1804 includes ilium lumen IL, additional details of which are described herein. Distal end 1820 includes first cutting region 1822 with a first cutting member 1823, and a second cutting region 1824 with a second cutting member 1825. Concave surfaces extend between the two cutting regions, as shown. Second cutting region 1824 extends further distally and is wider than first cutting region 1822. First cutting member 1823 has a height that is greater than a height of second cutting member 1825. Cutting edges of both first and second cutting members 1823 and 1825 are relatively sharp and help penetrate through tissue as implant 1800 is advanced.

Sacrum region 1806 includes distal end 1807, which may have the same configuration as any other sacrum or ilium portion distal end herein (including like distal end 1820). The sacrum portion may optionally include sacrum lumen SL as shown in FIG. 18C, but in alternative embodiments the sacrum portion may not include a lumen, as is described in examples herein. Implant body 1802 also has a sharpened distal end extending at least in the central portion of the implant body, examples of which are described herein and the disclosure of which is incorporated by reference into the description of FIGS. 18A-18C.

Implant body 1802 is an example of an implant body with a general quadrilateral configuration. In this example, the quadrilateral configuration does not include right angles, and is an example of an implant body with a rhomboid configuration. In alternative embodiment, implant body 1802 may have a rhombus configuration, while in alternative embodiments it may have any other quadrilateral configuration.

FIG. 19 shows a top view of implant 1900, which includes implant body 1902, which may be the same in any or all ways as implant body 1802 in FIGS. 18A-18C except for those details described herewith. Implant body 1902 includes frame 1913 and one or more porous network of interconnecting struts 1930 extending from frame 1913. A porous network of interconnecting struts 1930 may by the same in any or all ways as porous network of interconnecting struts 1401 from FIG. 14. Implant body 1902 is an example of an implant body with a general quadrilateral configuration. In this example, the quadrilateral configuration does not include right angles, and is an example of an implant body with a rhomboid configuration. In alternative embodiment, implant body 1902 may have a rhombus configuration, but in alternative embodiments it may have any other quadrilateral configuration.

Figure 20:
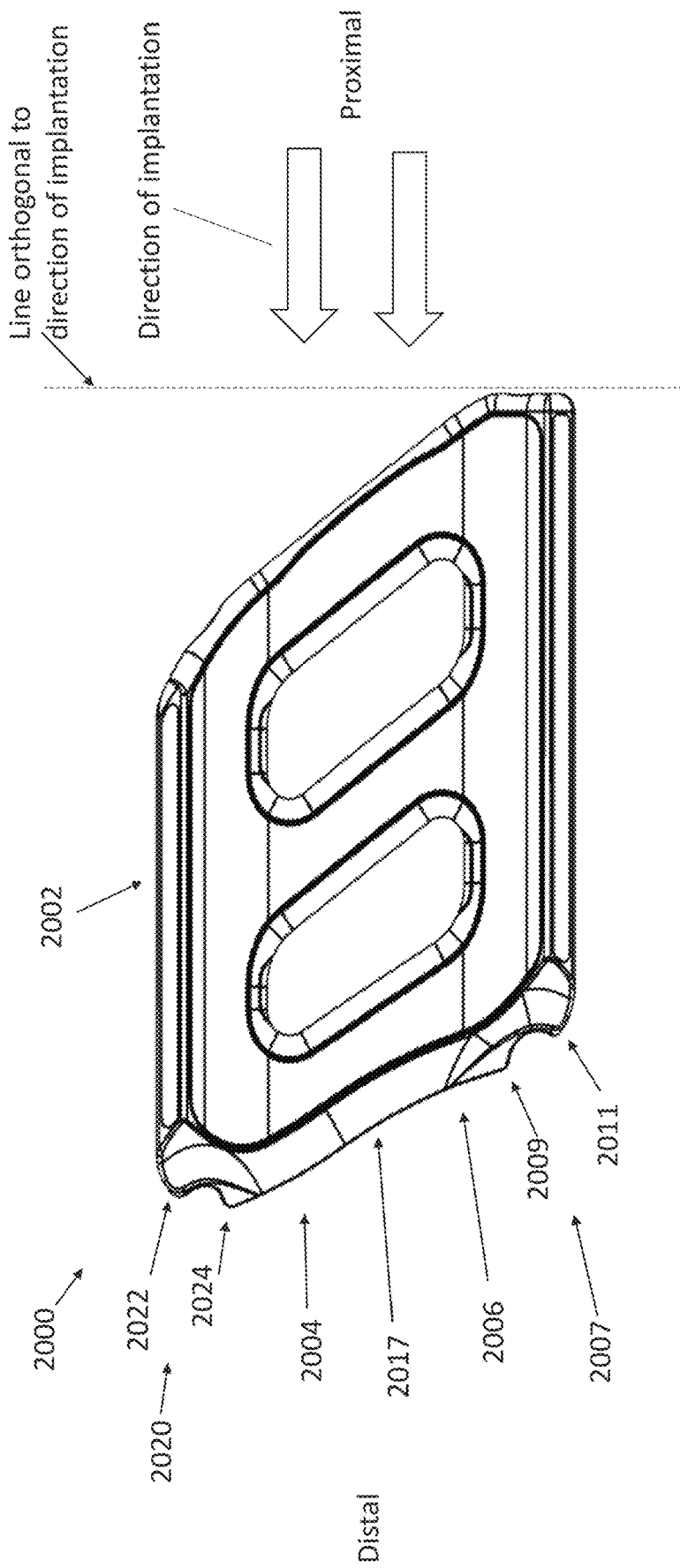
FIG. 20 illustrates an exemplary SI joint implant.

FIG. 20 is a top view of implant 2000, which, like others herein, is sized and configured for implantation across an SI joint from a dorsal approach. Implant 2000 may incorporate any suitable feature of any other implant body herein, such as those shown and described with respect to FIGS. 11A-19. Implant body 2002 may be the same as implant body 1802 from FIGS. 18A and 18B in any or all other ways except those described herewith. Implant body 2002 includes ilium portion 2004 with an ilium portion distal end 2020 that does not extend as far distally as some ilium portion distal ends described herein. Additionally, sacrum portion 2006 includes sacrum portion distal end 2007 that does not extend as far distally as some sacrum portion distal ends described herein. Distal end 2020 of ilium portion 2004 includes first cutting region 2022 and second cutting region 2024, and distal end 2007 of sacrum portion 2006 includes first cutting region 2009 and second cutting region 2011, all of which have pointed or sharpened configurations that help penetrate or cut into tissue as the implant is advanced distally. Each of the adjacent sharpened regions have concave surfaces therebetween in the top view, as shown.

Implant body 2002 includes a distal portion that includes sharpened distal end 2017 (which extends through the central region of the implant body. Any or all exemplary details of any of the sharpened distal ends herein may be incorporated by reference into sharpened distal end 2017 of FIG. 20. In this embodiment, due partially to the distal end of distal ends 2020 and 2007, sharpened distal end 2017 does not have as pronounced a concave curve as in other embodiments herein. In fact, as shown, sharpened distal end 2017 has a slight "S" shape curvature, as shown. Sharpened end 2017 thus has a convex curvature along a first portion of the front face, and is concave along a second portion of the front face, wherein the convex region is closer to the ilium side, as shown. Any of the implant bodies herein may be modified to include any or all of the features shown and described with respect to FIG. 20.

Implant body 2002 is an example of an implant body with a general quadrilateral configuration. In this example, the quadrilateral configuration does not include right angles, and is an example of an implant body with a rhomboid configuration. In alternative embodiment, implant body 2002 may have a rhombus configuration, but in alternative embodiments it may have any other quadrilateral configuration.

Figure 21:
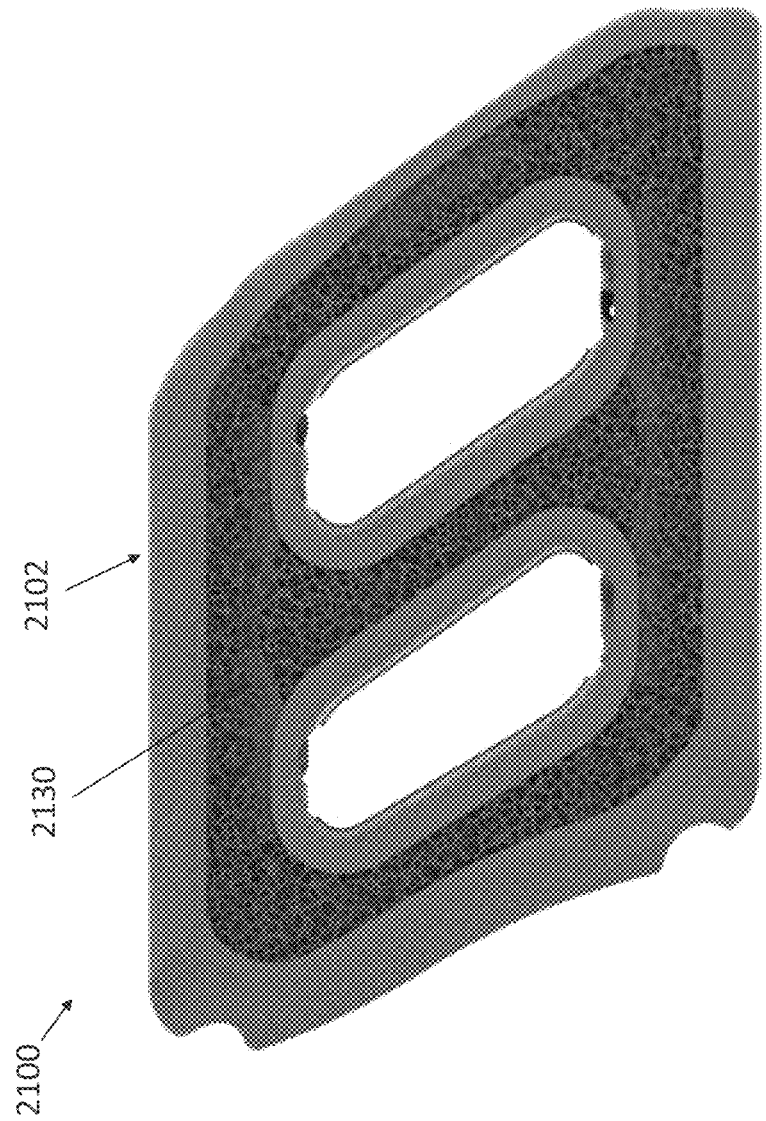
FIG. 21 illustrates an exemplary SI joint implant.

FIG. 21 is a top view of implant 2100, which, like others herein, is sized and configured for implantation across an SI joint from a dorsal approach. Implant 2100 may be the same as implant 2000 in any or all ways except as described herewith. Implant body 2130 includes a plurality of porous networks of interconnecting struts 2130. While only one network 2130 is shown that extends over a portion of the top portion of the implant 2100 (the network similar have a slanted digital eight configuration), it is understood that a second network 2130' (not labeled) may similarly extend over the corresponding bottom portion of the implant body 2102. Network 2130 may be considered similar to network 1930 shown and described with respect to FIG. 19. Implant body 2102 is an example of an implant body with a general quadrilateral configuration. In this example, the quadrilateral configuration does not include right angles, and is an example of an implant body with a rhomboid configuration. In alternative embodiment, implant body 2102 may have a rhombus configuration, but in alternative embodiments it may have any other quadrilateral configuration.

Figure 22C:
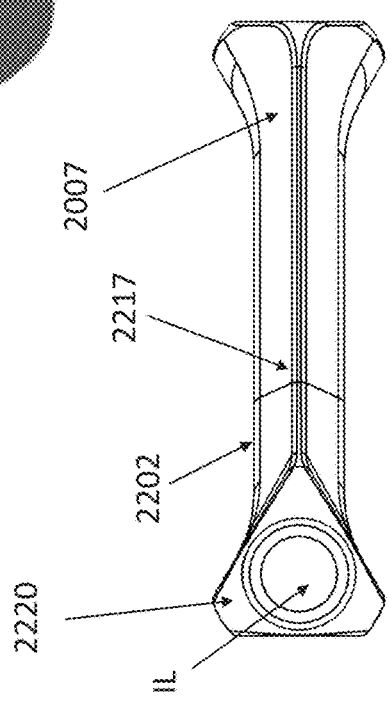

FIGS. 22A-22C illustrate implant 2200, which may include any suitable feature from any of implant 1350 in FIG. 13, implant 1600 in FIG. 16, implant 1800 from FIGS. 18A-18C, and/or implant 2000 from FIG. 20, except with respect to the features described herewith. Implant 2200 includes implant body 2202, for which sacrum lumen SL does not have a distal opening, as shown. As such, delivery of implant 2200 does not include delivery over a sacrum guide, examples of which are described herein. Implant body 2202 includes a sacrum lumen SL, however, that includes a proximal opening, as shown, which may help facilitate growth on the lateral sacrum side via lateral sacrum side fenestrations 2240a and 2240b, as shown, or delivery of an agent therethrough as described herein. Additionally, as shown, distal end 2220 of the ilium region extends further distally than distal end 2207 of the sacrum region.

Implant body 2202 also includes a distal portion that comprises a sharpened distal end 2217, exemplary details of which are described herein and may be incorporated fully into the description of FIGS. 22A-22C. The curvature of the sharpened distal end has a varying radius of curvature along the curve, and may include a concave section and a convex section, for example. In the embodiment in FIGS. 22A-22C, the sharpened distal end comprises a convex section that is closer to the ilium lateral side than the sacrum lateral side, and includes a concave curve section that is closer to the sacrum side than the ilium side, as shown.

Implant body 2202 is an example of an implant body with a general quadrilateral configuration. In this example, the quadrilateral configuration does not include right angles, and is an example of an implant body with a rhomboid configuration. In alternative embodiment, implant body 2202 may have a rhombus configuration, but in alternative embodiments it may have any other quadrilateral configuration.

Figure 23B:
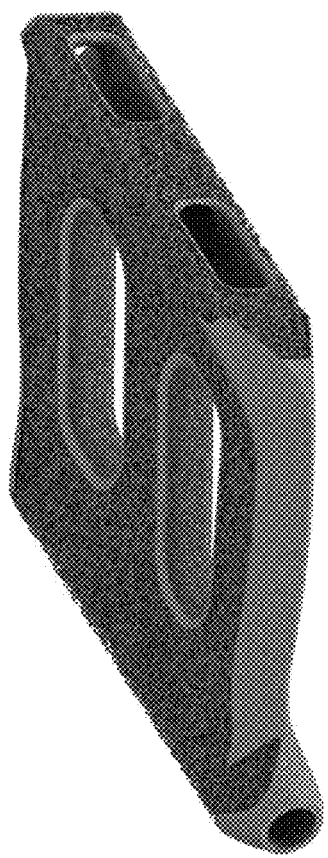
FIGS. 23A and 23B illustrate an exemplary SI joint implant.
Figure 23A:
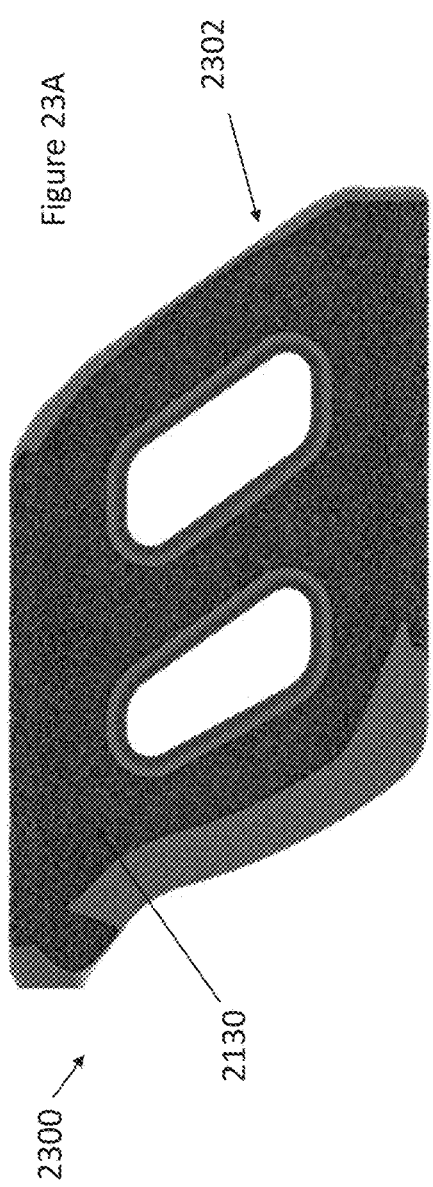

FIGS. 23A and 23B illustrate implant 2300 comprising implant body 2302, which may include any of the features of implant 2200 described with respect to FIGS. 22A-22C. As with other examples herein, implant 2300 may include one or more network of struts 2130 extending about any portion of the implant body, examples of which are shown in FIGS. 23A and 23B.

Implant body 2302 is an example of an implant body with a general quadrilateral configuration. In this example, the quadrilateral configuration does not include right angles, and is an example of an implant body with a rhomboid configuration. In alternative embodiment, implant body 2302 may have a rhombus configuration, but in alternative embodiments it may have any other quadrilateral configuration.

FIG. 24 is a top view of an exemplary implant 2400 with implant body 2402. Any suitable feature (including the absence of any features, such as a lumen) from any other implant body herein may be incorporated into implant body 2402.

Implant body 2402 is an example of an implant body with a general quadrilateral configuration. In this example, the quadrilateral configuration does not include right angles. In alternative embodiments it may have any other quadrilateral configuration, such as a right trapezoid if the two lateral sides of implant body 2402 were modified to horizontal in FIG. 24 (parallel with the axes of the lumens).

Implant body includes a distal portion with sharpened distal end 2417, which may be configured as any of the sharpened ends described herein, all of which are incorporate by reference into the description of FIG. 24.

FIG. 24 also conceptually illustrates exemplary lines L that are annotated in the top view of implant body 2402. Lines L are orthogonal to both a long axis LA of the implant body 1402, as well as to lumen axes ILA and SLA, as shown. Lines L are also orthogonal to the direction of implantation, which refers to a direction in or trajectory along which the implant is implanted.

FIG. 25 is a top view of an exemplary implant 2500 with implant body 2502. Any suitable feature (including the absence of any features, such as a lumen) from any other implant body herein may be incorporated into implant body 2502.

Implant body 2502 is an example of an implant body with a quadrilateral configuration with first and second parallel sides. In this example, the quadrilateral configuration does not include right angles. In alternative embodiments, it may have any other quadrilateral configuration.

Implant body includes a distal portion with a sharpened distal end 2517, which may be configured as any of the sharpened ends described herein, all of which are incorporate by reference into the description of FIG. 25.

FIG. 25 also conceptually illustrates exemplary lines L that are annotated in the top view of implant body 2502. Lines L are orthogonal to both a long axis LA of the implant body 2502, as well as to lumen axes ILA and SLA, as shown.

FIG. 26 is a top view of an exemplary implant 2600 with implant body 2602. Any suitable feature (including the absence of any features, such as a lumen) from any other implant body herein may be incorporated into implant body 2602.

Implant body 2602 is an example of an implant body with a quadrilateral configuration that does not include right angles. In alternative embodiments, it may have any other quadrilateral configuration.

Implant body includes a distal portion with sharpened distal end 2617, which may be configured as any of the sharpened ends described herein, all of which are incorporate by reference into the description of FIG. 26.

FIG. 26 also conceptually illustrates exemplary lines L that are annotated in the top view of implant body 2602. Lines L are orthogonal to both a long axis LA of the implant body 2602, to lumen axes ILA and SLA, as shown, as well as to a direction or trajectory of implantation.

FIGS. 27A and 27B illustrate a top view and distal perspective view of exemplary SI joint stabilizing implant 2700, which may understandably incorporate any other feature of any implant herein even if not expressly described with respect to FIGS. 27A and 27B. For example, implant 2700 includes implant body 2702 that includes ilium region 2704 and 2706, and sharpened distal end 2717 with a tapered configuration, as shown. In this embodiment, sharpened distal end 2717 has a general concave configuration, as shown. Sharpened distal end 2717 includes a top region that extends downward and distally from a top portion of the implant body, and a bottom region that extends upward and distally from a bottom portion of the implant body to form the tapered configuration. The top and bottom regions have general scallop configurations, as shown, as does the distal face of the sharpened distal end, both of which may enhance the ability of the sharpened distal end to cut or penetrate through bone.

FIG. 28 illustrates a top view of implant 1402 shown in FIG. 14. FIG. 28 illustrates conceptually how the outer profile of implant body 1402, in the top view, can be approximated to an approximated configuration 2802. FIG. 28 illustrates how implant body 1402 is described herein as an example of an implant body with a general quadrilateral configuration. In this example, the quadrilateral configuration does not include right angles, and is an example of an implant body with a rhomboid configuration, as shown by approximated configuration 2802. The general approximation shown in FIG. 28 is an example of how the implant bodies herein are described in terms of a general configuration, such as, without limitation, quadrilateral, rhomboid, parallelogram without right angles, etc.

Figure 31:
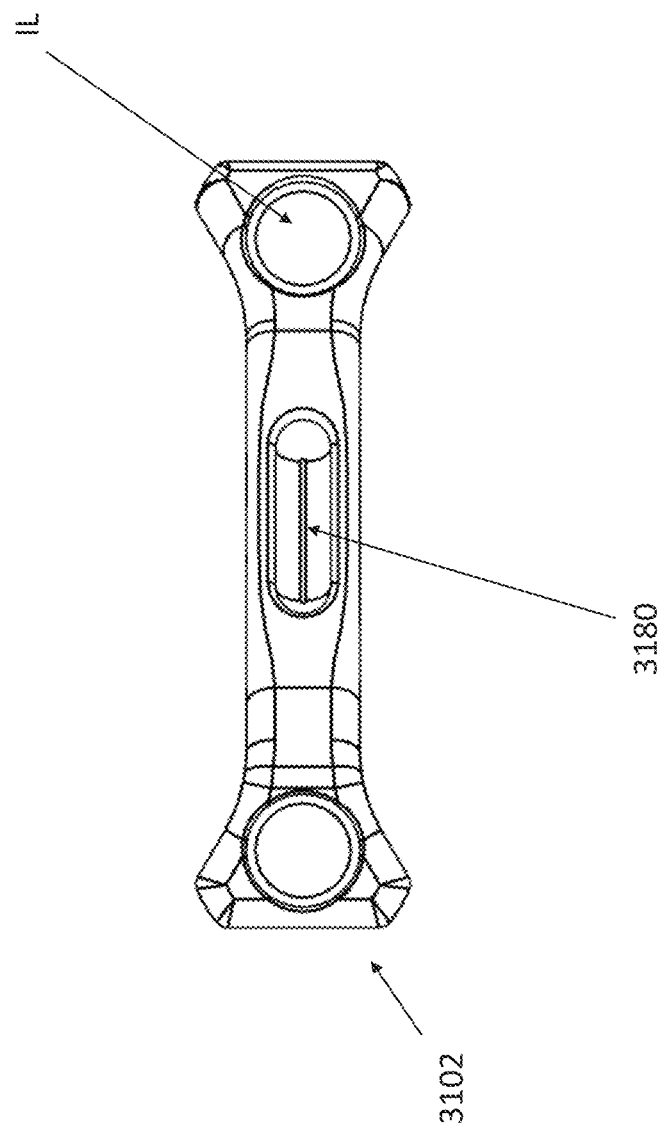

FIGS. 29-31 illustrate exemplary proximal or back ends of implant bodies 2902, 3002 and 3102, respectively, which may be included in any of the implant bodies herein. The proximal ends in FIGS. 29-31 are merely examples of proximal ends adapted to facilitate delivery of the implant with an impactor (examples of which are described below) FIG. 31 illustrates an exemplary implant body wherein the SL does not include a distal opening, an example of which is shown in FIGS. 22A and 22B.

FIG. 29 illustrates recessed (or depressed) impactor stabilizers 2980a and 2980b on either lateral side of channel 2928, which includes an internal thread 2983. Impactor stabilizers 2980a and 2980b are each shaped and positioned to receive therein a protrusion on the distal end of an impactor or other delivery tool, such as protrusions 5960 shown in FIG. 59D. The interface and engagement between the impactor and implant on both sides prevents rotation therebetween when the implant is loaded onto the impactor and when the implant is impacted.

Channel 2982 includes an internal thread, which is configured to engage with the external thread on implant securing member 5958 of the impactor to facilitate the releasable coupling between the impactor and the implant. The releasable coupling therebetween allows the implant to be axially secured to the impactor for impaction across the SI joint, and also allows the implant to be retracted proximally if needed by pulling on the impactor.

FIGS. 30 and 31 illustrate exemplary proximal ends that include recessed impactor stabilizers 3080 and 3180, respectively, which are sized and configured to interface with protrusions on a distal end of a delivery tool, such as an impactor herein. Stabilizers 3080 and 3180 are examples of stabilizers that are centrally located (in a lateral direction), and may extend across the long axis of the implant.

One aspect of the disclosure is related to methods of positioning an SI joint stabilizing implant across a SI joint from a dorsal approach. In these methods, the SI joint implant may be any of the SI joint implants herein unless the method is limited to one or more implants herein. The methods may include advancing an elongate ilium positioning guide from a dorsal starting point, such as starting point 1122 shown in FIG. 32A, and into an ilium of a subject. For example only, FIGS. 2A and 2B illustrate exemplary ilium guide 22, but other types of ilium guides may be positioned from a dorsal approach into an ilium of the subject. FIG. 32A also illustrates a general region 1120 into which any of the ilium guides herein may be started and advanced into an ilium to function as a guide for the SI joint implant. The methods herein may include engaging a guide interface member of the SI joint implant with a positioning guide to restrict movement of the implant with respect to the positioning guide in at least one direction. For example only, FIGS. 1A and 1B illustrate ilium guide interface member 18 of SI joint implant 14, but other interface members herein may be engaged with any of the guides herein to restrict movement of the SI joint implant with respect to the positioning guide in at least one direction. The methods may include, at a time subsequent to the engaging step, advancing the implant across the SI joint while guiding the implant with the positioning guide to implant the implant across the SI joint. The methods further include removing the positioning guide from the ilium and leaving the implant implanted across the SI joint. The methods may include advancing a positioning guide into an ilium between lateral and medial cortical walls of the ilium, descriptions and locations of which are generally known and shown generally in FIGS. 32A and 32B. In these methods, engaging the implant with an ilium positioning guide helps maintain the implantation trajectory and limits the extent to which the implant migrates towards the sacrum while advancing the implant across the SI joint.

Some methods may also include advancing a sacrum positioning guide into a sacrum of the patient, and further engaging a second guide interface member of the implant with the sacrum positioning guide. In these examples, the implant advancing step may occur while also guiding the implant with the sacrum positioning guide. In these examples, the method also includes removing the sacrum positioning guide from the sacrum. Any of the methods herein may include positioning a sacrum positioning guide into a sacrum before or after an ilium positioning guide is positioned in an ilium.

Methods herein may optionally include, prior to implanting the implant across the SI joint, interfacing a sharpened broach with one or more of the guides herein; advancing the sharpened broach over the one or more positioning guides towards the SI joint while guiding the broach with the one or more positioning guide; and creating a space for the SI joint implant with the sharpened broach. These methods may include removing the broach to allow dorsal access to the space. An implant may then be advanced over the one or more positioning guides as described elsewhere herein and implanted across the SI joint.

Depending on the implant being implanted across the SI joint, any of the methods herein may also include positioning a second ilium positioning guide from a dorsal approach into the ilium of a subject. These examples may also include engaging a second guide interface member of the implant with the second ilium positioning guide to further restrict movement of the implant with respect to the second ilium positioning guide in at least one direction.

Depending on the implant being implanted across the SI joint, any of the methods herein may optionally include positioning first and second sacral positioning guides from a dorsal approach into the sacrum of a subject. These examples may also include engaging first and second sacrum guide interface members of the implant with the first and second sacrum positioning guides to further restrict movement of the implant with respect to the first and second sacrum positioning guides in at least one direction.

Any of the individual method steps set forth herein may be combined with any other suitable method step or sequence of steps, unless the disclosure herein indicates to the contrary.

As is described above, an aspect of this disclosure is related to methods of positioning a sacro-iliac ("SI") joint stabilizing implant across a SI joint from a dorsal approach. An additional aspect of this disclosure is delivery tools that facilitate the delivery of one or more guides into the ilium and/or sacrum, and the methods of delivering the one or more guides into the ilium and/or sacrum. The disclosure that follows is related to those methods and delivery tools, and may be incorporated into any of the other disclosure herein. For example, methods and delivery tools herein may include and be adapted for advancing an elongate ilium positioning guide from a dorsal approach into an ilium of a subject, engaging an ilium guide member of a SI joint stabilizing implant with the ilium positioning guide to restrict movement of the implant with respect to the ilium positioning guide in at least one direction, advancing the implant across the SI joint while guiding the implant with the ilium positioning guide, and removing the ilium positioning guide from the ilium. The disclosure that follows provides merely exemplary and illustrative additional steps that may be incorporated into any of these methods. It is fully understood that these steps are illustrative, may be optional, and are not limiting the general methods set forth herein. It is also fully understood that the order of one or more of the steps set forth herein may be changed. The method steps that follow may refer to one or more delivery devices, examples of which are shown in FIG. 33 (e.g., impactor, positioning template, pin guide, guide pins, trephines, etc.). It is understood that the names of these delivery devices are not necessarily limiting, and they instead may be described or characterized by the one or functions they provide during the procedure. For example, a guide pin may instead be considered more generally as a positioning guide or simply a guide for the implant. A parallel pin guide herein may also be referred to as a pin guide herein.

Methods herein may include one or more steps to ensure a proper trajectory for the implant. The one or more positioning guides (e.g., guide pins) herein may help facilitate the desired trajectory from the dorsal approach. Methods herein may also include one or more steps to properly determine a starting point or location for the one or more positioning guides. The methods herein may further include one or more steps to advance the positioning guides along a proper trajectory, which may help maintain a desired or proper trajectory for the implant when advanced distally relative to the positioning guide(s). Merely exemplary steps that may be performed to position one or more positioning guides and advance an implant in a dorsal approach are set forth below, and are made in reference to FIGS. 34A-38.

Figure 34A:
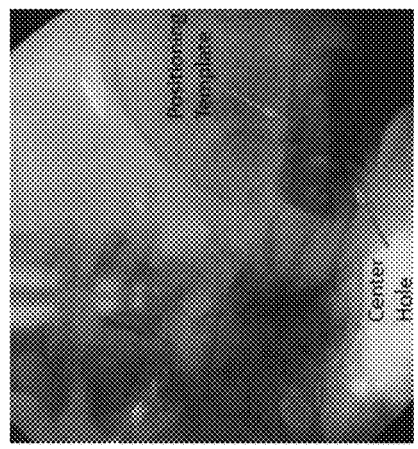
FIGS. 34A, 34B, 34C, 34D, 34E and 34F illustrate exemplary radiograph imaging of an SI joint region and exemplary steps in a procedure.
Figure 34B:
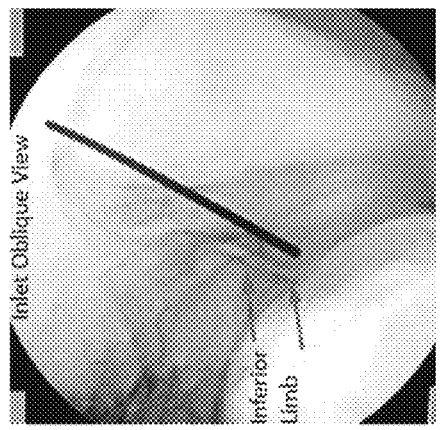
Figure 34C:
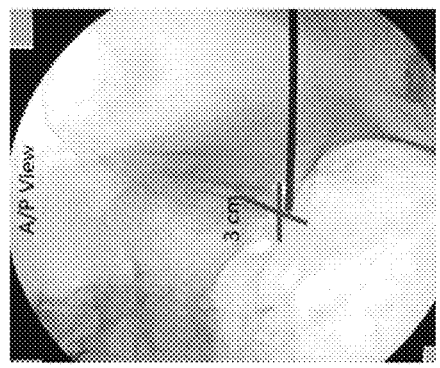
Figure 34D:
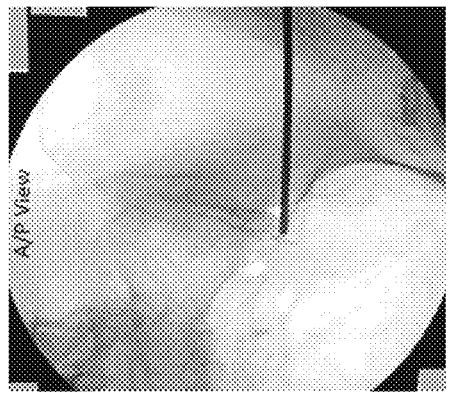
Figure 34F:
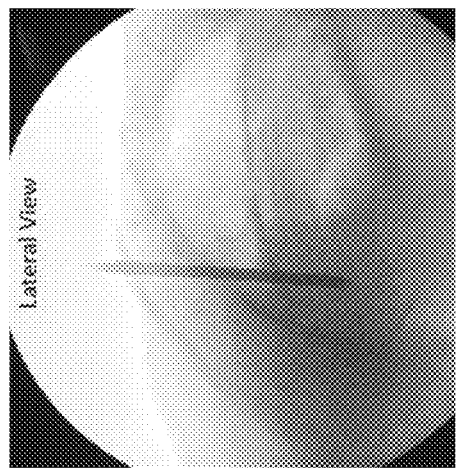
Figure 34E:
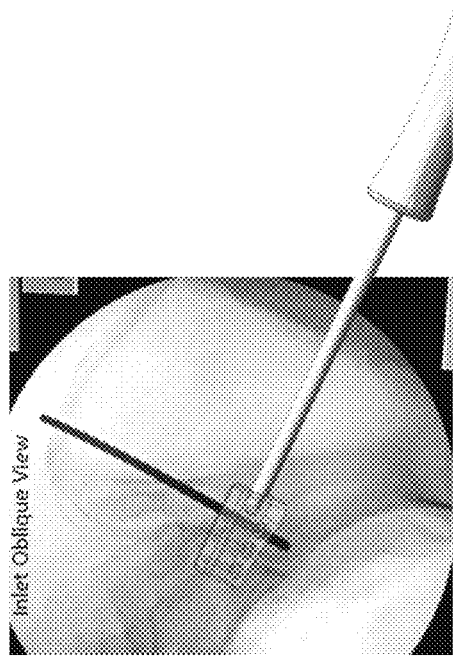
Figure 35B:
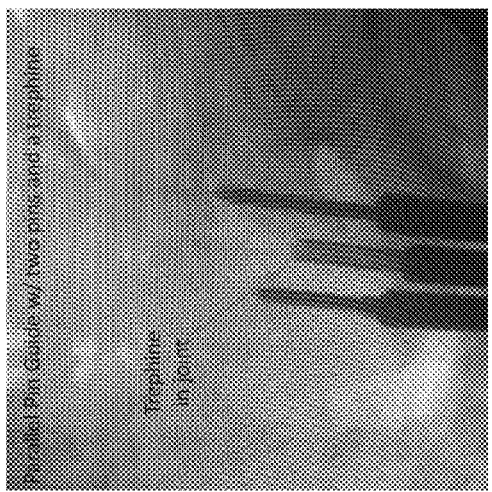
FIGS. 35A, 35B and 35C illustrate an exemplary procedure that includes the use of a pin guide and one or more pins.
Figure 35A:
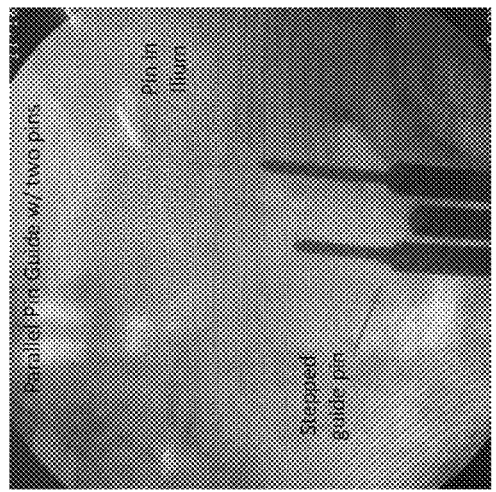
Figure 35C:
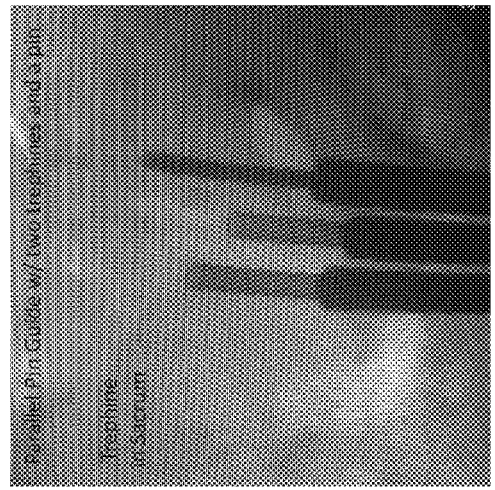

A patient may be positioned in a prone position to facilitate the dorsal approach and dorsal entry. Radiograph imaging may be performed to obtain an A/P (anteroposterior) view of the SI joint region, as shown in FIG. 34A. The inferior joint aspect of the SI joint may be localized. A visual marking may be made on the skin (e.g., with a marker), optionally about 1 cm proximal to the end of the joint, which can generally indicate an implant insertion location, such as shown in FIG. 34B. A second visual skin marking may be made, which may be 3 cm long or about 3 cm long, in line with the SI joint bifurcating the transverse skin mark, such as shown in FIG. 34B. A skin incision may then be made along the second visual skin marking An inlet oblique view may then be obtained, which may provide a view of the inferior limb of the articular joint, such as shown in FIG. 34C. A positioning template, such as the example shown in FIG. 33, may be placed in line with the transverse skin visual marking, and as represented in the view of FIG. 34D. It is of note that the methods herein may use only one positioning guide (e.g., pin), and the methods herein that use three are exemplary. The center hole or aperture in the positioning template may be positioned over the SI joint. The positioning template may be used to properly position one or more guide pins at one or more desired entry or starting point locations, and is illustrated in place in FIG. 34E (to illustrate the position relative to the view that is shown). Any of the methods herein may further include positioning a guide pin through the positioning template into the Ilium, optionally through an ilium aperture in the template, which may be one or one, two, or three apertures in the template. The guide pin may have a sharpened distal end to help advance the guide pin. A sharp ilium guide pin may be replaced with a blunt ilium pin. The methods herein may further include aligning the pin, optionally in the inlet oblique view, so that it is parallel to the inferior aspect of the SI joint. The pin may be seated in the ilium and advanced, optionally 1 cm or about 1 cm. A lateral view may then be obtained, such as in FIG. 34F, and the ilium guide pin may be advanced, such as, for example only, 4 cm or about 4 cm.

The following steps are understood to be optional, and not all steps may need to be performed depending on the implant and the particulars of the procedure. For example, one or all of the following steps may not be performed if the method does not utilize more than a single guide pin (e.g., an ilium guide pin). The description that follows is made in reference to FIGS. 35A-35C, but it is fully understood that one or more of these steps may occur in combination with one or more of the steps described with respect to FIGS. 34A-34F. The methods may further include obtaining an Inlet Oblique View, and the positioning template may be removed from the patient. A pin guide, an example of which is shown in FIG. 33 and labeled parallel pin guide (which can also be seen in FIGS. 35A-35C), may be advanced over the guide pin that is in the ilium. In the example in FIG. 33, the longer of the tubes of the pin guide may be advanced over the ilium pin, which can be seen in FIG. 35A. The methods herein may include advancing a guide pin (such as a stepped guide pin) into the sacrum through a sacrum guide tube of the pin guide, which can be seen in the view of FIG. 35A. The methods herein may include preparing a hole in the joint through a central lumen of the parallel pin guide, such as by drilling with a trephine through the center hole to a stop, such as into the joint approximately 30 mm, which can be seen in FIG. 35B. A broach may be used instead of a drill, for example, and it is understood that any of the methods herein may be performed completely without electrical power (e.g., without power tools). If a trephine is used, the trephine may be removed, a guide pin may be advanced through the central lumen of the pin guide. Performing this optional step may help prevent the pin guide from rotating while placing a sacral trephine. The optional sacral guide pin may be removed and a hole may be prepared in the sacrum, such as by drilling into the sacrum with the trephine, such as about 30 mm, and example of which can be seen in FIG. 35C. The methods herein may include removing an optional sacral trephine and placing a blunt pin in the sacrum through the sacrum tube of the pin guide (not shown). The pin guide may be removed, and a central guide pin, if utilized, may be removed. A hole may optionally be prepared in the ilium, such as by drilling with a trephine over the iliac pin, such as up a line (e.g., 30 cm) on the trephine. A broach may alternatively be used without power to prepare an ilium hole. A trephine may be removed from the ilium, and in this merely exemplary embodiment, iliac and sacral guide pins are left behind in the patient to help guide the implant during implantation. It is again noted that any of the methods herein may utilize only one positioning guide (e.g., one guide pin), such as an ilium positioning guide.

Figure 37B:
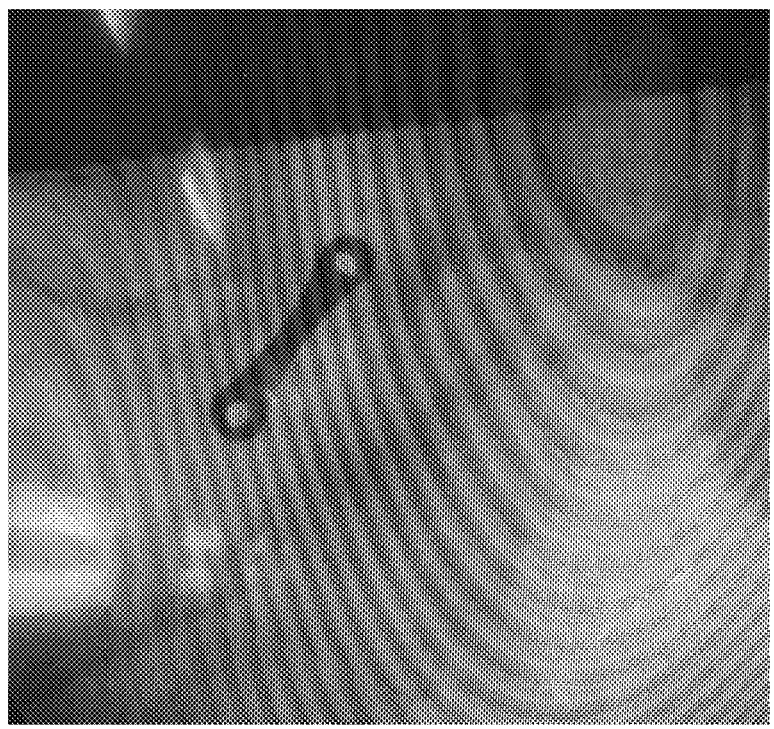
FIGS. 37A and 37B show exemplary radiograph imaging to confirm proper implant position.
Figure 37A:

With specific but not limiting reference to exemplary implant 1300 from FIGS. 11A and 11B, the implant may then be engaged with the guides (e.g., pins) by advancing the lumens 1305 and 1307 over the respective guide pins. The ilium portion, which in this example does not extend as far proximally as the sacrum portion, is engaged with the ilium positioning guide and the implant 3610 is advanced over the pin guides, as shown in FIG. 36. An impactor 3600 (or other similar tool that can be used to advance the implant) can be advanced over the guide pins behind implant 3610 until it engages the implant at location 3620. As shown in FIGS. 33 and 36, the distal end of the impactor can have a configuration that is shaped to mate with the configuration of the proximal end of implant 3610, and also to allow the impactor to apply a distally directed force to the implant. In this example, the impactor distal end is also stepped to match the configuration of the proximal end of implant 3610. Implant 3610 may include any of the features of any of the implants herein. Impactor 3600 includes a plurality of pin guides 3602 as well, sized and configured to receive therein the guide pins 3640, which in this embodiment are lumens extending axially along lateral portions of the impactor, as shown. This allows the impactor 3600 to be advanced over the guide pins and to be aligned with implant 3610 to facilitate distal advancement of the implant 3610 by applying a distally directed force on impactor 3600 (directly or indirectly applying the force). The implant may be advanced to the desired depth by applying the force on the impactor (e.g., with a mallet). The impactor and guide pins may be removed, leaving the implant behind implanted in the patient across the SI joint. A proper implant position may be confirmed, such as shown in the views of FIGS. 37A, and 37B.

It is understood and stated again that the methods of implantation herein may include using as few as one, and optionally two, three or more guide pins.

Any of the methods of implantation herein may be performed solely under an inlet radiographic view. Any of the methods of implantation herein may be performed solely under an inlet or inlet oblique radiographic view.

Any of the methods of implantation herein may be performed without electric power (e.g., manual power only). Any of the methods of implantation herein may be performed with electric power (e.g., including use of an electric drill for one or more steps, examples of which are set forth herein).

Any of the methods steps herein that include preparing a hole may be performed by drilling a hole. Any of the methods steps herein that include preparing a hole may be performed by manually creating a hole, such as with a broach. Broaches herein may also be used to create a channel within the bones from one guide pin to the other to accept the entire implant.

Any of the methods herein may include a removable pin that threads into the sacral tube of the pin guide. This may provide an added advantage of not risking distal advancement beyond a desired location, which may reduce the risk of damaging sensitive tissue.

Figure 40:
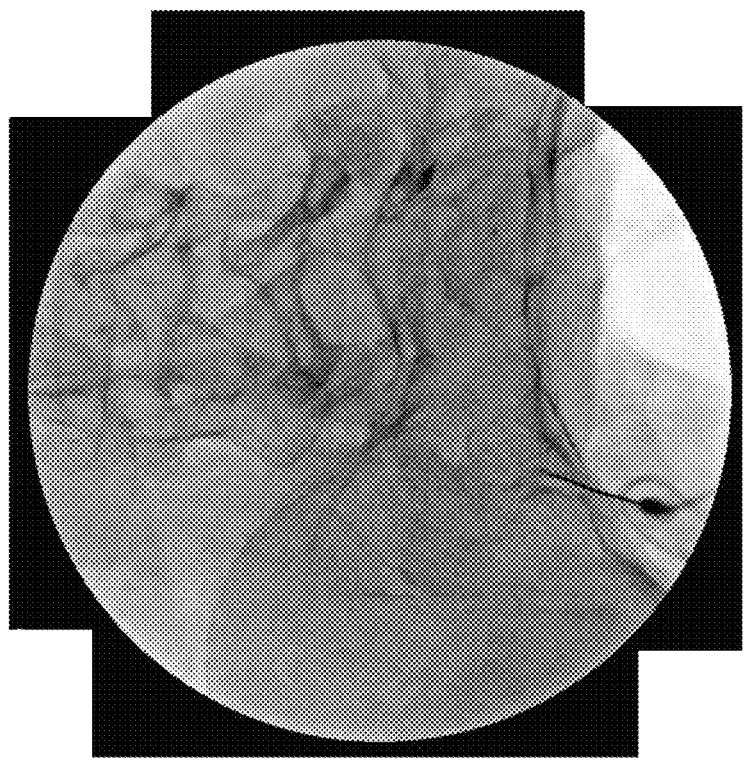
Figure 42B:
FIGS. 42A and 42B illustrate exemplary steps of placing an exchange pin and creating a linear skin marking along the exchange pin.
Figure 42A:
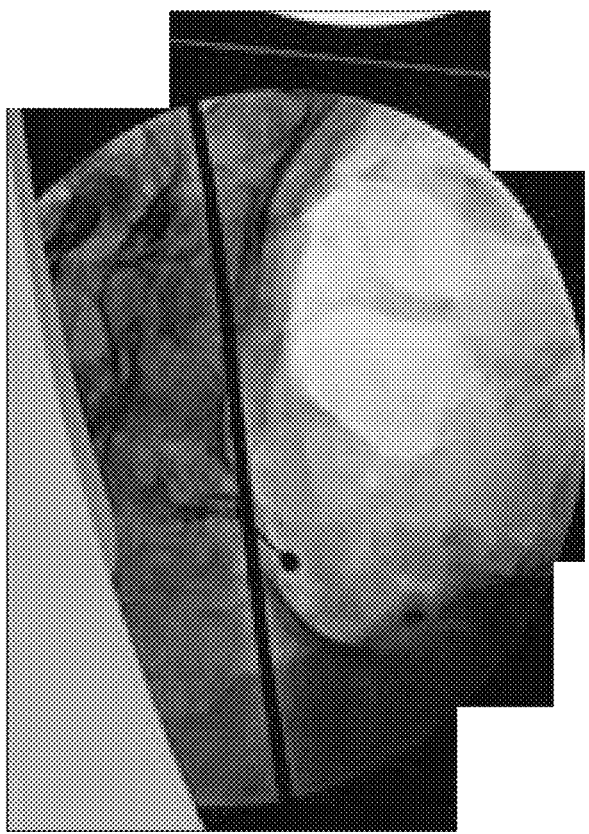
Figure 43:
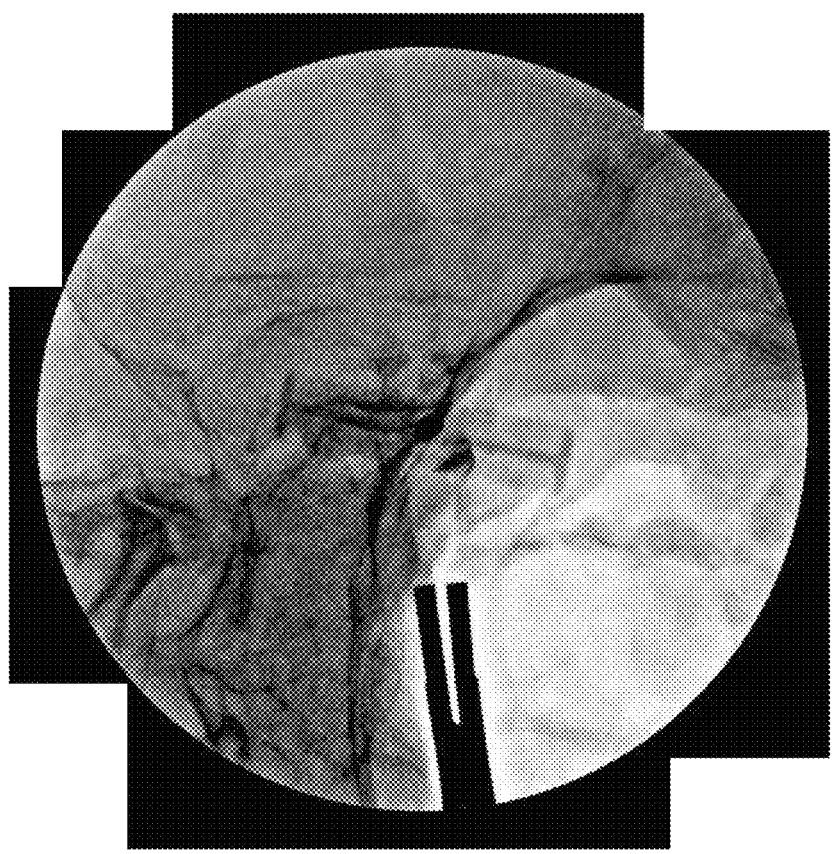
FIG. 43 illustrates placement of a needle.
Figure 44:
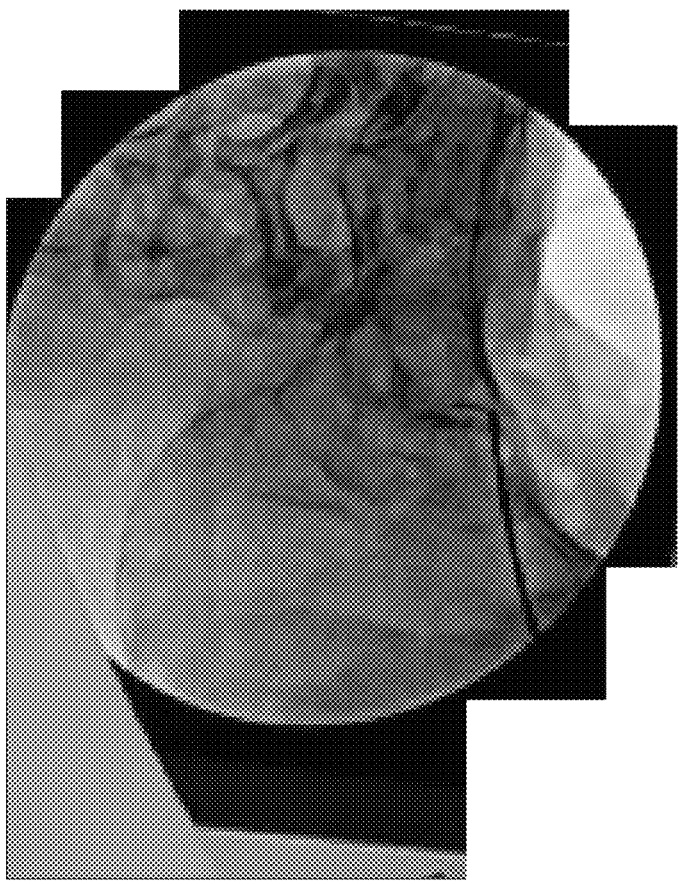
FIG. 44 illustrates a nitinol wire after a needle has been removed.

The disclosure that follows provides additional and exemplary methods and steps that may be included when preparing for the implantation and implanting any of the SI joint implants herein from a dorsal approach. The disclosure that follows describes a merely exemplary method, not all steps of which are necessarily required (and the order of some steps may be changed), and refers generally to FIGS. 40-55B. Suitable method steps below may, however, be incorporated into alternative methods described herein, and vice versa. An exemplary method of placing a plurality of guide pins may include, in an inlet oblique view such as is shown in FIG. 40, optionally placing a needle in the SI joint, as may occur in an SI joint injection. The method may optionally include injecting a contrast media such as Omnipaque with the needle to ensure the needle is in the SI joint, which can be viewed in, for example, an inlet oblique view and/or a lateral view as shown in FIGS. 41A and 41B. As shown in the radiographic view of FIG. 42A, the method may include placing an exchange pin along the skin over the sacral promontory. The method may include creating a linear skin marking along the exchange pin, as shown in FIG. 42B. Additional skin markings may be made on either side of the SI joint, such as about 2 cm on either side of the SI joint, which may be used for creating an incision, which is described below. The method may include removing the back end of the needle, including the luer lock, and placing a Jamshidi™ needle over the needle, as represented in FIG. 43. The method may include removing the original needle and replacing it with a nitinol wire through the Jamshidi™ needle and into the SI joint. The Jamshidi™ may then be removed, leaving the nitinol wire in the SI joint, as shown in FIG. 44.

Figure 45:
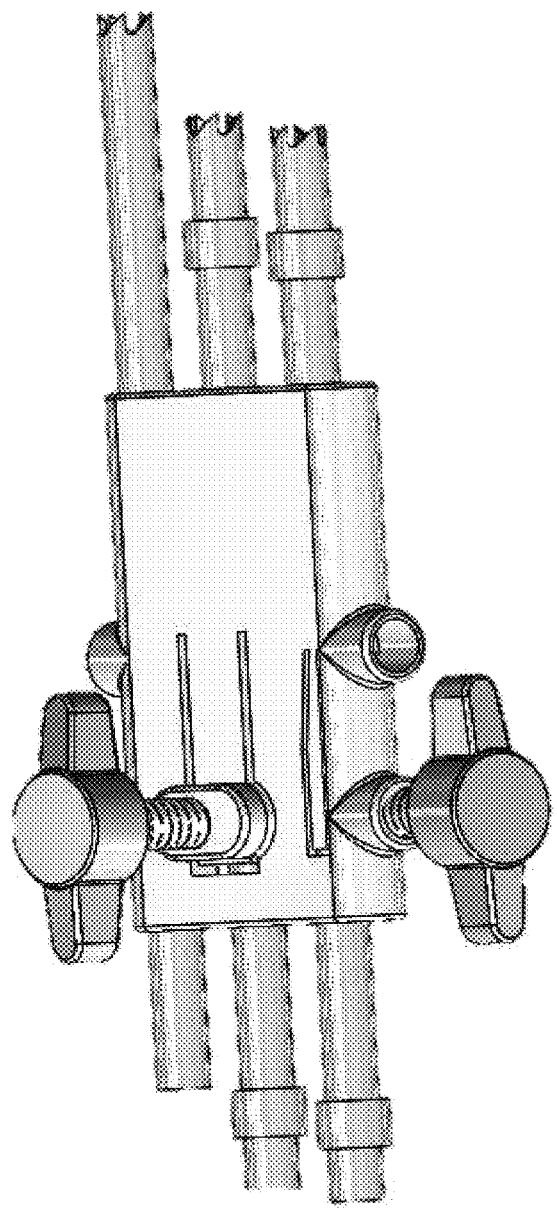
FIG. 45 illustrates an exemplary pin guide with a plurality of channels.
Figure 46B:
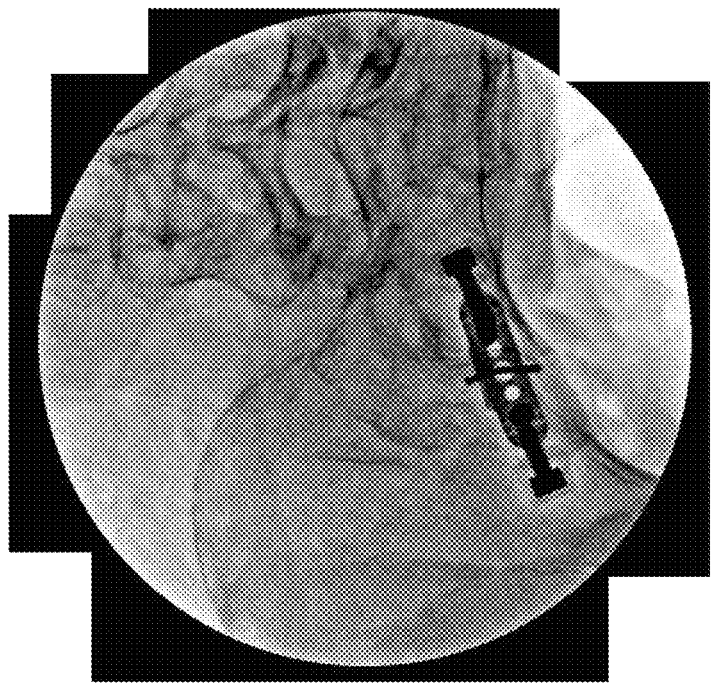
FIGS. 46A and 46B illustrate placing a central lumen of a pin guide over the wire from FIG. 44.
Figure 46A:

The method may also include making an incision along the linear marking between the additional markings that were made on either side of the SI joint, such as an incision about 4 cm in total length (e.g., 2 cm on either side of the joint). The method may also include placing a pin guide over the nitinol wire. Exemplary pin guides are shown in FIGS. 33 and 45, both of which are examples of pin guides that include a plurality of tubes or channels as shown, and are also examples of pin guides that include three tubes, channels, or lumens. In an exemplary method, the center of three channels may be placed over the nitinol wire, which is shown in FIG. 46A and the radiographic image of FIG. 46B. Pin guide adjustment may be made under radiographic imaging such as fluoroscopy to obtain the appropriate pin guide positioning. The exemplary pin guide shown in FIG. 45 includes actuators that in this example include knobs that can individually be tightened against one of the three channels or tubes to prevent them from moving axially relative to the pin guide main body. Releasing the engagement can be performed to allow any of the tubes to be individually moved axially relative to the main body, after which time their relative axial positions can again be fixed by rotating the knobs until the threaded element engages the particular tube/channel. A variety of alternative mechanisms to both maintain axial position in a first configuration yet allow for axial movement in a second configuration may also be used. As used herein, any of the pin guide tubes may also be referred to herein as pin guide channels, both of which are understood to define a pin guide lumen therethrough.

Figure 47:
FIG. 47 illustrates a pin being positioned through the sacral cortex with a mallet.

The method may also include placing a sacral tube of the pin guide down to sacral bone. The sacral-side knob may then be tightened to secure the sacral tube of the pin guide on the sacrum. The method may include placing a pin (e.g., a 3.2 mm pin) through the sacral tube of the pin guide through sacral cortex, but not to depth. The pin may be positioned through the sacral cortex with a mallet, for example, as is shown in FIG. 47.

Figure 48B:
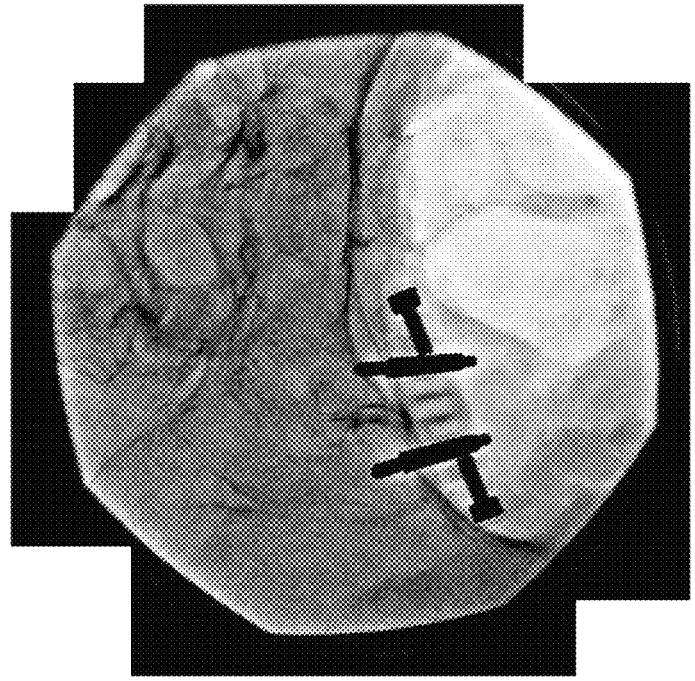
FIGS. 48A and 48B illustrate an ilium pin positioned through ilial cortex with a mallet.
Figure 48A:
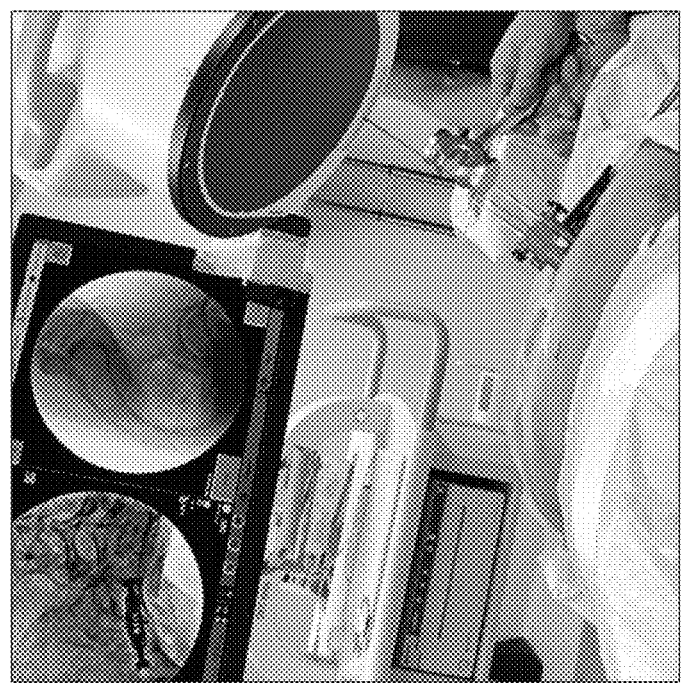

The method may also include distally advancing an ilium tube of the pin guide down and into contact with iliac bone, which may be performed before or after the sacral tube is advanced distally to sacral bone. The ilium-side knob on the pin guide may then be tightened to secure the ilium tube of the pin guide on the ilium. The method may include placing a pin (e.g., a 3.2 mm pin) through the ilium tube of the pin guide through ilial cortex, but not to depth, which may be performed before or after the sacrum pin is advanced through sacral cortex. The ilium pin may be positioned through the ilial cortex with a mallet, for example, as shown in FIG. 48A and the radiographic image of FIG. 48B. At this exemplary embodiment, guide pins are positioned in both the sacrum and ilium (which may be positioned therein in either order).

Figure 49B:
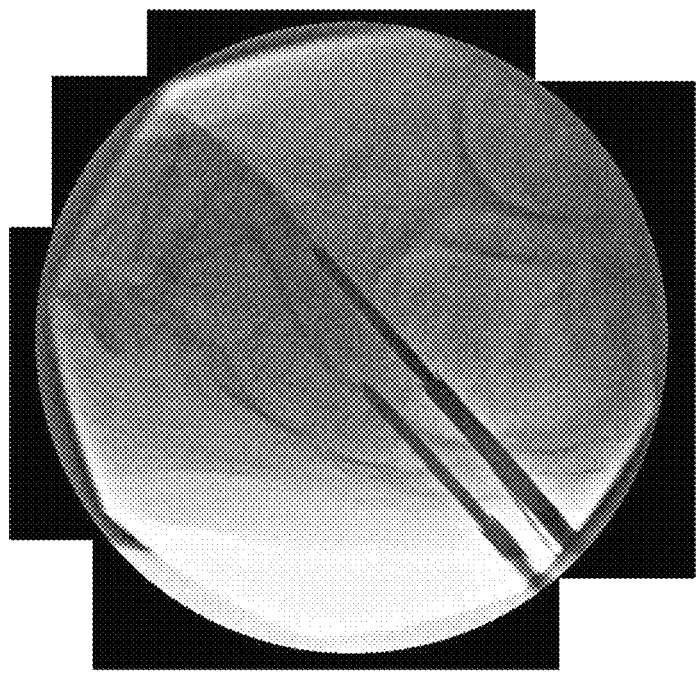
FIGS. 49A and 49B illustrate taking a lateral radiographic image.
Figure 49A:

The method may include providing or taking a lateral image, as shown in FIGS. 49A and 49B, and distally driving the sacrum and ilium pins (in either order, or only one pin if the procedure utilizes only a single pin) to depth in the lateral view. The method may preferably include not distally advancing the guide pins passed the alar line, as shown. At this time, the elongate guiding wire (e.g., nitinol wire) may be removed from the optionally center channel of the pin guide.

Figure 51:
FIG. 51 illustrates placement of a trephine over a pin.
Figure 50:
FIG. 50 illustrates an optional step of drilling a hole through a center channel of an exemplary pin guide.

A hole may optionally then be drilled through a center channel of the pin guide, as shown in FIG. 50. The pin guide may then be removed from the patient, leaving the ilium and sacrum pins in place in the ilium and sacrum, respectively. Ilium and sacrum bone may then be cut or removed using a cutting instrument such as a trephine placed over the ilium and sacrum pins, as shown in FIG. 51. Preferably only cortex bone is cut with the cutting instrument.

Figure 52:
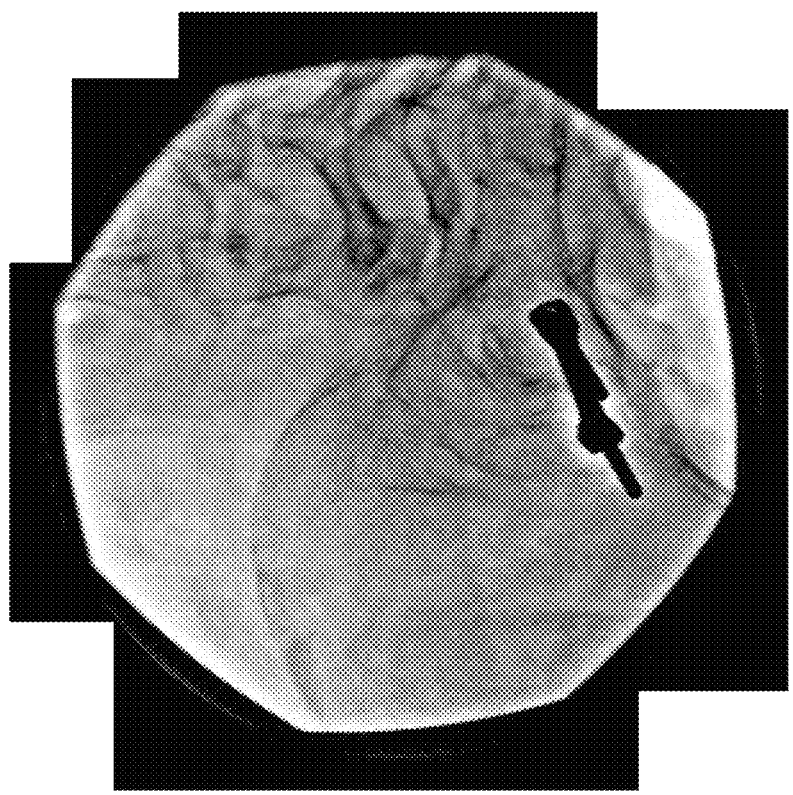
FIG. 52 is a radiographic image of an implant engaged with pins that have been placed in the sacrum and ilium.
Figure 53B:
FIGS. 53A and 53B shows an implant impacted to depth across the SI joint.
Figure 53A:
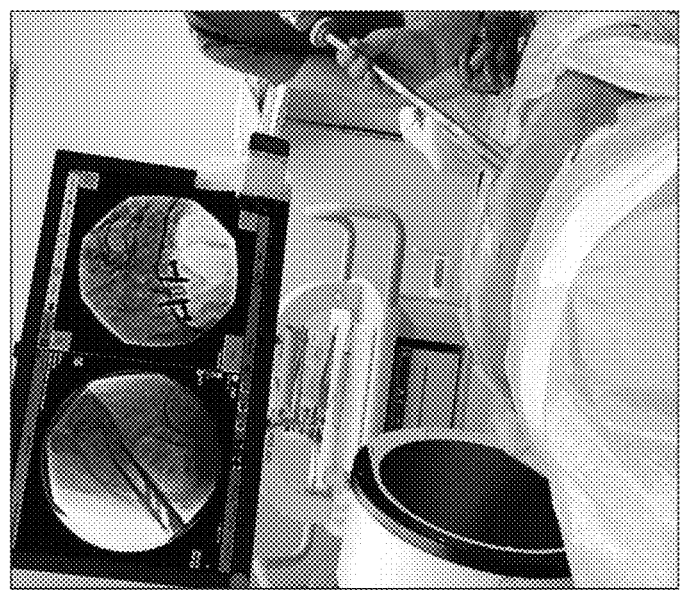
Figure 54:
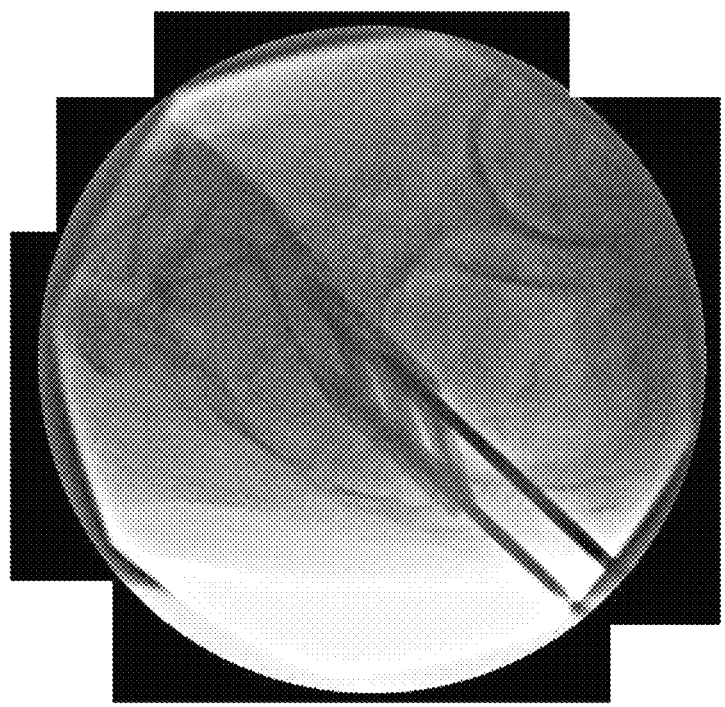
FIG. 54 is a radiographic image showing the pins being removed from the sacrum and ilium.

With guide pins in place in the ilium and sacrum, the SI joint implant can be engaged with the guide pins, details of which are described herein, an exemplary step of which is shown in the radiographic image of FIG. 52. The implant is then impacted to depth (e.g., using an impactor such as shown in FIG. 33 or other similar impactor) across the SI joint while being guided by the guide pins, as shown in FIGS. 53A and 53B, and additional details of which are set forth above. After the implant is delivered to the desired position across the SI joint, the impactor and the guide pins may then be removed, which is shown in FIG. 54 when the guide pins are being removed. An additional lateral view (FIG. 55A) and an outlet view (FIG. 55B) may be obtained to visualize the implant position across the joint.

Figure 55B:
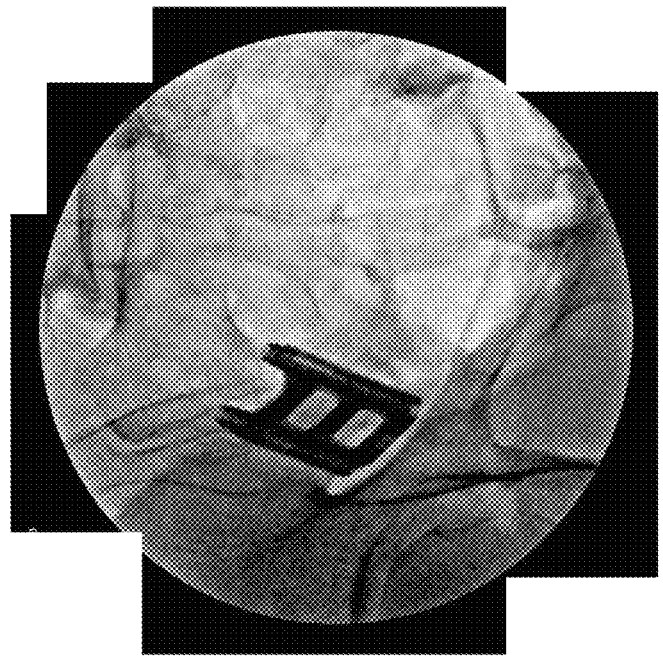
FIG. 55A is a lateral view and FIG. 55B is an outlet view showing the implant implanted across the joint.
Figure 55A:
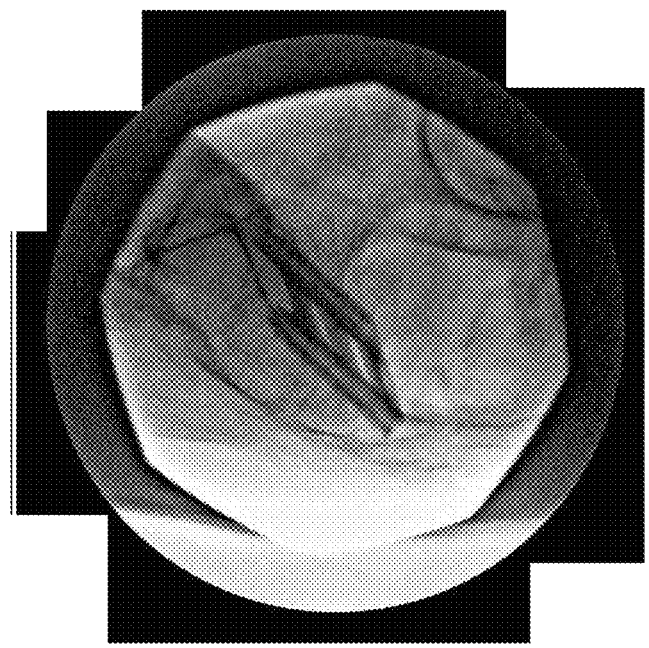

This exemplary method includes implanting an SI joint implant that comprises larger and fewer fenestrations than the implant in FIG. 11A, which can be seen in the radiographic image of FIG. 55B. This method also includes implanting an implant that includes a proximal region that does not include a sacrum region that extends further proximally than an ilium region, in comparison to the implant in FIG. 11A. As shown in FIG. 55B, the implant in this embodiment also includes a distal central region with at least some degree of curvature, which is described in more detail above with respect to the implant in FIGS. 11A and 11B. Additionally, the implant shown in FIG. 55B also includes a sharpened distal central region, examples of which are described herein.

The disclosure that follows provides additional exemplary delivery tools (e.g., a pin guide) sized and configured for positioning one or more guides (e.g., guide pins) into an ilium and/or sacrum. The disclosure that follows additionally provides exemplary tools for advancing implants over the one or more guides and into position across the SI joint. It is understood that aspects of methods that follow may be incorporated into other methods of guide pin placement herein, and vice versa. It is also understood that features of delivery tools that follow may be incorporated into other suitable delivery tools herein, and vice versa. The methods and delivery tools that follow may be used to delivery one or more of the suitable implants herein. The disclosure below describes delivery tools in the context of their methods of use with the exemplary methods.

In the dorsal approach with the patient prone (with their back facing up), an incision can first be made proximate the SI joint, followed by retracting soft tissue to expose the underling bone and provide access to the joint.

FIGS. 56A and 56B illustrate an exemplary pin guide 5600 that can be used in methods herein to place one or more guides (e.g., guide pins) into an ilium and/or a sacrum from a dorsal approach. Pin guide 5600 includes pin guide body 5602 with an ilium guide portion 5604 that is optionally longer than sacrum guide portion 5606. Ilium guide portion 5604 includes a lumen 5605 sized and configured (optionally cylindrical) to receive one or more elongate delivery tools, examples of which are described below. Sacrum guide portion 5606 includes a lumen 5607 sized and configured (optionally cylindrical) to receive one or more elongate delivery tools, examples of which are described below. Body 5602 further includes first and second laterally extending attachment members 5610a and 5610b, which are configured to interface with an optional elongate handle (described below), wherein the optional handle can be held by medical personnel and which can help maintain the position of pin guide 5600. The distal direction indicates the front of the pin guide 5600 that is first advanced into the patient. The pin guide may include a visual indicator that indicates if it should be used for right or left SI joint pin placement. For example, in this embodiment the pin guide includes a visual indicator that states Right or Left, but other indicators may be used.

FIGS. 56C and 56D illustrate perspective front and side views, respectively, of alternative pin guide 5600', which can be the same as pin guide 5600 in all other ways (and used in the same ways) except as described herewith. The same components are similarly labeled, such as body 5602 (FIGS. 56A, 56B) and 5602' (FIGS. 56C, 56D). Implant 5600' includes first and second central pins 5690a and 5690b, which may be permanently coupled with (attached to) body 5602'. Pins 5690a and 5690b are laterally aligned, with pin 5690a being superior to or above 5690b. Pins 5690a and 5690b extend to the same extent distally, as shown in FIG. 56D. Pins 5690a and 5690b are generally configured and positioned to be advanced across the SI Joint as pin guide is being moved distally towards the SI joint. Pins 5690a and 5690b extend further distally than other parts of pin guide and are the first portion of pin guide 5600' to engage with the SI joint. Pins 5690a and 5690b may, in some embodiments, extend from 10 mm to 20 mm distally from the pin lumens in body 5602'. Pins 5690a and 5690b have sharpened distal ends to pierce into joint tissue and help secure the pin guide relative to the Joint. As set forth herein, the pin guide may or may not include central joint pins 5690a and 5690b, although incorporating them may help secure the pin guide relative to the joint as the other one or more pins as advanced into bone.

Figure 57A:
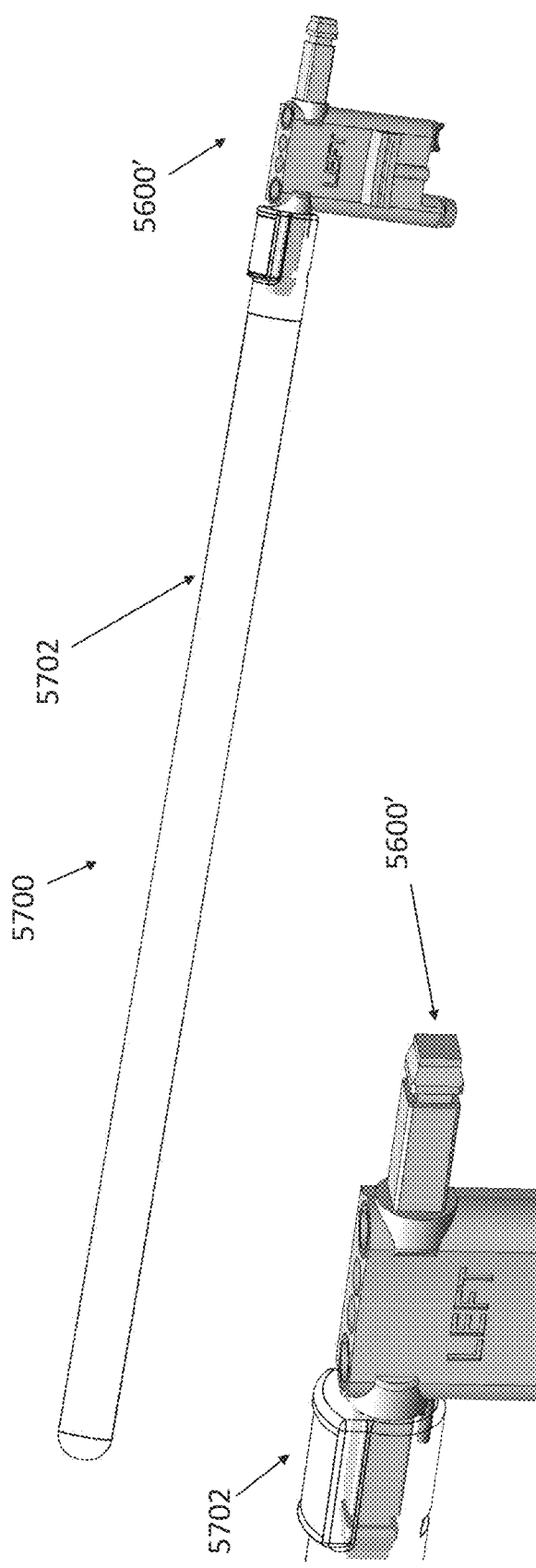
FIGS. 57A and 57B illustrate an exemplary handle secured to an exemplary pin guide.
Figure 57B:
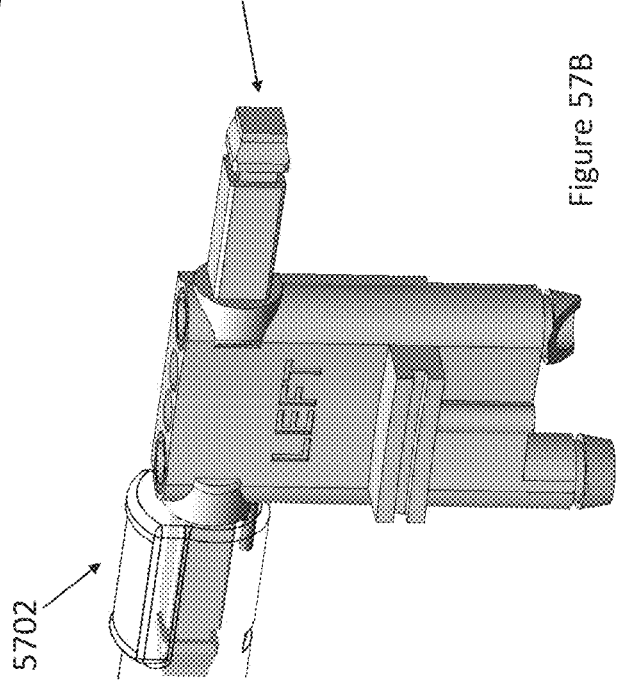

FIGS. 57A and 57B illustrate exemplary handle 5700 after it has releasably secured to one of the laterally extending attachment members. FIG. 57B is a close up view of the region where they are releasably coupled. Handle 5700 includes a channel at one end sized and configured to fit over and be secured to the attachment member. A variety of mechanisms may be used to secure the two components together, and in this example the attachment members include a detent or recessed region configured to receive a locking element within the channel of the handle. The handle is configured to be gripped or grasped by medical personnel, which may make it easier to maintain the position of the pin guide during the pin placement procedure. FIGS. 57A and 57B illustrate pin guide 5600', which has a visual of Left to indicate it is configured for pin placement in a procedure on a patient's left SI joint. The left and right pin guides may have the same features, but which are mirror images of each other so they can be used on the right or left side. Additionally, pin guides 5600 and 5600' are optionally longer on the ilium side, as shown. The optional handle may be attached to the pin guide prior to the following exemplary steps.

Distal tips of the optional pins 5690a and 5690b may then be centered within the SI joint, and the starting point is optionally about 1 cm superior from the ventral SI joint surface. Pin guide 5600' (or any other pin guide herein) may be tapped into the SI joint at the target anatomy, optionally about 1 cm superior from the ventral SI joint surface, and the distal tip of the pins 5690a and 5690b may be docked into the joint.

Figure 64:
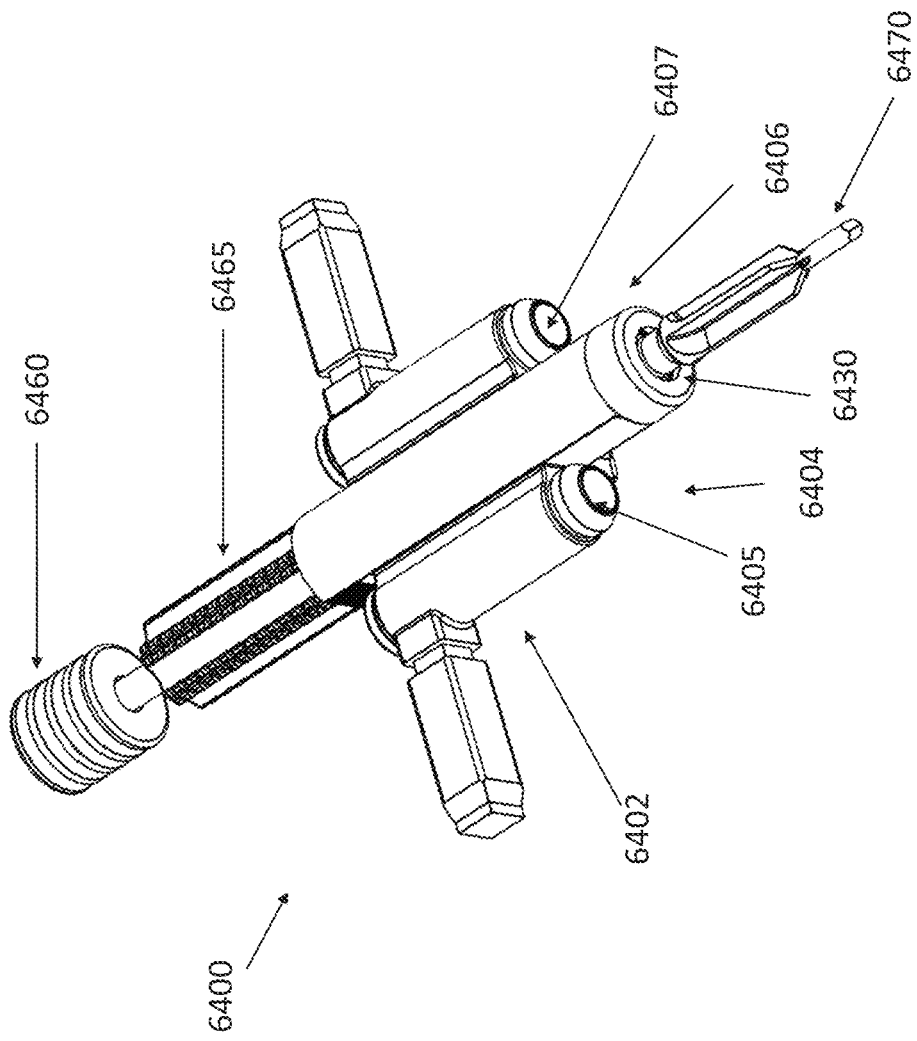
FIG. 64 illustrates an exemplary pin guide.

FIG. 64 illustrates an exemplary pin guide 6400, which is similar to pin guides 5600 and 5600' but with differences set forth herein. Any suitable feature of pin guide 5600 or pin guide 5600' may be incorporated into the disclosure of FIG. 64 unless indicated to the contrary herein. Pin guide 6400 includes body 6402, ilium guide portion 6404 with lumen 6405, and sacrum guide portion 6406 with lumen 6407. Sacrum guide portion 6406 can extend as far distally as ilium guide portion 6404, as shown.

Unlike with pins 5690a and 5690b in FIGS. 56C and 56D, which have a fixed orientation relative to pin guide 5602', pin guide 6400 is adapted such that distal pin 6470 can move relative to the pin guide body 6402 when pin guide 6400 is in a first state, and then can be locked in place relative to pin guide body 6402 (or at least become much more relative thereto) when pin guide 6400 is in a second state. Particularly, and in this embodiment, when stabilizer 6465 is in a first state, pin 6470 can be moved 360 degrees relative to the distal end of the body 6402 from which pin 6470 extends. By tightening stabilizer 6465 to a second state, however, the orientation of pin 6470 relative to body 6402 can be locked in place or at least becomes much more difficult to move relative to body 6402. By allowing more relative movement between the pin 6470 and body 6402 in a first state, yet allowing the orientation of the pin 6470 to be secured relative to the body 6402 in a second state, the pin 6470 can first be placed into the joint, and then the orientation of the pin guide body 6402 can be fine-tuned as desired by moving it relative to the already placed pin. The pin guide body 6402 can thus be moved relative to the set pin until the body lumens 6405 and 6407 are aligned with the desired trajectories for the ilium pin and the sacrum pin, which are subsequently placed as is set forth herein. When the pin guide body 6402 has been moved to the desired orientation relative to the joint and bones, stabilizer can then be actuated to cause the position of the pin guide body 6402 to be set in place (or least more secured) relative to the pin and the joint in which the pin is placed. This arrangement thus allows for fine tuning the position and orientation of the guide body relative to the pin and joint after the pin has already been placed in the joint, yet further allows the guide body position to be set once it's been moved into the desired orientation.

In this exemplary embodiment, distal pin 6470 in FIG. 64 may be fastened or coupled to pin guide 6400 via a spherical ball-and-socket that allows the user to place the pin 6470 in the joint, and then fine tune the positioning of the sacrum guide portion 6406 and ilium guide portion 6404 over the respective bones as described above.

In use, the mounting pin 6470 may first be placed in the joint in approximately the correct location. The pin guide 6402 positioning can be further refined by decoupling the mounting pin 6470 from the pin guide 6402 by pulling the most proximal knob 6460 further proximally. The resistance of the ball-and-socket joint can be increased and decreased by turning the threaded stabilizer 6465 just distal to the proximal knob 6460. The sacrum and ilium guide portions 6406 and 6404 can be aligned over the respective bones, and the ball-and-socket joint resistance can be increased by turning threaded stabilizer 6465 clockwise, which limits movement between pin 6470 and body 6402. Ilium guide portion 6404 includes a lumen 6405 sized and configured (optionally cylindrical) to receive one or more elongate delivery tools, examples of which are described above with respect to FIGS. 56A-56D. Sacrum guide portion 6406 includes a lumen 6407 sized and configured (optionally cylindrical) to receive one or more elongate delivery tools, examples of which are described above. After the sacrum and ilium guide portion positions are set, positioning of the guide pins such as 5830 and 5860 described herein may proceed, examples of which are described herein. All other uses of the pin guides herein may be applicable to pin guide 6400 shown in FIG. 64.

Figure 58A:
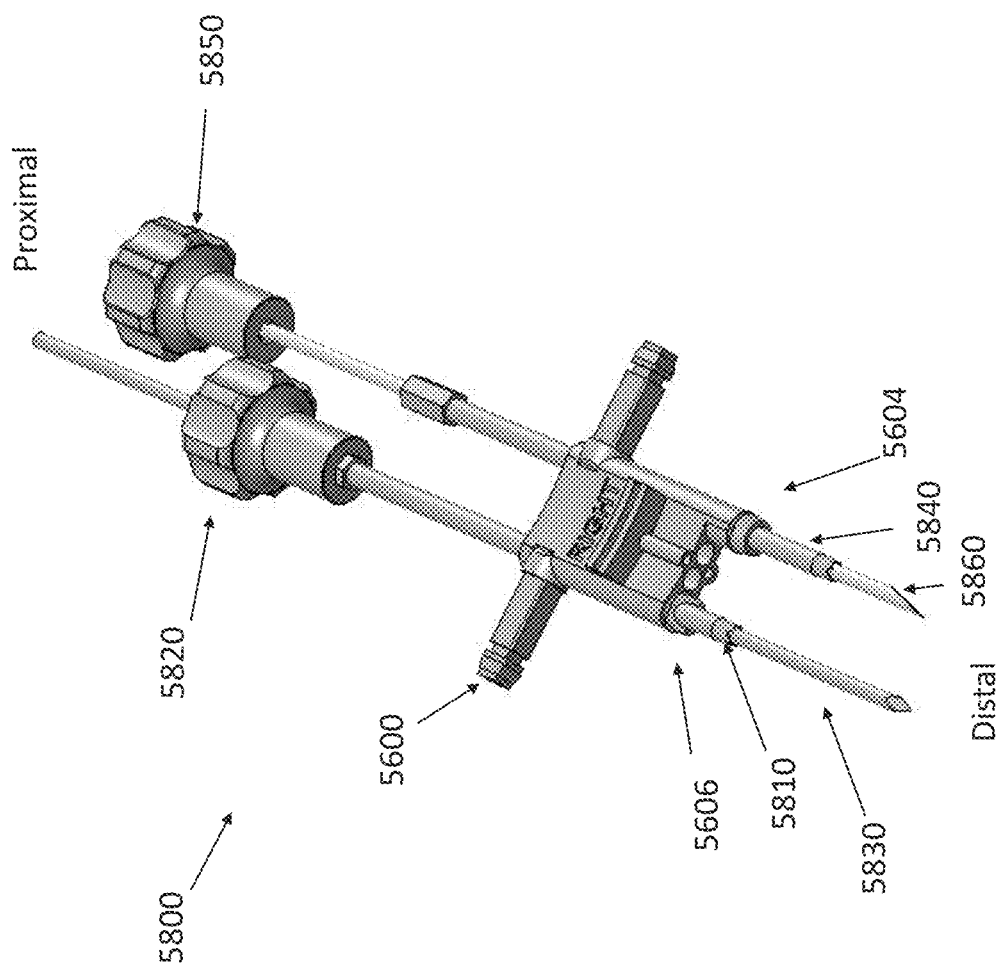
FIGS. 58A, 58B and 58C illustrates tool for and methods of positioning ilium and sacrum pins.
Figure 58C:
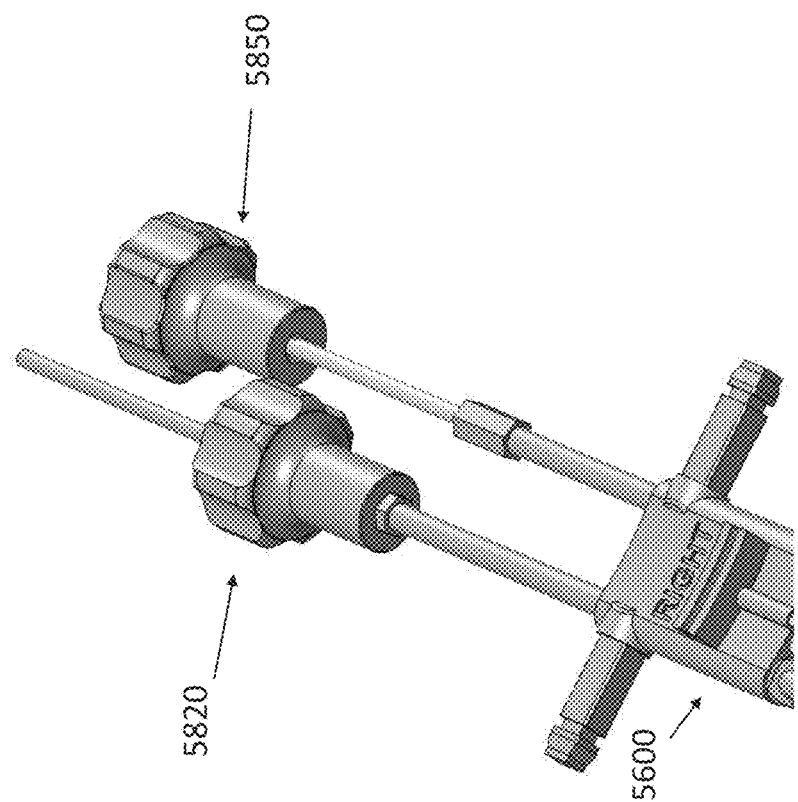
Figure 58B:
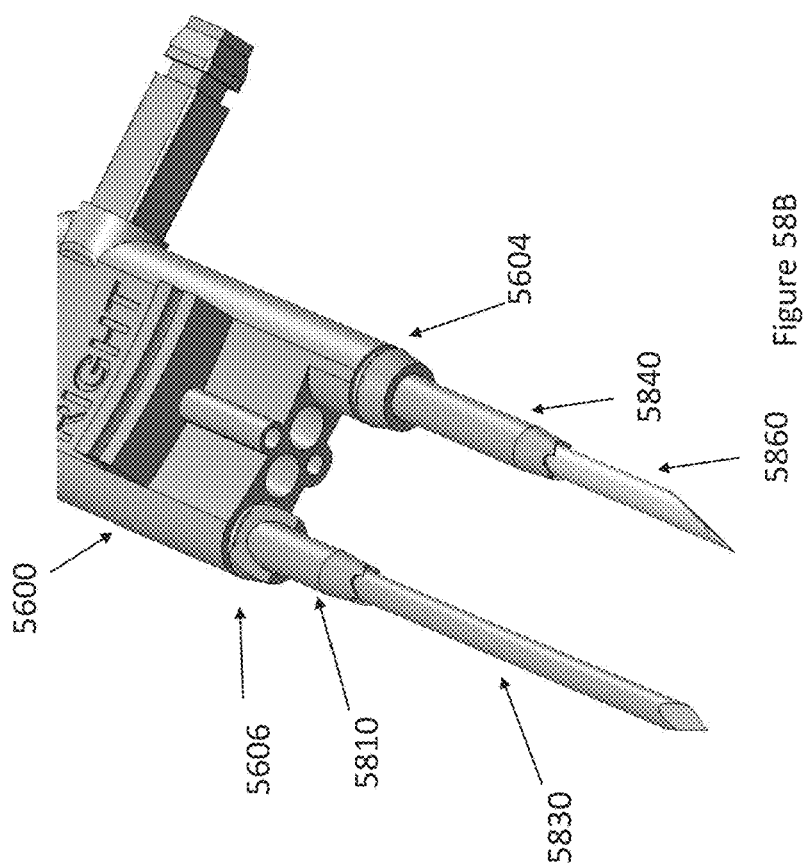

FIGS. 58A-58C illustrate a system of tools 5800 that can be to deliver one or more pins. FIGS. 58A-58C illustrate many components assembled, but the disclosure that follows describes an exemplary process starting with pin guide 5600 prior to assembly with any of the other components.

A sharp tipped guide tube 5810 can be placed through lumen 5607 in sacral side 5606 of pin guide 5600, as shown in FIGS. 58A and 58B. Cap 5820 may then be placed on the back (proximal) end of sacrum tube 5810, as shown in FIGS. 58A and 58C. In this example the two components are configured to allow cap 5820 to be rotated to cause rotation of sacrum tube 5810, and in this example they have a hex mating arrangement, as shown. Sacrum tube 5810 may then be rotated clockwise to advance sacrum tube 5810 through soft tissue. Once resistance is felt due to contact with the sacrum, sacrum tube 5810 may continue to be rotated until it is fully docked into the sacrum.

Sacrum pin 5830 (which may also be referred to an implant guide herein), which has a sharpened distal end, as shown, may then be placed into the proximal end of the lumen and through the lumen of sacrum tube 5810, as shown in FIGS. 58A and 58B. Pin 5830 may then be docked into the sacrum using a mallet, such as about 1 cm, without fully docking pin 5830 into the sacrum. Imaging in the outlet view, for example, may be used to ensure the trajectory of the sacrum pin 5830 will not intersect the foramina. Sacrum pin 5830 may then be further advanced into the sacrum to depth, such as about 2 cm short of the alar line in the lateral view. The sacrum pin at this time may be considered fully positioned in the sacrum.

As shown in FIGS. 58A and 58B, sharpened distal tipped ilium tube 5840 can then be placed through lumen 5605 in the ilium guide portion 5604 of pin guide 5600. A cap may be placed on the proximal end of ilium tube 5840 (Similar to cap 5820 with the sacrum tube 5810). The cap may then be rotated to cause rotation of ilium tube 5840 to advance the tube through soft tissue. Once resistance is felt due to contact with ilium bone, rotation of sharpened tube 5840 may continue until tube 5840 is fully docked in the ilium.

Ilium pin 5860 (see FIGS. 58A and 58B) may then be placed through the lumen of ilium tube 5840. A cap 5850 may be placed on the proximal end of pin 5860, as shown in FIGS. 58A and 58C, which allows rotation of the cap to cause rotation of pin 5860. Pin 5860 optionally includes a beveled distal end, as shown, which includes a pointed distal end and a flat beveled surface extending proximally and laterally from the pointed tip, as shown. In use, pin 5860 can be rotated (by rotating cap 5850) and oriented so that the flat beveled surface is facing laterally and the pointed surface is facing medially. The bevel causes the pin the better engage in the ilium and not skive along the lateral wall of the ilium without engaging the bone. Pin 5860 can then be docked into ilium bone with a mallet, about 1 cm. Imaging may be used to ensure the ilium pin 5860 is being advanced with the desired trajectory and is not skiving laterally, for example. The ilium pin can be advanced further, until it is about 2 cm short of the alar line in the lateral view. At this time, distal ends of sacrum pin 5830 and ilium pin 5860 are preferably in line, or aligned. Cap 5820 can then be placed over pin 5860 and slid onto the proximal end of ilium tube 5840. While holding pin 5860 with one hand, cap 5820 (which is rotationally secured to tube 5840) can be rotated counterclockwise with the other hand to remove ilium tube 5840 from the ilium. This can be repeated on the sacral side to remove sacral tube 5810. Once sacrum tube 5810 and ilium tube 5840 are free from bone, pin guide 5600 can be removed by sliding it proximally off pin 5830 and pin 5860, leaving sacrum pin 5830 in the sacrum and ilium pin 5860 in the ilium.

The above method is an example of positioning guide pins in an ilium and sacrum, and is an example of a set of tools that are adapted to do the same. Not all steps necessarily need to be performed, and one or more steps may occur out of sequence compared to the disclosure above. For example, an ilium pin may be fully docked in the ilium before the sacrum pin is fully docked in the sacrum.

The disclosure that follows provides exemplary methods and tools for implanting the implants herein across an SI joint from the dorsal approach, wherein a pin has been positioned in the ilium and a pin has been positioned in the sacrum. In alternative methods, only one pin may be positioned (in the ilium or the sacrum), and in other alternatives, the method of implanting the implant may not require any pin guides at all.

Figure 59E:
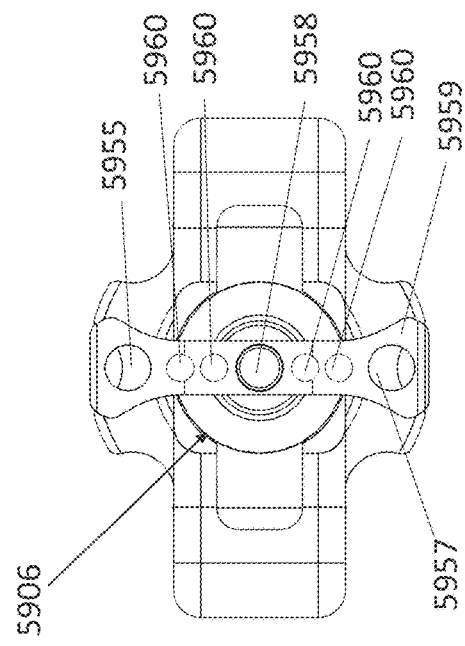
Figure 59F:
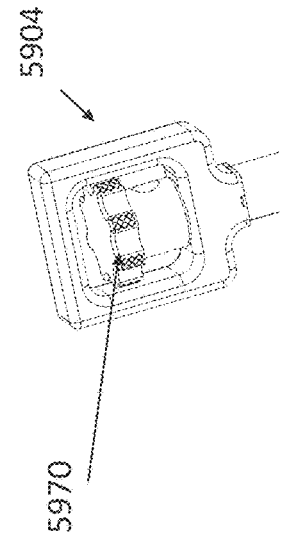
Figure 59C:
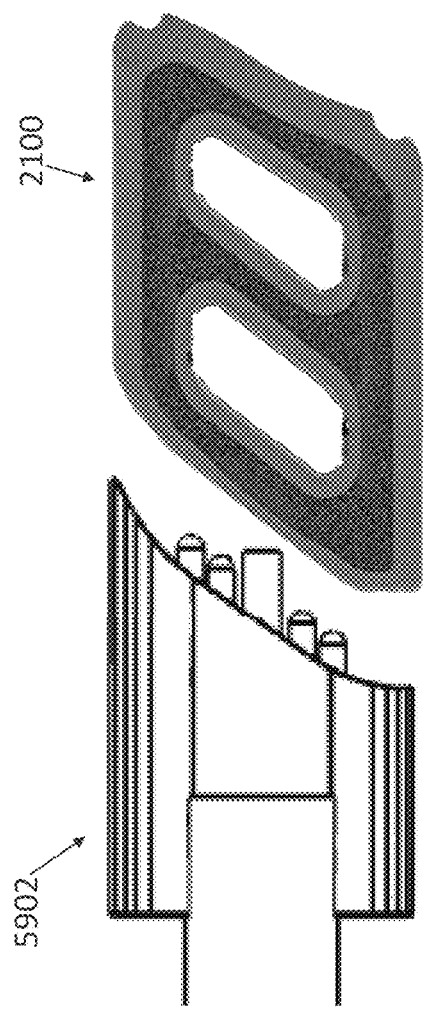
Figure 59D:
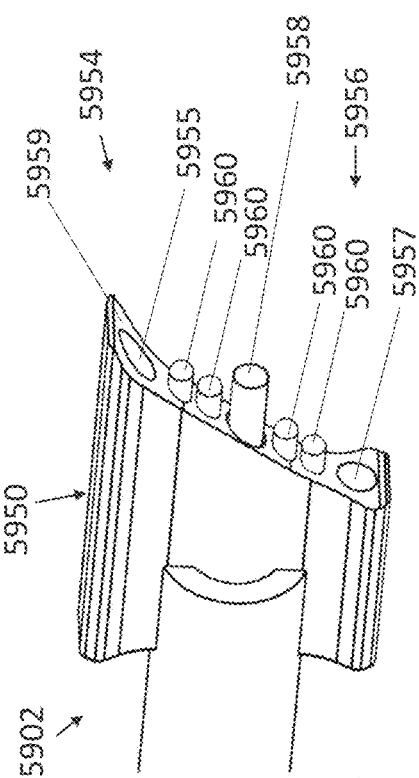

FIGS. 59A-59F illustrate an exemplary impactor 5900 that is configured to deliver the implant distally over the one or more pins and across the SI joint, with a portion of the implant in the ilium and a portion in the sacrum. Impactor 5900 includes distal region 5920 and proximal region 5904, and an elongate central region 5906 extending therebetween. FIG. 59A is a side view and FIG. 59B is a perspective view. FIG. 59C is a close up, side view of distal region 5902, FIG. 59D is a perspective view of distal region 5902, and FIG. 59E is a front end view. FIG. 59F is a perspective view of proximal region 5904. FIG. 59C also illustrates a relative distal position of implant 2100 from FIG. 21 to illustrate an exemplary implant relative to the distal region 5902 of impactor 5900. In FIG. 59C, the implant is not engaged or secured to the impactor.

As shown in FIG. 59D, distal region 5902 includes body 5950 that has, in this embodiment, a wafer configuration. Distal body 5950 has a distal face or surface 5959 with a configuration that is complimentary to the proximal end of the implant, as can be seen in FIG. 59C. The complimentary shaping helps the distal end of the impactor make contact with much or all of the proximal end of the implant, which provides an efficient transfer of the distally directed force from the impactor to the implant.

Distal portion 5950 includes an ilium portion 5954 that extends further distally than sacrum portion 5956, the general configuration of which, again, is complimentary to the proximal end of the implant, where the implant sacrum portion extends further proximally than the implant ilium portion (at least in this embodiment). Ilium portion 5954 includes ilium lumen 5955 that is sized and configured to receive therethrough the ilium pin (e.g., pin 5860), and sacrum portion 5956 includes sacrum lumen 5957 that is sized and configured to receive therethrough the sacrum pin (e.g., pin 5830). Impactor 5900 also includes an implant securing member 5958, which in this embodiment can have a threaded distal end that is configured to mate with an internal thread in the channel in the proximal end of the implant (e.g., FIG. 29). When implant securing member 5958 is secured to the implant via the threaded engagement, the implant can be moved by moving the impactor, which allows the implant to be removed from the patient if needed, or if the implant position needs to be adjusted. Implant securing member 5958 is in operational communication with implant control actuator 5970 in the proximal region 5904 of impactor 5900. In this embodiment implant control actuator 5970 is a rotatable member that can be rotated by the user to cause rotation of implant securing member 5958. Other mechanisms can be used to secure the impactor to the implant. The distal end of the impactor also includes a plurality of protrusions or fingers 5960, at least a first of which is on a first lateral half of distal region 5950 and a second of which is on a second lateral half of distal region 5950. The fingers on either side of the implant can help prevent rotational movement of the implant relative to the impactor as the impactor is used to distally advance the implant.

In use, and before the implant is implanted, the impactor may optionally be used to first deliver a cutting device such a broach to create a space where the implant will be implanted. A broach in this example may have a configuration that approximate the shape of the implant and/or has a proximal end that is complimentary to the distal face 5959 of the impactor. The broach can first be secured to the impactor, such as by engaging threads on securing member 5958 with internal threads in a channel in the proximal end of the broach. The broach and impactor assembly can then be advanced over the two pins, with the ilium pin passing through ilium lumen 5955 and the sacrum pin passing through sacrum lumen 5957. The broach can be impacted to near the ends of the pins. A broach (if used) and impactor can then be retracted proximally to remove the broach from the patient. The optional broach can then be removed from the impactor.

The implant can then be loaded onto the distal end of the impactor and secured to the impactor, such as with the threaded engagement between the two, examples of which are described herein. This allows the axial position of the implant to be controlled by axially moving the impactor. Loading the implant also comprises aligning the plurality of fingers (e.g., fingers 5960) with the recesses in the proximal end of the implant, examples of which are described herein with respect to FIGS. 29-31. The lumens of the impactor are now also aligned with implant lumens (if the implant has one or more lumens).

Figure 60:
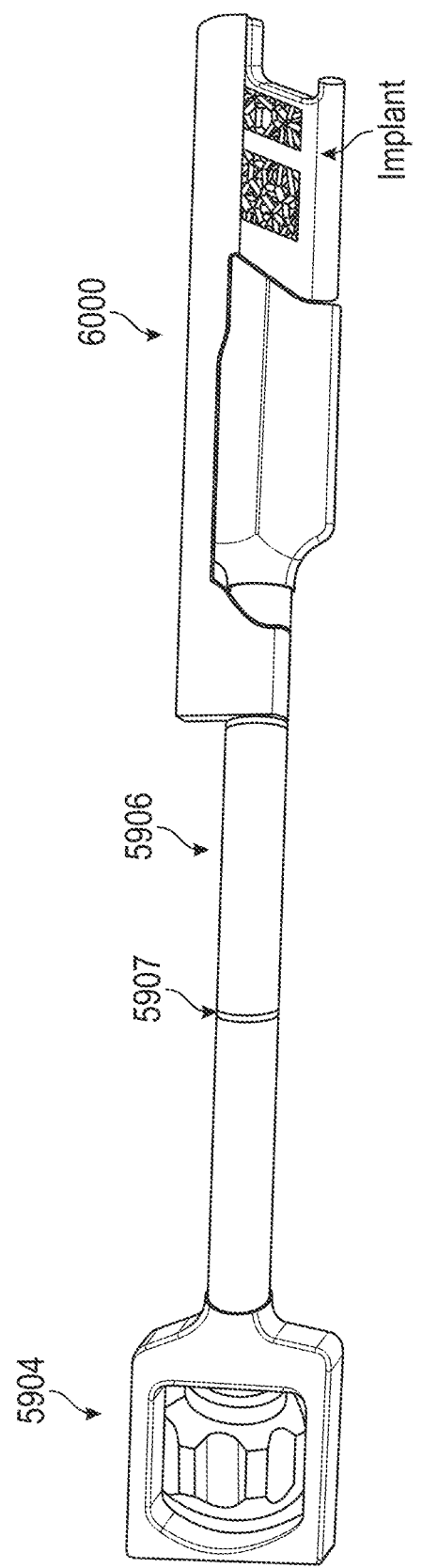
FIG. 60 illustrates an exemplary impactor, an exemplary depth gauge, and an exemplary implant.

The implant (and impactor secured to the implant) is then advanced onto the proximal ends of the pins, and the implant-impactor assembly is slid distally over the pins. The pins will also extend into the two lumens of the impactor. The implant is then impacted with a distally directed force (e.g., with a mallet) to distally advance the implant. One option is to use imaging (e.g., fluoro imaging) and impact the implant to the desired depth while viewing the image (e.g., lateral view with fluoro). Alternatively (or additionally), a sacral impactor depth gauge can be used, which can be used to impact to a positive stop when using the sacral impactor depth gauge, an example of which is shown in FIG. 60 as depth gauge 6000. Depth gauge 6000 can be secured to the impactor, as shown in FIG. 60, and the implant can be impacted until the proximal end of sacral impactor depth gauge 6000 is aligned with marking 5907 on the impactor. The impactor will be advanced relative to the depth gauge when impacted. Other visual markings can be used to provide a visual indication that the impact has been sufficiently impacted.

Figure 61B:
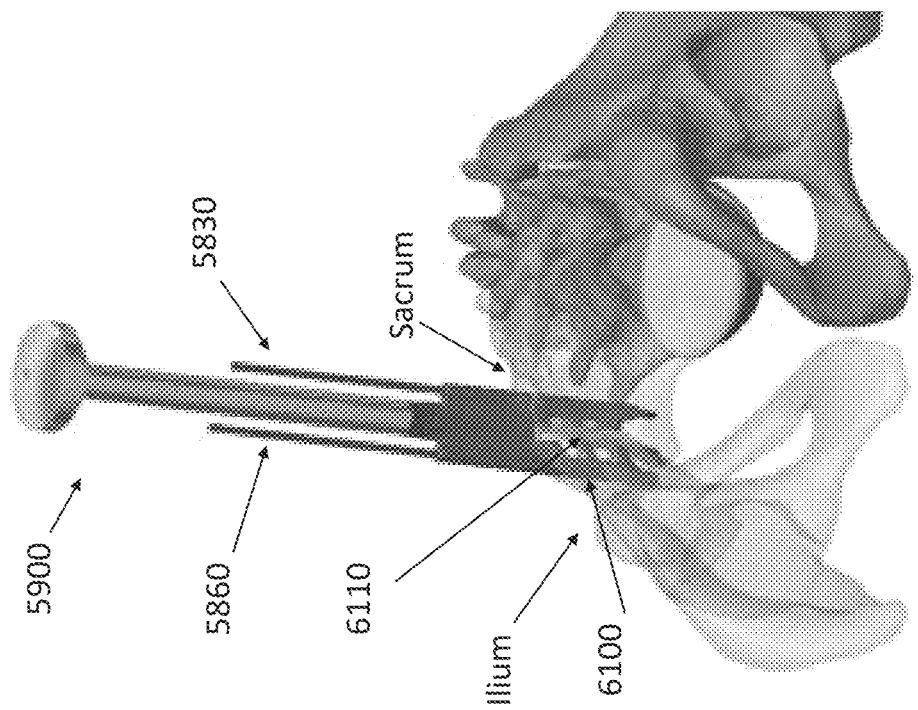
FIGS. 61A and 61B illustrate an implant secured to an impactor and implanted across an SI joint from the dorsal approach.
Figure 61A:
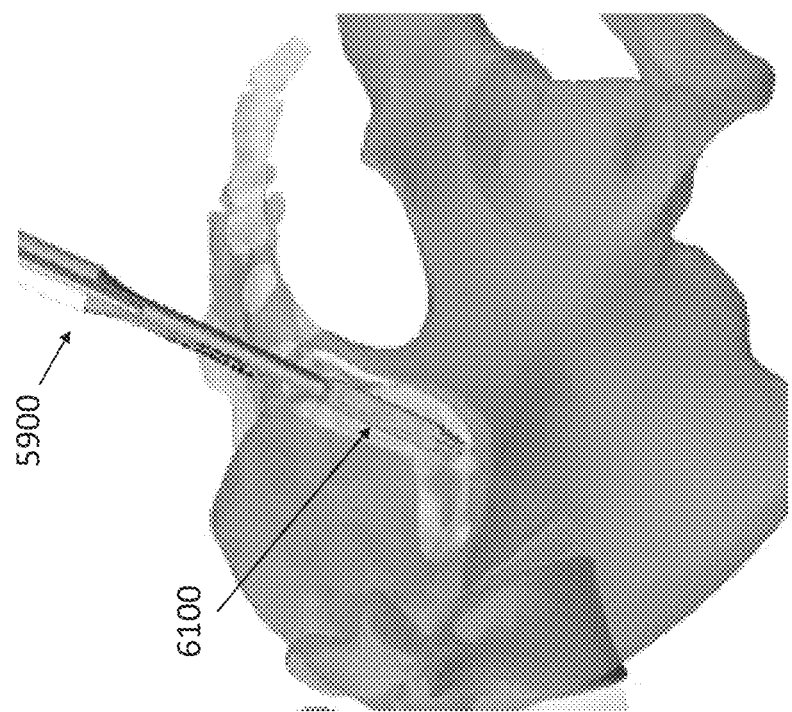

FIG. 61A illustrates a lateral model view showing an implant implanted across an SI joint, and still secured to impactor 5900. FIG. 61B illustrates a model view of implant 6100 implanted across SI joint 6110, with a portion of implant 6100 implanted in the ilium and a portion in the sacrum. Pins 5860 and 5830 are shown, as is exemplary impactor 5900.

When the implant is in the desired position, the implant can be disengaged from the impactor, such as by rotating actuator 5970, which disengages the threaded engagement.

Figure 63C:
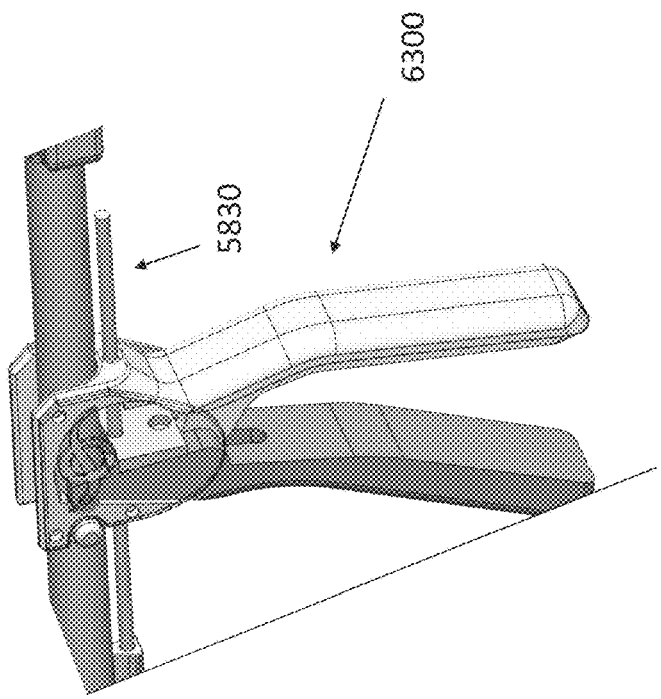
Figure 63B:
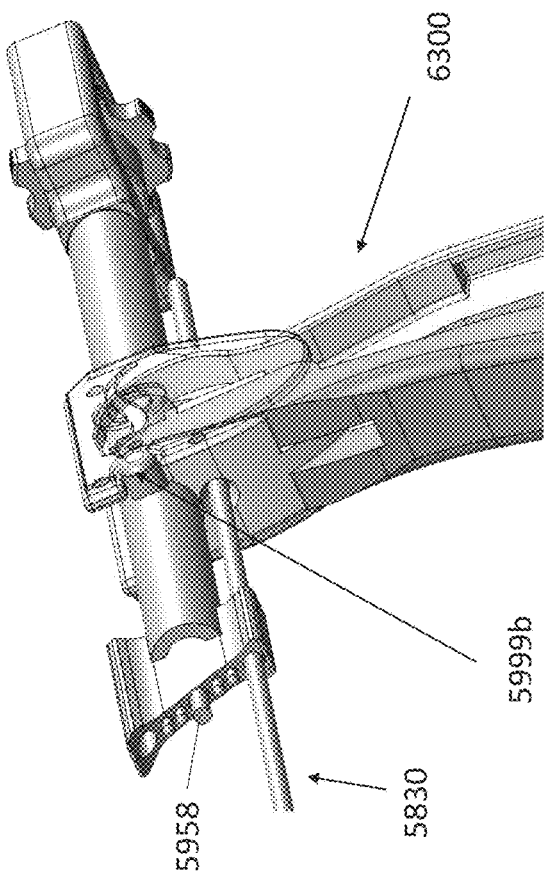

FIGS. 63A-63C illustrate an exemplary pin removal device 6300 that is adapted to be used in combination with impactor 5900 (or other impactors) to remove the ilium and sacrum pins. After the implant has been implanted, the pins remain extending through the lumens of the impactor (only one pin is shown in FIGS. 63A-63C). To remove the pins, pin removal device 6300 can be placed over a pin and set on first and second impactor bosses 5999*a* and 5999*b*, as shown in FIGS. 63-63C. As handles 6302 and 6304 of removal device 6300 are squeezed together, the pin is retracted proximally relative to the impactor until it has been removed from the bone and out of the patient. The mechanism may be similar to or the same as that found in wood clamps, such as the Irwin® QUICK-GRIP® clamp, the entire disclosure of which is incorporated by reference herein. Both pins can be removed from the bone in this manner, leaving the implant implanted in the SI joint.

Figure 62B:
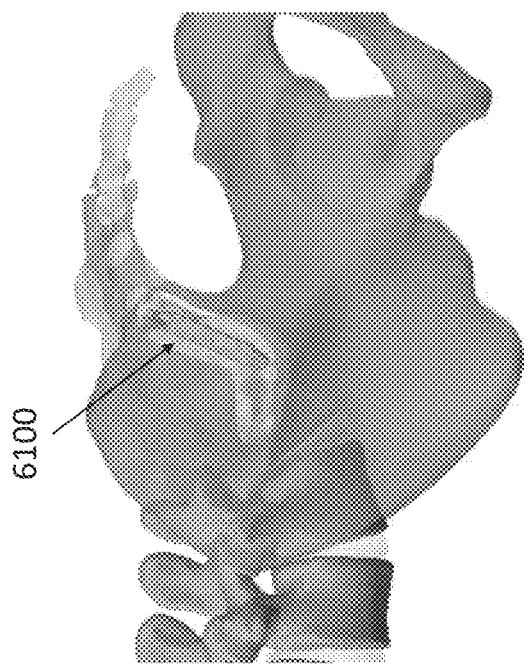
FIGS. 62A and 62B illustrate an implant implanted across an SI joint after pins have been removed.
Figure 62A:
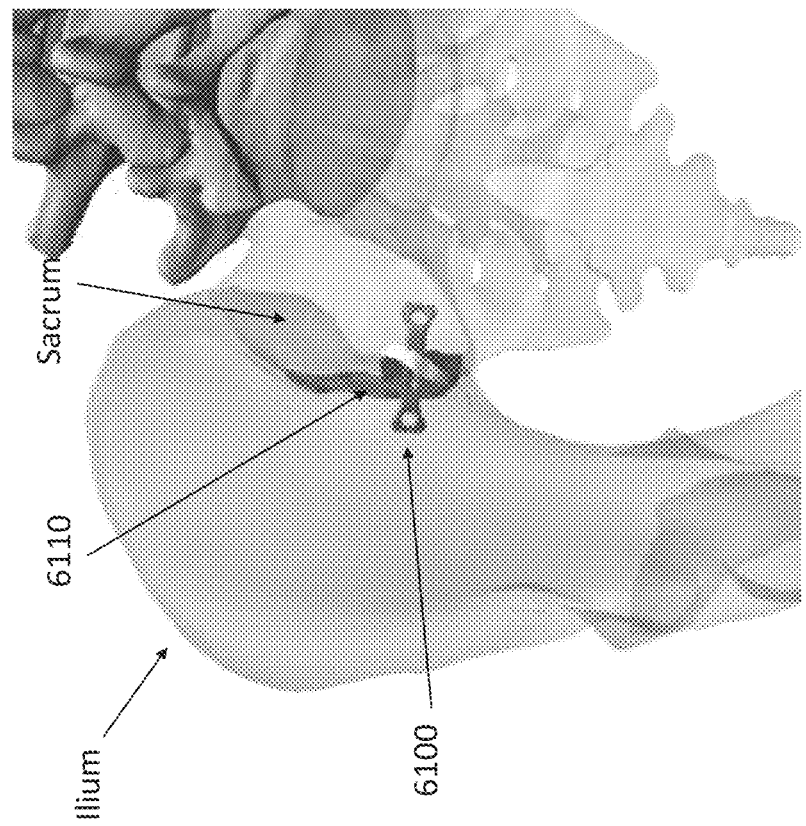

FIG. 62A illustrates a model view of implant 6100 implanted across SI Joint 6110 (left joint) after pin and impactor removal, and FIG. 62B illustrates a lateral model of implant 6100 across the SI joint after pin and impactor removal.

What is claimed is:

1. A method of positioning a sacro-iliac ("SI") joint stabilizing implant across an SI joint from a dorsal approach, comprising:

advancing an elongate sacrum pin from a dorsal starting point into a sacrum of a subject such that a distal end of the sacrum pin is in the sacrum and a proximal end of the sacrum pin is disposed outside of the subject;

advancing an elongate ilium pin from a dorsal starting point into an ilium of the subject such that a distal end of the ilium pin is in the ilium and a proximal end of the ilium pin is disposed outside of the subject;

advancing a distal opening of an ilium lumen that is in an ilium portion of an SI joint stabilizing implant over the ilium pin and advancing a distal opening of a sacrum lumen that is in a sacrum portion of the SI joint stabilizing implant over the sacrum pin, wherein the distal opening of the ilium lumen extends further distally than the distal opening of the sacrum lumen;

advancing the implant distally over and relative to the sacrum pin and the ilium pin until the implant is across the SI joint with the ilium portion in the ilium and the sacrum portion in the sacrum, wherein the distal opening of the ilium portion is advanced further distally than the distal opening of the sacrum portion; and removing the ilium pin and the sacrum pin from the subject, leaving the implant positioned across the SI joint.

2. The method of claim 1, wherein advancing the ilium pin comprises advancing the ilium pin into the ilium between lateral and medial cortical walls of the ilium.

3. The method of claim 1, wherein advancing the sacrum pin occurs in time prior to advancing the ilium pin.

4. The method of claim 1, wherein advancing the sacrum pin comprises preventing a distal end of the sacrum pin from extending beyond the alar line.

5. The method of claim 1, wherein advancing the ilium pin comprises preventing a distal end of the ilium pin from extending beyond the alar line.

6. The method of claim 1, further comprising securing an impactor to a proximal end of the implant.

7. The method of claim 6, further comprising extending an impactor ilium lumen over the ilium pin and extending an impactor sacrum lumen over the sacrum pin.

8. The method of claim 7, wherein securing the impactor to the proximal end of the implant comprises engaging an impactor threaded elongate member with an internally threaded channel in the implant.

9. The method of claim 7, wherein advancing the implant distally over and relative to the sacrum pin and the ilium pin comprises applying a distally directed force on the impactor.

10. The method of claim 1, further comprising bringing a distal end of an impactor adjacent to a proximal end of the implant, wherein the distal end of the impactor has a shape that is complimentary to a proximal end of the implant.

11. The method of claim 1, wherein bringing a distal end of an impactor adjacent to a proximal end of the implant comprises causing an ilium side of the impactor to be further distally than a sacrum side of the impactor.

12. The method of claim 1, further comprising, prior to advancing the distal openings over the ilium pin and sacrum pin, advancing a broach over and distally relative to the ilium pin and the sacrum pin, and advancing the broach into tissue across the SI joint.

13. The method of claim 12, further comprising securing an impactor to a proximal end of the broach, and wherein advancing the broach comprises applying a distally directed force on the impactor.

* * * * *